US008912147B2

(12) United States Patent
Lorberboum-Galski

(10) Patent No.: US 8,912,147 B2
(45) Date of Patent: Dec. 16, 2014

(54) MITOCHONDRIAL PROTEINS CONSTRUCTS AND USES THEREOF

(71) Applicant: BioBlast Pharma Ltd., Tel Aviv (IL)

(72) Inventor: Haya Lorberboum-Galski, Jerusalem (IL)

(73) Assignee: BioBlast Pharma Ltd., Tel Aviv (IL)

( * ) Notice: Subject to any disclaimer, the term of this patent is extended or adjusted under 35 U.S.C. 154(b) by 0 days.

(21) Appl. No.: 14/034,224

(22) Filed: Sep. 23, 2013

(65) Prior Publication Data

US 2014/0308262 A1  Oct. 16, 2014

Related U.S. Application Data

(60) Provisional application No. 61/811,934, filed on Apr. 15, 2013, provisional application No. 61/869,981, filed on Aug. 26, 2013.

(51) Int. Cl.
*A61K 38/17* (2006.01)
*C07K 19/00* (2006.01)
*C07K 14/16* (2006.01)
*C07K 14/47* (2006.01)
*C07K 14/005* (2006.01)
*C12N 9/02* (2006.01)

(52) U.S. Cl.
CPC .............. *C07K 14/47* (2013.01); *C07K 2319/01* (2013.01); *C07K 2319/07* (2013.01); *C07K 14/005* (2013.01); *C12N 9/0091* (2013.01); *A61K 38/1709* (2013.01); *Y10S 530/826* (2013.01); *Y10S 530/827* (2013.01)
USPC ............ 514/21.2; 514/1.1; 514/1.2; 530/350; 530/826; 530/827

(58) Field of Classification Search
None
See application file for complete search history.

(56) References Cited

U.S. PATENT DOCUMENTS

2011/0190224 A1* 8/2011 Payne .......................... 514/21.2

FOREIGN PATENT DOCUMENTS

WO  WO 2009/098682     8/2009
WO  WO-2009098682 A2   8/2009

OTHER PUBLICATIONS

Yoon et al., TAT-mediated delivery of human glutamate dehydrogenase into PC12 cells, Neurochemistry Int., 2002, 41, 37-42.*
George et al., An analysis of protein domain linkers: their classification and role in protein folding, Protein Eng., 2003, 15, 871-79.*
GenBank, Accession No. NM_000144.4, 2011, www.ncbi.nlm.nih.gov.*
Bencze et al. "The Structure and Function of Frataxin." *Crit. Rev. Biochem. Mol. Biol.* 41.5(2006):269-291.
Brady et al. "Enzyme-Replacement Therapy for Metabolic Storage Disorders." *Lancet Neurol.* 3(2004):752-756.
Braun et al. "The Mitochondrial Processing Peptidase." *Int. J. Biochem. Cell Biol.* 29.8-9(1997):1043-1045.
Brautigam et al. "Crystal Structure of Human Dihydrolipoamide Dehydrogenase: NAD+/NADH Binding and the Structural Basis of Disease-Causing Mutations." *J. Mol. Biol.* 350(2005):543-552.
Bulteau et al. "Frataxin Acts as an Iron Chaperone Protein to Modulate Mitochondrial Aconitase Activity." *Science.* 305(2004):242-245.
Campuzano et al. "Frataxin is Reduced in Friedreich Ataxia Patients and is Associated with Mitochondrial Membranes." *Hum. Mol. Genet.* 6.11(1997):1771-1780.
Cavadini et al. "Two-Step Processing of Human Frataxin by Mitochondrial Processing Peptidase." *J. Biol. Chem.* 275. 52(2000):41469-41475.
Cheng et al. "Identification and Characterization of the Mitochondrial Targeting Sequence and Mechanism in Human Citrate Synthase." *J. Cell. Biol.* 107(2009):1002-1015.
Chinnery et al. "Mitochondria." *J. Neurol. Neurosurg. Psychiatry.* 74(2003):1188-1199.
Del Gaizo et al. "Targeting Proteins to Mitochondria Using TAT." *Mol. Genet. Metab.* 80(2003):170-180.
Delatycki et al. "Direct Evidence that Mitochondrial Iron Accumulation Occurs in Friedreich Ataxia." *Ann. Neurol.* 45(1999):673-675.
DiMauro et al. "Mitochondrial Respiratory-Chain Diseases." *N. Eng. J. Med.* 348(2003):2656-2668.
Dürr et al. "Clinical and Genetic Abnormalities in Patients with Friedreich's Ataxia." *N. Engl. J. Med.* 335.16(1996):1169-1175.
Frankel et al. "Cellular Uptake of the Tat Protein from Human Immunodeficiency Virus." *Cell.* 55(1988):1189-1193.
Futaki et al. "Arginine-Rich Peptides." *J. Biol. Chem.* 276. 8(2001):5836-5840.
Gakh et al. "Mitochondrial Processing Peptidases." *Biochim. Biophys. Acta.* 1592(2002):63-77.
Gakh et al. "Normal and Friedreich Ataxia Cells Express Different Isoforms of Frataxin with Complementary Roles in Iron-Sulfur Cluster Assembly." *J. Biol. Chem.* 285(2010):38486-38501.
Gavel et al. "Cleavage-Site Motifs in Mitochondrial Targeting Peptides." *Protein Eng.* 4.1(1990):33-37.
Green et al. "Autonomous Functional Domains of Chemically Synthesized Human Immunodeficieny Virus Tat *Trans*-Activator Protein." *Cell.* 55(1988):1179-1188.
Guo et al. "Transduction of Functionally Active TAT Fusion Proteins into Cornea." *Exp. Eye Res.* 78(2004):997-1005.
Harding. "Friedreich's Ataxia: A Clinical and Genetic Stuy of 90 Families with an Analysis of Early Dignostic Criteria and Intrafamilial Clustering of Clinical Features." *Brain.* 104(1981):589-620.
Horwich. "Protein Import into Mitochondria and Peroxisomes." *Curr. Opin. Cell Biol.* 2(1990):625-633.
Kabouridis. "Biological Applications of Protein Transduction Technology." *Trends Biochem.* 21.11(2003):498-503.
Lodi et al. "Deficit of in vivo Mitochondrial ATP Production in Patients with Friedreich Ataxia." *PNAS.* 96(1999):11492-11495.

(Continued)

*Primary Examiner* — Rebecca Prouty
*Assistant Examiner* — Todd M Epstein
(74) *Attorney, Agent, or Firm* — Cooley LLP

(57) ABSTRACT

The invention provides fusion protein constructs comprising a functional mitochondrial protein and methods of treating mitochondrial disorders by the fusion proteins and compositions thereof.

7 Claims, 22 Drawing Sheets

(56) References Cited

OTHER PUBLICATIONS

Luft. "Transducing Proteins to Manipulate Intracellular Targets." *J. Mol. Med.* 81(2003):521-523.
Perlman. "A Review of Friedreich Ataxia Clinical Trial Results." *J. Child Neurol.* 27.9(2012):1217-1222.
Rapoport et al. "Succesful TAT-Mediated Enzyme Replacement Therapy in a Mouse Model of Mitochondrial E3 Deficiency." *J. Mol. Med.* 89(2011):161-170.
Rapoport et al. "TAT-Mediated Delivery of LAD Restores Pyruvate Dehydrogenase Complex Activity in the Mitochondria of Patients with LAD Deficiency." *Mol. Ther.* 16.4(2008):691-697.
Richardson et al. "Estrogen Prevents Oxidative Damage to the Mitochondria in Friedreich's Ataxia Skin Fibroblasts." *PLoS One.* 7.4(2012):e34600.
Rötig et al. "Aconitase and Mitochondrial Iron-Sulphur Protein Deficiency in Friedreich Ataxia." *Nat. Genet.* 17(1997):215-217.
Saada et al. "C6ORF66 is an Assembly Factor of Mitochondrial Complex I." *Am. J. Hum. Genet.* 82(2008):32-38.
Santos et al. "Friedreich Ataxia: Molecular Mechanisms, Redox Considerations, and Therapeutic Opportunities." *Antioxidant Redox Signal.* 13.5(2010):651-690.
Schmucker et al. "The in vivo Mitochondrial Two-Step Maturation of Human Frataxin." *Hum. Mol. Genet.* 17.22(2008):3521-3531.
Schulz et al. "Diagnosis and Treatment of Friedreich Ataxia: A European Perspective." *Neurol.* 5(2009):222-234.
Schwarze et al. "In Vivo Protein Transduction: Delivery of a Biologically Active Protein into the Mouse." *Science.* 285(1999):1569-1572.
Tsou et al. "Pharmacotherapy for Friedreich Ataxia." *CNS Drugs.* 23.3(2009):213-223.
Vyas et al. "A TAT-Frataxin Fusion Protein Increases Lifespan and Cardiac Function in a Conditional Friedreich's Ataxia Mouse Model." *Hum. Mol. Genet.* 21.6(2012):1230-1247.
Wang et al. "Short-Term, High Dose Enzyme Replacement Therapy in Sialidosis Mice." *Mol. Genet. Metab.* 85(2005):181-189.
Chinnery, P. F. et al., "Mitochondria," J. Neurol. Neurosurg. Psychiatry, 74:1188-1199 (2003).
DiMauro, S. et al., "Mitochondrial respiratory-chain diseases," N. Engl. J. Med., 348(26):2656-2668 (2003).
Brautigam, C. A. et al., "Crystal structure of human dihydrolipoamide dehydrogenase: NAD+/NADH binding and the structural basis of disease-causing mutations," J. Mol. Biol., 350(3):543-552 (2005).
Brady, R. O. et al., "Enzyme-replacement therapy for metabolic storage disorders," Lancet Neurol., 3(12):752-756 (2004).
Wang, D. et al., "Short-term, high dose enzyme replacement therapy in sialidosis mice," Mol. Genet. Metab., 85(3):181-189 (2005).
Luft, F. C., "Transducing proteins to manipulate intracellular targets," J Mol. Med. (Berl), 81(9):521-523 (2003).
Kabouridis, P. S., "Biological applications of protein transduction technology," Trends Biotechnol., 21(11):498-503 (2003).
Green, M. et al., "Autonomous functional domains of chemically synthesized human immunodeficiency virus tat trans-activator protein," Cell, 55(6):1179-1188 (1988).
Frankel, A. D. et al., "Cellular uptake of the tat protein from human immunodeficiency virus," Cell, 55(6):1189-1193 (1988).
Futaki, S. et al., "Arginine-rich peptides. An abundant source of membrane-permeable peptides having potential as carriers for intracellular protein delivery," J. Biol. Chem., 276(8):5836-5840 (2001).
Schwarze, S. R. et al., "In vivo protein transduction: delivery of a biologically active protein into the mouse," Science, 285(5433):1569-1572 (1999).
Guo, X. et al., "Transduction of functionally active TAT fusion proteins into cornea," Exp. Eye Res., 78(5):997-1005 (2004).
Del Gaizo, V. et al., "Targeting proteins to mitochondria using TAT," Mol. Genet. Metab., 80(1-2):170-180 (2003).
Harding, A. E., "Friedreich's ataxia: a clinical and genetic study of 90 families with an analysis of early diagnostic criteria and intrafamilial clustering of clinical features," Brain, 104:589-620 (1981).

Schulz, J. B. et al., "Diagnosis and treatment of Friedreich ataxia: a European perspective," Nat. Rev. Neurol., 5:222-234 (2009).
Durr, A. et al., "Clinical and genetic abnormalities in patients with Friedreich's ataxia," N. Engl. J. Med., 335(16):1169-1175 (1996).
Campuzano, V. et al., "Frataxin is reduced in Friedreich ataxia patients and is associated with mitochondrial membranes," Hum. Mol. Genet., 6(11):1771-1780 (1997).
Rotig, A. et al., "Aconitase and mitochondrial iron-sulphur protein deficiency in Friedreich ataxia," Nat. Genet., 17(2):215-217 (1997).
Lodi, R. et al., "Deficit of in vivo mitochondrial ATP production in patients with Friedreich ataxia," Proc. Natl. Acad. Sci. USA, 96(20):11492-11495 (1999).
Delatycki, M. B. et al., "Direct evidence that mitochondrial iron accumulation occurs in Friedreich ataxia," Ann. Neurol., 45(5):673-675 (1999).
Tsou, A. Y. et al., "Pharmacotherapy for Friedreich ataxia," CNS Drugs, 23(3):213-223 (2009).
Perlman, S. L., "A review of Friedreich ataxia clinical trial results," J. Child. Neurol., 27(9):1217-1222 (2012).
Rapoport, M. et al., "TAT-mediated delivery of LAD restores pyruvate dehydrogenase complex activity in the mitochondria of patients with LAD deficiency," Mol. Ther., 16(4):691-697 (2008).
Rapoport, M. et al., "Successful TAT-mediated enzyme replacement therapy in a mouse model of mitochondrial E3 deficiency," J. Mol. Med. (Berl), 89(2):161-170 (2011).
Vyas, P. M. et al., "A TAT-frataxin fusion protein increases lifespan and cardiac function in a conditional Friedreich's ataxia mouse model," Hum. Mol. Genet., 21(6):1230-1247 (2012).
Gakh, O. et al., "Mitochondrial processing peptidases," Biochim. Biophys. Acta, 1592(1):63-77 (2002).
Cavadini, P. et al., "Two-step processing of human frataxin by mitochondrial processing peptidase. Precursor and intermediate forms are cleaved at different rates," J. Biol. Chem., 275(52):41469-41475 (2000).
Schmucker, S. et al., "The in vivo mitochondrial two-step maturation of human frataxin," Hum. Mol. Genet., 17(22):3521-3531 (2008).
Gakh, O. et al., "Normal and Friedreich ataxia cells express different isoforms of frataxin with complementary roles in iron-sulfur cluster assembly," J. Biol. Chem., 285(49):38486-38501 (2010).
Gavel, Y. et al., "Cleavage-site motifs in mitochondrial targeting peptides," Protein Eng., 4(1):33-37 (1990).
Braun, H. P. et al., "The mitochondrial processing peptidase," Int. J. Biochem. Cell Biol., 29:1043-1045 (1997).
Horwich, A., "Protein import into mitochondria and peroxisomes," Curr. Opin. Cell Biol., 2:625-633 (1990).
Saada, A. et al., "C60RF66 is an assembly factor of mitochondrial complex I," Am. J. Hum. Genet., 82(1):32-38 (2008).
Cheng, T. L. et al., "Identification and characterization of the mitochondrial targeting sequence and mechanism in human citrate synthase," J. Cell. Biochem., 107(5):1002-1015 (2009).
Santos, R. et al., "Friedreich ataxia: molecular mechanisms, redox considerations, and therapeutic opportunities," Antioxid. Redox Signal, 13(5):651-690 (2010).
Bulteau, A. L. et al., "Frataxin acts as an iron chaperone protein to modulate mitochondrial aconitase activity," Science, 305(5681):242-245 (2004).
Richardson, T. E. et al., "Estrogen prevents oxidative damage to the mitochondria in Friedreich's ataxia skin fibroblasts," PLoS One, 7(4):e34600 (2012).
NCBI Protein Database Accession No. P12694; OMIM:248600 (Oct. 1, 1989).
NCBI Protein Database Accession No. P21953 (Aug. 1, 1991).
NCBI Protein Database Accession No. P11310; OMIM:201450 (Jul. 1, 1989).
NCBI Protein Database Accession No. P49748; OMIM:201475 (Oct. 1, 1996).
NCBI Protein Database Accession No. P40939; OMIM:609015 (Feb. 1, 1995).
NCBI Protein Database Accession No. P55084 (Oct. 1, 1996).
NCBI Protein Database Accession No. P11177; OMIM:208800 (Jul. 1, 1989).
NCBI Protein Database Accession No. P08559; OMIM:312170 (Aug. 1, 1988).

(56) References Cited

OTHER PUBLICATIONS

NCBI Protein Database Accession No. Q16595 (Jul. 15, 1999).
OMIM:252010 (Sep. 30, 1987).
NDUFV1; OMIM:161015 (Jan. 14, 1993).
NDUFV2; OMIM:600532 (May 17, 1995).
NDUFS1; OMIM:157655 (Jul. 1, 1993).
NDUFS2; OMIM:602985 (Aug. 19, 1998).
NDUFS3; OMIM:603846 (May 25, 1999).
NDUFS4; OMIM:602694 (Jun. 8, 1998).
NDUFS6; OMIM:603848 (May 25, 1999).
NDUFS7; OMIM:601825 (May 23, 1997).
NDUFS8; OMIM:602141 (Dec. 2, 1997).
NDUFA2; OMIM:602137 (Dec. 2, 1997).
OMIM:220110 (Jun. 3, 1986).
MTCO1; OMIM:516030 (Mar. 2, 1993).
MTCO2; OMIM:516040 (Mar. 2, 1993).
MTCO3; OMIM:516050 (Mar. 2, 1993).
COX1O; OMIM:602125 (Nov. 17, 1997).
COX6B1; OMIM:124089 (Sep. 24, 1991).
SCO1; OMIM:603644 (Mar. 15, 1999).
FASTKD2; OMIM:612322 (Sep. 26, 2008).
SCO2; OMIM:604272 (Nov. 1, 1999).
OMIM:252011 (Dec. 9, 1989).
OMIM:124000 (Jun. 4, 1986).
OMIM:604273 (Nov. 1, 1999).
Del Gaizo et al., "Targeting proteins to mitochondria using TAT", Molecular Genetics and Metabolism, Sep. 1, 2003, 170-180, 80(1-2), Amsterdam, NL.
Koczor et al., "Mitochondrial DNA Damage Initiates a Cell Cycle Arrest by a Chk2-associated Mechanism in Mammalian Cells", J Biol Chem., Oct. 19, 2009, 36191-36201, 284(52), US.
Partial International Search Report for PCT/IL2014/050354, mailed Jul. 18, 2014.

\* cited by examiner

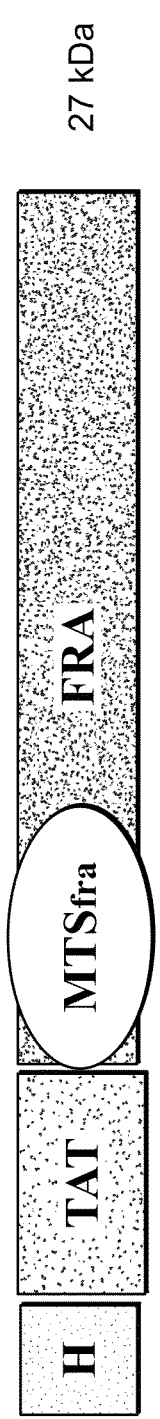
FIG. 1A
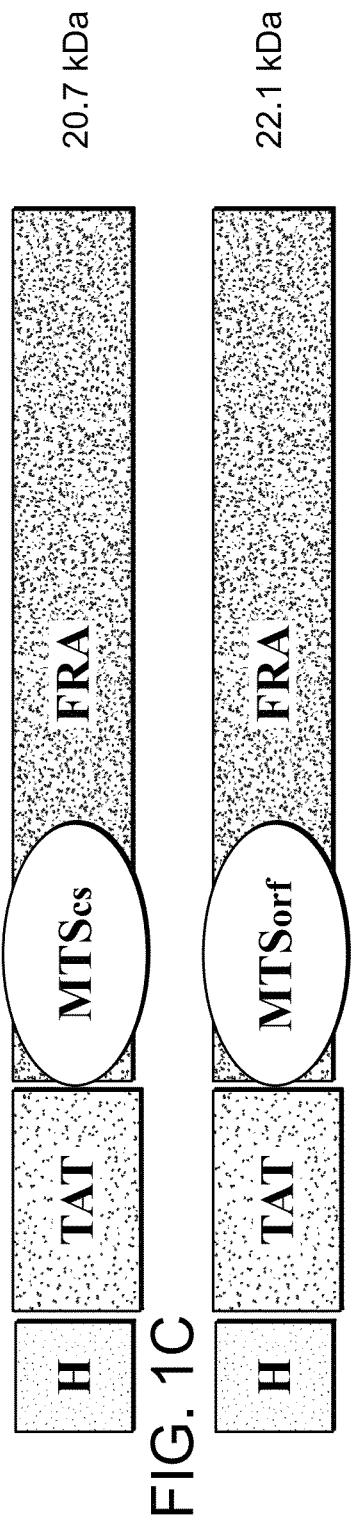
FIG. 1B
FIG. 1C
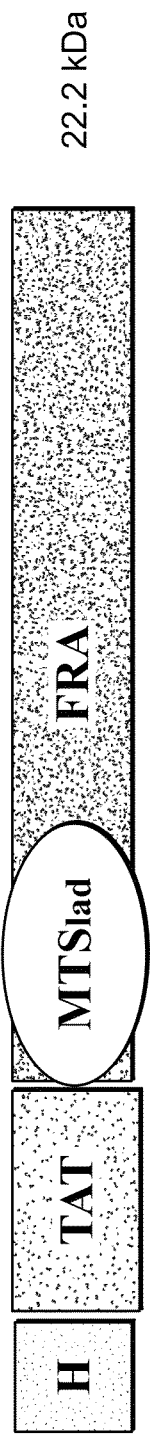
FIG. 1D

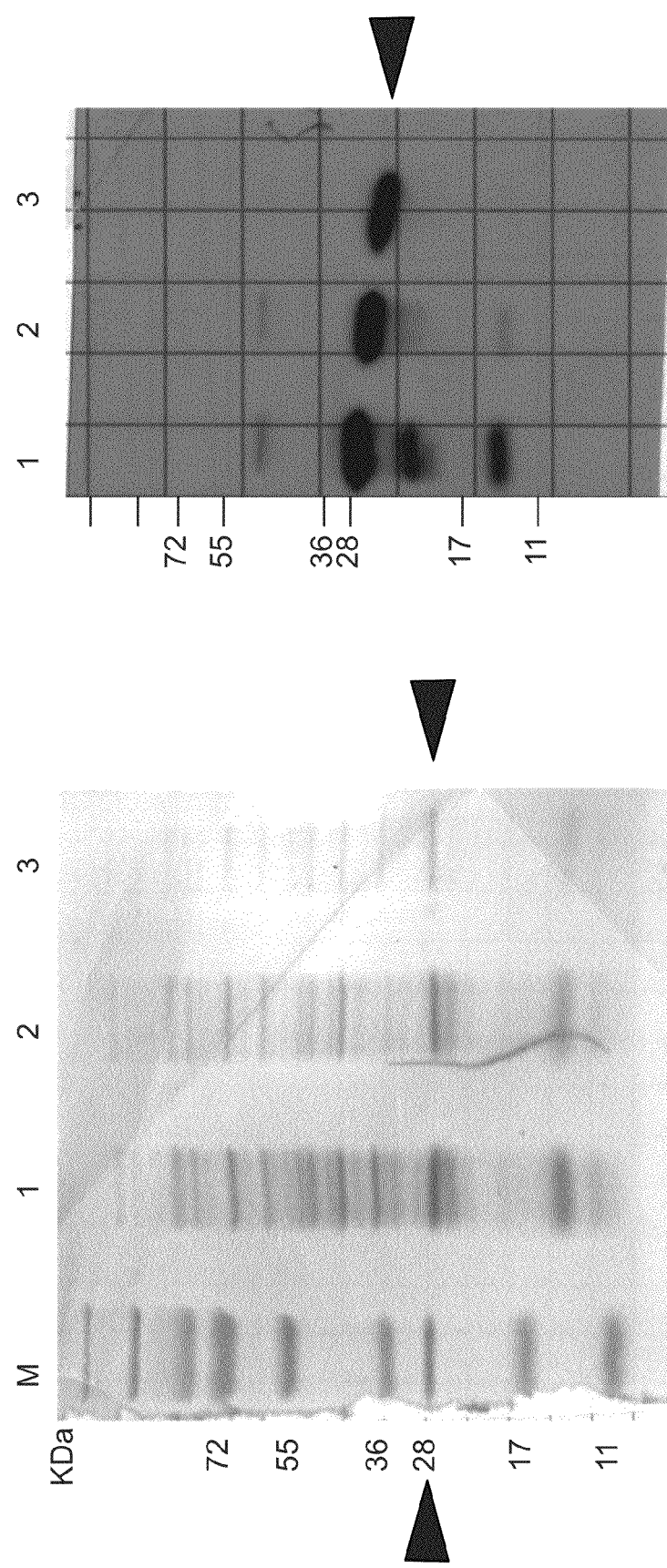

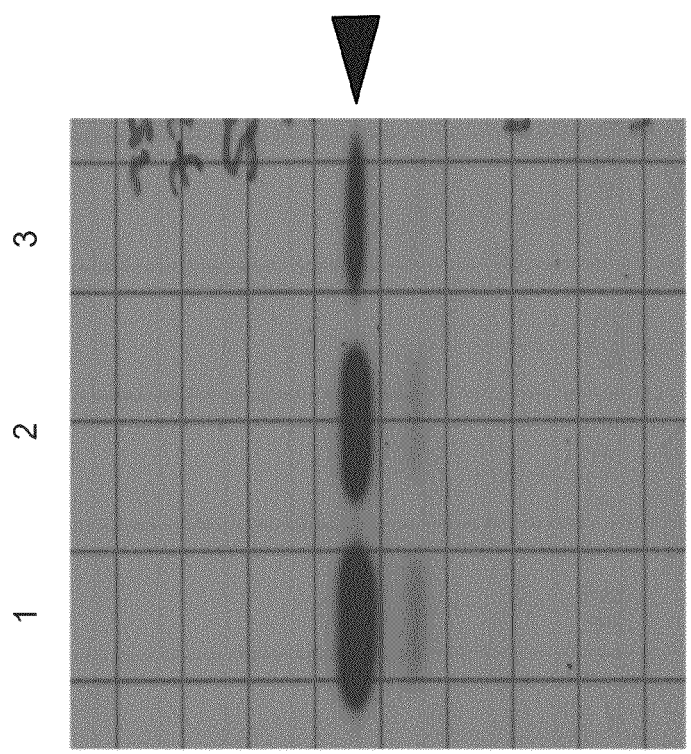
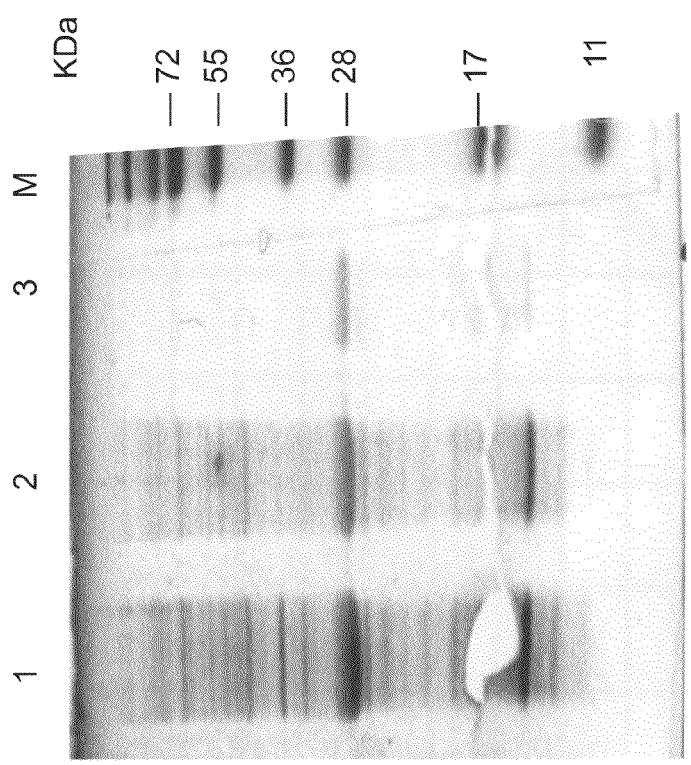
FIG. 3B
FIG. 3A

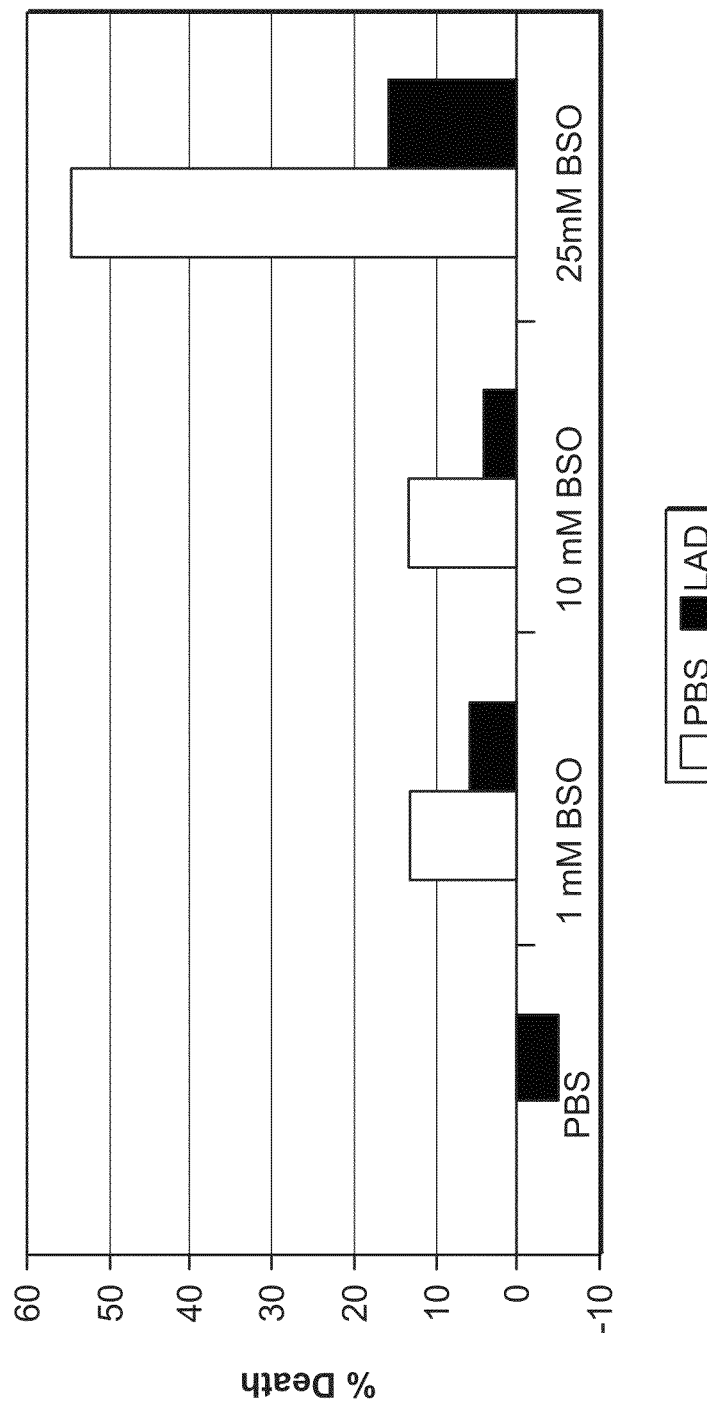

FIG. 13A

MRKKRRQRRRGSDPWTLGRRAVAGLLASPSPAQAQTLTRVPRPAELAPLCGRR
GLRTDIDATCTPRRASSNQRGLNQIWNVKKQSVYLMNLRKSGTLGHPGSLDETT
YERLAEETLDSLAEFFEDLADKPYTFEDYDVSFGSGVLTVKLGGDLGTYVINKQT
PNKQIWLSSPSSGPKRYDWTGKNWVYSHDGVSLHELLAAELTKALKTKLDLSSL
AYSGKDA

FIG. 13B

MRKKRRQRRRGSDPALLTAAARLLGTKNASCLVLAARHASSGTLGHPGSLDETT
YERLAEETLDSLAEFFEDLADKPYTFEDYDVSFGSGVLTVKLGGDLGTYVINKQT
PNKQIWLSSPSSGPKRYDWTGKNWVYSHDGVSLHELLAAELTKALKTKLDLSSL
AYSGKDA

FIG. 13C

MRKKRRQRRRGSDPQSWSRVYCSLAKRGHFNRISHGLQGLSAVPLRTYASGTLG
HPGSLDETTYERLAEETLDSLAEFFEDLADKPYTFEDYDVSFGSGVLTVKLGGDL
GTYVINKQTPNKQIWLSSPSSGPKRYDWTGKNWVYSHDGVSLHELLAAELTKAL
KTKLDLSSLAYSGKDA

FIG. 13D

MRKKRRQRRRGSDPGALVIRGIRNFNLENRAEREISKMKPSVAPRHPSSGTLGHP
GSLDETTYERLAEETLDSLAEFFEDLADKPYTFEDYDVSFGSGVLTVKLGGDLGT
YVINKQTPNKQIWLSSPSSGPKRYDWTGKNWVYSHDGVSLHELLAAELTKALKT
KLDLSSLAYSGKDA

SEQUENCE LISTING

```
<160> NUMBER OF SEQ ID NOS: 36

<210> SEQ ID NO 1
<211> LENGTH: 27
<212> TYPE: DNA
<213> ORGANISM: Human immunodeficiency virus type 1

<400> SEQUENCE: 1
aggaagaagc ggagacagcg acgaaga                                     27

<210> SEQ ID NO 2
<211> LENGTH: 237
<212> TYPE: DNA
<213> ORGANISM: Homo sapiens

<400> SEQUENCE: 2
tggactctcg ggcgccgcgc agtagccggc ctcctggcgt cacccagccc ggcccaggcc    60
cagaccctca cccgggtccc gcggccggca gagttggccc cactctgcgg ccgccgtggc   120
```
ctgcgcaccg acatcgatgc gacctgcacg ccccgccgcg caagttcgaa ccaacgtggc      180
ctcaaccaga tttggaatgt caaaaagcag agtgtctatt tgatgaattt gaggaaa        237

<210> SEQ ID NO 3
<211> LENGTH: 78
<212> TYPE: DNA
<213> ORGANISM: Homo sapiens

<400> SEQUENCE: 3
gctttactta ctgcggccgc ccggctcttg ggaaccaaga atgcatcttg tcttgttctt      60
gcagcccggc atgccagt                                                   78

<210> SEQ ID NO 4
<211> LENGTH: 102
<212> TYPE: DNA
<213> ORGANISM: Homo sapiens

<400> SEQUENCE: 4
ggagcactag tgattcgcgg tatcaggaat ttcaacctag agaaccgagc ggaacgggaa      60
atcagcaaga tgaagccctc tgtcgctccc agacacccct ct                        102

<210> SEQ ID NO 5
<211> LENGTH: 105
<212> TYPE: DNA
<213> ORGANISM: Homo sapiens

<400> SEQUENCE: 5
cagagctgga gtcgtgtgta ctgctccttg gccaagagag gccatttcaa tcgaatatct     60
catggcctac agggactttc tgcagtgcct ctgagaactt acgca                     105

<210> SEQ ID NO 6
<211> LENGTH: 393
<212> TYPE: DNA
<213> ORGANISM: Homo sapiens

<400> SEQUENCE: 6
tctggaactt tgggccaccc aggctctcta gatgagacca cctatgaaag actagcagag     60
gaaacgctgg actctttagc agagtttttt gaagaccttg cagacaagcc atacacgttt    120
gaggactatg atgtctcctt tgggagtggt gtcttaactg tcaaactggg tggagatcta    180
ggaacctatg tgatcaacaa gcagacgcca aacaagcaaa tctggctatc ttctccatcc    240
agtggaccta gcgttatga ctggactggg aaaaactggg tgtactccca cgacggcgtg    300
tccctccatg agctgctggc cgcagagctc actaaagcct taaaaaccaa actggacttg    360
tcttccttgg cctattccgg aaaagatgct tga                                 393

<210> SEQ ID NO 7
<211> LENGTH: 27
<212> TYPE: DNA
<213> ORGANISM: Artificial Sequence
<220> FEATURE:
<223> OTHER INFORMATION: forward primer for precursor frataxin cloning

<400> SEQUENCE: 7
cgcggatccg tggactctcg ggcgccg                                         27

<210> SEQ ID NO 8
<211> LENGTH: 33
<212> TYPE: DNA
<213> ORGANISM: Artificial Sequence

```
<220> FEATURE:
<223> OTHER INFORMATION: reverse primer for precursor frataxin cloning

<400> SEQUENCE: 8
acgctcgagt caagcatctt ttccggaata ggc                                33

<210> SEQ ID NO 9
<211> LENGTH: 30
<212> TYPE: DNA
<213> ORGANISM: Artificial Sequence
<220> FEATURE:
<223> OTHER INFORMATION: forward primer for MTS lad cloning

<400> SEQUENCE: 9
cgcggatcca cagagctgga gtcgtgtgta                                    30

<210> SEQ ID NO 10
<211> LENGTH: 66
<212> TYPE: DNA
<213> ORGANISM: Artificial Sequence
<220> FEATURE:
<223> OTHER INFORMATION: reverse primer for MTS lad cloning

<400> SEQUENCE: 10
cataggtggt ctcatctaga gagcctgggt ggcccaaagt tccagatgcg taagttctca   60
gaggca                                                              66

<210> SEQ ID NO 11
<211> LENGTH: 28
<212> TYPE: DNA
<213> ORGANISM: Artificial Sequence
<220> FEATURE:
<223> OTHER INFORMATION: forward primer for MTS orf cloning

<400> SEQUENCE: 11
cgcggatccg ggagcactag tgattcgc                                      28

<210> SEQ ID NO 12
<211> LENGTH: 66
<212> TYPE: DNA
<213> ORGANISM: Artificial Sequence
<220> FEATURE:
<223> OTHER INFORMATION: reverse primer for MTS orf cloning

<400> SEQUENCE: 12
cataggtggt ctcatctaga gagcctgggt ggcccaaagt tccagaagag gggtgtctgg   60
gagcga                                                              66

<210> SEQ ID NO 13
<211> LENGTH: 112
<212> TYPE: DNA
<213> ORGANISM: Artificial Sequence
<220> FEATURE:
<223> OTHER INFORMATION: forward oligo for MTS cs cloning

<400> SEQUENCE: 13
gatccggctt tacttactgc ggccgcccgg ctcttgggaa ccaagaatgc atcttgtctt   60
gttcttgcag cccggcatgc cagttctgga actttgggcc acccaggctc tc          112

<210> SEQ ID NO 14
<211> LENGTH: 112
<212> TYPE: DNA
<213> ORGANISM: Artificial Sequence
<220> FEATURE:
```

<223> OTHER INFORMATION: reverse primer for MTS cs cloning

<400> SEQUENCE: 14

```
tctagagagc tgggtggcc caaagttcca gaactggcat gccgggctgc aagaacaaga    60
caagatgcat tcttggttcc caagagccgg gcggccgcag taagtaaagc cg           112
```

<210> SEQ ID NO 15
<211> LENGTH: 957
<212> TYPE: DNA
<213> ORGANISM: Homo sapiens

<400> SEQUENCE: 15

```
ctgaagggcc gtgaccttct cactctaaga aactttaccg gagaagaaat taaatatatg    60
ctatggctat cagcagatct gaaatttagg ataaaacaga aaggagagta tttgccttta   120
ttgcaaggga agtccttagg catgattttt gagaaaagaa gtactcgaac aagattgtct   180
acagaaacag gctttgcact tctgggagga catccttgtt ttcttaccac acaagatatt   240
catttgggtg tgaatgaaag tctcacggac acggccgtg  tattgtctag catggcagat   300
gcagtattgg ctcgagtgta taaacaatca gatttggaca ccctggctaa gaagcatcc    360 atcccaatta tcaatgggct gtcagatttg taccatccta tccagatcct ggctgattac   420
ctcacgctcc aggaacacta tagctctctg aaaggtctta ccctcagctg atcggggat    480 gggaacaata tcctgcactc catcatgatg agcgcagcga aattcggaat gcaccttcag   540
gcagctactc caaagggtta tgagccggat gctagtgtaa ccaagttggc agagcagtat   600
gccaaagaga atggtaccaa gctgttgctg acaaatgatc cattggaagc agcgcatgga   660
ggcaatgtat taattacaga cacttggata agcatgggac aagaagagga gaagaaaaag   720
cggctccagg ctttccaagg ttaccaggtt acaatgaaga ctgctaaagt tgctgcctct   780
gactggacat ttttacactg cttgcccaga aagccagaag aagtggatga tgaagtcttt   840
tattctcctc gatcacactagt gttcccagag gcagaaaaca gaaagtggac aatcatggct   900
gtcatggtgt ccctgctgac agattactca cctcagctcc agaagcctaa attttga      957
```

<210> SEQ ID NO 16
<211> LENGTH: 159
<212> TYPE: DNA
<213> ORGANISM: Homo sapiens

<400> SEQUENCE: 16

```
atgtaccgct acctggccaa agcgctgctg ccgtcccggg ccgggccgc tgccctgggc     60 tccgcggcca accactcggc cgcgttgctg gccggggcc gcggacagcc cgccgccgcc   120
tcgcagccgg ggctcgcatt ggccgcccgg cgccactac                         159
```

<210> SEQ ID NO 17
<211> LENGTH: 190
<212> TYPE: PRT
<213> ORGANISM: Artificial Sequence
<220> FEATURE:
<223> OTHER INFORMATION: His TAT MTS(cs) 81-210 FRA

<400> SEQUENCE: 17

```
Met Gly Ser Ser His His His His His His Ser Ser Gly Leu Val Pro
1               5                   10                  15

Arg Gly Ser His Met Arg Lys Lys Arg Arg Gln Arg Arg Gly Ser
            20                  25                  30

Asp Pro Ala Leu Leu Thr Ala Ala Ala Arg Leu Leu Gly Thr Lys Asn
```

```
            35                  40                  45
Ala Ser Cys Leu Val Leu Ala Ala Arg His Ala Ser Ser Gly Thr Leu
 50                  55                  60
Gly His Pro Gly Ser Leu Asp Glu Thr Thr Tyr Glu Arg Leu Ala Glu
65                  70                  75                  80
Glu Thr Leu Asp Ser Leu Ala Glu Phe Phe Glu Asp Leu Ala Asp Lys
                85                  90                  95
Pro Tyr Thr Phe Glu Asp Tyr Asp Val Ser Phe Gly Ser Gly Val Leu
            100                 105                 110
Thr Val Lys Leu Gly Gly Asp Leu Gly Thr Tyr Val Ile Asn Lys Gln
        115                 120                 125
Thr Pro Asn Lys Gln Ile Trp Leu Ser Ser Pro Ser Ser Gly Pro Lys
    130                 135                 140
Arg Tyr Asp Trp Thr Gly Lys Asn Trp Val Tyr Ser His Asp Gly Val
145                 150                 155                 160
Ser Leu His Glu Leu Leu Ala Ala Glu Leu Thr Lys Ala Leu Lys Thr
                165                 170                 175
Lys Leu Asp Leu Ser Ser Leu Ala Tyr Ser Gly Lys Asp Ala
            180                 185                 190

<210> SEQ ID NO 18
<211> LENGTH: 243
<212> TYPE: PRT
<213> ORGANISM: Artificial Sequence
<220> FEATURE:
<223> OTHER INFORMATION: HTFrataxin [His TAT MTS(fra)81-210 FRA]

<400> SEQUENCE: 18

Met Gly Ser Ser His His His His His His Ser Ser Gly Leu Val Pro
1               5                   10                  15
Arg Gly Ser His Met Arg Lys Lys Arg Arg Gln Arg Arg Arg Gly Ser
            20                  25                  30
Asp Pro Trp Thr Leu Gly Arg Arg Ala Val Ala Gly Leu Leu Ala Ser
        35                  40                  45
Pro Ser Pro Ala Gln Ala Gln Thr Leu Thr Arg Val Pro Arg Pro Ala
    50                  55                  60
Glu Leu Ala Pro Leu Cys Gly Arg Arg Gly Leu Arg Thr Asp Ile Asp
65                  70                  75                  80
Ala Thr Cys Thr Pro Arg Arg Ala Ser Ser Asn Gln Arg Gly Leu Asn
                85                  90                  95
Gln Ile Trp Asn Val Lys Lys Gln Ser Val Tyr Leu Met Asn Leu Arg
            100                 105                 110
Lys Ser Gly Thr Leu Gly His Pro Gly Ser Leu Asp Glu Thr Thr Tyr
        115                 120                 125
Glu Arg Leu Ala Glu Glu Thr Leu Asp Ser Leu Ala Glu Phe Phe Glu
    130                 135                 140
Asp Leu Ala Asp Lys Pro Tyr Thr Phe Glu Asp Tyr Asp Val Ser Phe
145                 150                 155                 160
Gly Ser Gly Val Leu Thr Val Lys Leu Gly Gly Asp Leu Gly Thr Tyr
                165                 170                 175
Val Ile Asn Lys Gln Thr Pro Asn Lys Gln Ile Trp Leu Ser Ser Pro
            180                 185                 190
Ser Ser Gly Pro Lys Arg Tyr Asp Trp Thr Gly Lys Asn Trp Val Tyr
        195                 200                 205
Ser His Asp Gly Val Ser Leu His Glu Leu Leu Ala Ala Glu Leu Thr
```

```
Lys Ala Leu Lys Thr Lys Leu Asp Leu Ser Ser Leu Ala Tyr Ser Gly
225                 230                 235                 240

Lys Asp Ala
```

<210> SEQ ID NO 19
<211> LENGTH: 199
<212> TYPE: PRT
<213> ORGANISM: Artificial Sequence
<220> FEATURE:
<223> OTHER INFORMATION: His TAT MTS(lad) 81-210 FRA

<400> SEQUENCE: 19

```
Met Gly Ser Ser His His His His His Ser Ser Gly Leu Val Pro
1               5                   10                  15

Arg Gly Ser His Met Arg Lys Lys Arg Gln Arg Arg Gly Ser
                20                  25                  30

Asp Pro Gln Ser Trp Ser Arg Val Tyr Cys Ser Leu Ala Lys Arg Gly
            35                  40                  45

His Phe Asn Arg Ile Ser His Gly Leu Gln Gly Leu Ser Ala Val Pro
        50                  55                  60

Leu Arg Thr Tyr Ala Ser Gly Thr Leu Gly His Pro Gly Ser Leu Asp
65                  70                  75                  80

Glu Thr Thr Tyr Glu Arg Leu Ala Glu Thr Leu Asp Ser Leu Ala
                85                  90                  95

Glu Phe Phe Glu Asp Leu Ala Asp Lys Pro Tyr Thr Phe Glu Asp Tyr
            100                 105                 110

Asp Val Ser Phe Gly Ser Gly Val Leu Thr Val Lys Leu Gly Gly Asp
        115                 120                 125

Leu Gly Thr Tyr Val Ile Asn Lys Gln Thr Pro Asn Lys Gln Ile Trp
    130                 135                 140

Leu Ser Ser Pro Ser Ser Gly Pro Lys Arg Tyr Asp Trp Thr Gly Lys
145                 150                 155                 160

Asn Trp Val Tyr Ser His Asp Gly Val Ser Leu His Glu Leu Leu Ala
                165                 170                 175

Ala Glu Leu Thr Lys Ala Leu Lys Thr Lys Leu Asp Leu Ser Ser Leu
            180                 185                 190

Ala Tyr Ser Gly Lys Asp Ala
        195
```

<210> SEQ ID NO 20
<211> LENGTH: 198
<212> TYPE: PRT
<213> ORGANISM: Artificial Sequence
<220> FEATURE:
<223> OTHER INFORMATION: His TAT MTS(orf) 81-210 FRA

<400> SEQUENCE: 20

```
Met Gly Ser Ser His His His His His Ser Ser Gly Leu Val Pro
1               5                   10                  15

Arg Gly Ser His Met Arg Lys Lys Arg Gln Arg Arg Gly Ser
                20                  25                  30

Asp Pro Gly Ala Leu Val Ile Arg Gly Ile Arg Asn Phe Asn Leu Glu
            35                  40                  45

Asn Arg Ala Glu Arg Glu Ile Ser Lys Met Lys Pro Ser Val Ala Pro
        50                  55                  60

Arg His Pro Ser Ser Gly Thr Leu Gly His Pro Gly Ser Leu Asp Glu
```

```
                 65                  70                  75                  80
Thr Thr Tyr Glu Arg Leu Ala Glu Gly Thr Leu Asp Ser Leu Ala Glu
                 85                  90                  95

Phe Phe Glu Asp Leu Ala Asp Lys Pro Tyr Thr Phe Glu Asp Tyr Asp
                100                 105                 110

Val Ser Phe Gly Ser Gly Val Leu Thr Val Lys Leu Gly Gly Asp Leu
                115                 120                 125

Gly Thr Tyr Val Ile Asn Lys Gln Thr Pro Asn Lys Gln Ile Trp Leu
                130                 135                 140

Ser Ser Pro Ser Ser Gly Pro Lys Arg Tyr Asp Trp Thr Gly Lys Asn
145                 150                 155                 160

Trp Val Tyr Ser His Asp Gly Val Ser Leu His Glu Leu Leu Ala Ala
                165                 170                 175

Glu Leu Thr Lys Ala Leu Lys Thr Lys Leu Asp Leu Ser Ser Leu Ala
                180                 185                 190

Tyr Ser Gly Lys Asp Ala
                195

<210> SEQ ID NO 21
<211> LENGTH: 11
<212> TYPE: PRT
<213> ORGANISM: Human immunodeficiency virus type 1

<400> SEQUENCE: 21

Tyr Gly Arg Lys Lys Arg Arg Gln Arg Arg Arg
1               5                   10

<210> SEQ ID NO 22
<211> LENGTH: 79
<212> TYPE: PRT
<213> ORGANISM: Homo sapiens

<400> SEQUENCE: 22

Trp Thr Leu Gly Arg Arg Ala Val Ala Gly Leu Leu Ala Ser Pro Ser
1               5                   10                  15

Pro Ala Gln Ala Gln Thr Leu Thr Arg Val Pro Arg Pro Ala Glu Leu
                20                  25                  30

Ala Pro Leu Cys Gly Arg Arg Gly Leu Arg Thr Asp Ile Asp Ala Thr
                35                  40                  45

Cys Thr Pro Arg Arg Ala Ser Ser Asn Gln Arg Gly Leu Asn Gln Ile
            50                  55                  60

Trp Asn Val Lys Lys Gln Ser Val Tyr Leu Met Asn Leu Arg Lys
65                  70                  75

<210> SEQ ID NO 23
<211> LENGTH: 26
<212> TYPE: PRT
<213> ORGANISM: Homo sapiens

<400> SEQUENCE: 23

Ala Leu Leu Thr Ala Ala Ala Arg Leu Leu Gly Thr Lys Asn Ala Ser
1               5                   10                  15

Cys Leu Val Leu Ala Ala Arg His Ala Ser
                20                  25

<210> SEQ ID NO 24
<211> LENGTH: 35
<212> TYPE: PRT
<213> ORGANISM: Homo sapiens
```

<400> SEQUENCE: 24

Gln Ser Trp Ser Arg Val Tyr Cys Ser Leu Ala Lys Arg Gly His Phe
1               5                   10                  15

Asn Arg Ile Ser His Gly Leu Gln Gly Leu Ser Ala Val Pro Leu Arg
            20                  25                  30

Thr Tyr Ala
        35

<210> SEQ ID NO 25
<211> LENGTH: 34
<212> TYPE: PRT
<213> ORGANISM: Homo sapiens

<400> SEQUENCE: 25

Gly Ala Leu Val Ile Arg Gly Ile Arg Asn Phe Asn Leu Glu Asn Arg
1               5                   10                  15

Ala Glu Arg Glu Ile Ser Lys Met Lys Pro Ser Val Ala Pro Arg His
            20                  25                  30

Pro Ser

<210> SEQ ID NO 26
<211> LENGTH: 130
<212> TYPE: PRT
<213> ORGANISM: Homo sapiens

<400> SEQUENCE: 26

Ser Gly Thr Leu Gly His Pro Gly Ser Leu Asp Glu Thr Thr Tyr Glu
1               5                   10                  15

Arg Leu Ala Glu Glu Thr Leu Asp Ser Leu Ala Glu Phe Phe Glu Asp
            20                  25                  30

Leu Ala Asp Lys Pro Tyr Thr Phe Glu Asp Tyr Asp Val Ser Phe Gly
        35                  40                  45

Ser Gly Val Leu Thr Val Lys Leu Gly Gly Asp Leu Gly Thr Tyr Val
    50                  55                  60

Ile Asn Lys Gln Thr Pro Asn Lys Gln Ile Trp Leu Ser Ser Pro Ser
65                  70                  75                  80

Ser Gly Pro Lys Arg Tyr Asp Trp Thr Gly Lys Asn Trp Val Tyr Ser
                85                  90                  95

His Asp Gly Val Ser Leu His Glu Leu Leu Ala Ala Glu Leu Thr Lys
            100                 105                 110

Ala Leu Lys Thr Lys Leu Asp Leu Ser Ser Leu Ala Tyr Ser Gly Lys
        115                 120                 125

Asp Ala
    130

<210> SEQ ID NO 27
<211> LENGTH: 9
<212> TYPE: PRT
<213> ORGANISM: Human immunodeficiency virus type 1

<400> SEQUENCE: 27

Arg Lys Lys Arg Arg Gln Arg Arg
1               5

<210> SEQ ID NO 28
<211> LENGTH: 170
<212> TYPE: PRT
<213> ORGANISM: Artificial Sequence

```
<220> FEATURE:
<223> OTHER INFORMATION: TAT MTS(cs) 81-210 FRA

<400> SEQUENCE: 28

Met Arg Lys Lys Arg Gln Arg Arg Gly Ser Asp Pro Ala Leu
1               5                   10                  15

Leu Thr Ala Ala Ala Arg Leu Leu Gly Thr Lys Asn Ala Ser Cys Leu
                20                  25                  30

Val Leu Ala Ala Arg His Ala Ser Ser Gly Thr Leu Gly His Pro Gly
            35                  40                  45

Ser Leu Asp Glu Thr Thr Tyr Glu Arg Leu Ala Glu Glu Thr Leu Asp
        50                  55                  60

Ser Leu Ala Glu Phe Phe Glu Asp Leu Ala Asp Lys Pro Tyr Thr Phe
65                  70                  75                  80

Glu Asp Tyr Asp Val Ser Phe Gly Ser Val Leu Thr Val Lys Leu
                85                  90                  95

Gly Gly Asp Leu Gly Thr Tyr Val Ile Asn Lys Gln Thr Pro Asn Lys
            100                 105                 110

Gln Ile Trp Leu Ser Ser Pro Ser Gly Pro Lys Arg Tyr Asp Trp
        115                 120                 125

Thr Gly Lys Asn Trp Val Tyr Ser His Asp Gly Val Ser Leu His Glu
    130                 135                 140

Leu Leu Ala Ala Glu Leu Thr Lys Ala Leu Lys Thr Lys Leu Asp Leu
145                 150                 155                 160

Ser Ser Leu Ala Tyr Ser Gly Lys Asp Ala
                165                 170

<210> SEQ ID NO 29
<211> LENGTH: 223
<212> TYPE: PRT
<213> ORGANISM: Artificial Sequence
<220> FEATURE:
<223> OTHER INFORMATION: TAT MTS(fra)81-210 FRA

<400> SEQUENCE: 29

Met Arg Lys Lys Arg Gln Arg Arg Gly Ser Asp Pro Trp Thr
1               5                   10                  15

Leu Gly Arg Arg Ala Val Ala Gly Leu Leu Ala Ser Pro Ser Pro Ala
                20                  25                  30

Gln Ala Gln Thr Leu Thr Arg Val Pro Arg Pro Ala Glu Leu Ala Pro
            35                  40                  45

Leu Cys Gly Arg Arg Gly Leu Arg Thr Asp Ile Asp Ala Thr Cys Thr
        50                  55                  60

Pro Arg Arg Ala Ser Ser Asn Gln Arg Gly Leu Asn Gln Ile Trp Asn
65                  70                  75                  80

Val Lys Lys Gln Ser Val Tyr Leu Met Asn Leu Arg Lys Ser Gly Thr
                85                  90                  95

Leu Gly His Pro Gly Ser Leu Asp Glu Thr Thr Tyr Glu Arg Leu Ala
            100                 105                 110

Glu Glu Thr Leu Asp Ser Leu Ala Glu Phe Phe Glu Asp Leu Ala Asp
        115                 120                 125

Lys Pro Tyr Thr Phe Glu Asp Tyr Asp Val Ser Phe Gly Ser Gly Val
    130                 135                 140

Leu Thr Val Lys Leu Gly Gly Asp Leu Gly Thr Tyr Val Ile Asn Lys
145                 150                 155                 160

Gln Thr Pro Asn Lys Gln Ile Trp Leu Ser Ser Pro Ser Ser Gly Pro
```

165                 170                 175

Lys Arg Tyr Asp Trp Thr Gly Lys Asn Trp Val Tyr Ser His Asp Gly
            180                 185                 190

Val Ser Leu His Glu Leu Leu Ala Ala Glu Leu Thr Lys Ala Leu Lys
        195                 200                 205

Thr Lys Leu Asp Leu Ser Ser Leu Ala Tyr Ser Gly Lys Asp Ala
    210                 215                 220

<210> SEQ ID NO 30
<211> LENGTH: 179
<212> TYPE: PRT
<213> ORGANISM: Artificial Sequence
<220> FEATURE:
<223> OTHER INFORMATION: TAT MTS(lad) 81-210 FRA

<400> SEQUENCE: 30

Met Arg Lys Lys Arg Arg Gln Arg Arg Gly Ser Asp Pro Gln Ser
1               5                   10                  15

Trp Ser Arg Val Tyr Cys Ser Leu Ala Lys Arg Gly His Phe Asn Arg
            20                  25                  30

Ile Ser His Gly Leu Gln Gly Leu Ser Ala Val Pro Leu Arg Thr Tyr
        35                  40                  45

Ala Ser Gly Thr Leu Gly His Pro Gly Ser Leu Asp Glu Thr Thr Tyr
    50                  55                  60

Glu Arg Leu Ala Glu Glu Thr Leu Asp Ser Leu Ala Glu Phe Phe Glu
65                  70                  75                  80

Asp Leu Ala Asp Lys Pro Tyr Thr Phe Glu Asp Tyr Asp Val Ser Phe
                85                  90                  95

Gly Ser Gly Val Leu Thr Val Lys Leu Gly Gly Asp Leu Gly Thr Tyr
            100                 105                 110

Val Ile Asn Lys Gln Thr Pro Asn Lys Gln Ile Trp Leu Ser Ser Pro
        115                 120                 125

Ser Ser Gly Pro Lys Arg Tyr Asp Trp Thr Gly Lys Asn Trp Val Tyr
    130                 135                 140

Ser His Asp Gly Val Ser Leu His Glu Leu Leu Ala Ala Glu Leu Thr
145                 150                 155                 160

Lys Ala Leu Lys Thr Lys Leu Asp Leu Ser Ser Leu Ala Tyr Ser Gly
                165                 170                 175

Lys Asp Ala

<210> SEQ ID NO 31
<211> LENGTH: 178
<212> TYPE: PRT
<213> ORGANISM: Artificial Sequence
<220> FEATURE:
<223> OTHER INFORMATION: TAT MTS(orf) 81-210 FRA

<400> SEQUENCE: 31

Met Arg Lys Lys Arg Arg Gln Arg Arg Gly Ser Asp Pro Gly Ala
1               5                   10                  15

Leu Val Ile Arg Gly Ile Arg Asn Phe Asn Leu Glu Asn Arg Ala Glu
            20                  25                  30

Arg Glu Ile Ser Lys Met Lys Pro Ser Val Ala Pro Arg His Pro Ser
        35                  40                  45

Ser Gly Thr Leu Gly His Pro Gly Ser Leu Asp Glu Thr Thr Tyr Glu
    50                  55                  60

Arg Leu Ala Glu Glu Thr Leu Asp Ser Leu Ala Glu Phe Phe Glu Asp

```
                65                  70                  75                  80
Leu Ala Asp Lys Pro Tyr Thr Phe Glu Asp Tyr Asp Val Ser Phe Gly
                    85                  90                  95

Ser Gly Val Leu Thr Val Lys Leu Gly Gly Asp Leu Gly Thr Tyr Val
                100                 105                 110

Ile Asn Lys Gln Thr Pro Asn Lys Gln Ile Trp Leu Ser Ser Pro Ser
                115                 120                 125

Ser Gly Pro Lys Arg Tyr Asp Trp Thr Gly Lys Asn Trp Val Tyr Ser
130                 135                 140

His Asp Gly Val Ser Leu His Glu Leu Leu Ala Ala Glu Leu Thr Lys
145                 150                 155                 160

Ala Leu Lys Thr Lys Leu Asp Leu Ser Ser Leu Ala Tyr Ser Gly Lys
                165                 170                 175

Asp Ala

<210> SEQ ID NO 32
<211> LENGTH: 4
<212> TYPE: PRT
<213> ORGANISM: Artificial Sequence
<220> FEATURE:
<223> OTHER INFORMATION: linker

<400> SEQUENCE: 32

Gly Ser Asp Pro
1

<210> SEQ ID NO 33
<211> LENGTH: 166
<212> TYPE: PRT
<213> ORGANISM: Artificial Sequence
<220> FEATURE:
<223> OTHER INFORMATION: TAT MTS(cs) 81-210 FRA delta linker

<400> SEQUENCE: 33

Met Arg Lys Lys Arg Gln Arg Arg Arg Ala Leu Leu Thr Ala Ala
1               5                   10                  15

Ala Arg Leu Leu Gly Thr Lys Asn Ala Ser Cys Leu Val Leu Ala Ala
                20                  25                  30

Arg His Ala Ser Ser Gly Thr Leu Gly His Pro Gly Ser Leu Asp Glu
            35                  40                  45

Thr Thr Tyr Glu Arg Leu Ala Glu Glu Thr Leu Asp Ser Leu Ala Glu
        50                  55                  60

Phe Phe Glu Asp Leu Ala Asp Lys Pro Tyr Thr Phe Glu Asp Tyr Asp
65                  70                  75                  80

Val Ser Phe Gly Ser Gly Val Leu Thr Val Lys Leu Gly Gly Asp Leu
                85                  90                  95

Gly Thr Tyr Val Ile Asn Lys Gln Thr Pro Asn Lys Gln Ile Trp Leu
                100                 105                 110

Ser Ser Pro Ser Ser Gly Pro Lys Arg Tyr Asp Trp Thr Gly Lys Asn
            115                 120                 125

Trp Val Tyr Ser His Asp Gly Val Ser Leu His Glu Leu Leu Ala Ala
        130                 135                 140

Glu Leu Thr Lys Ala Leu Lys Thr Lys Leu Asp Leu Ser Ser Leu Ala
145                 150                 155                 160

Tyr Ser Gly Lys Asp Ala
                165
```

```
<210> SEQ ID NO 34
<211> LENGTH: 219
<212> TYPE: PRT
<213> ORGANISM: Artificial Sequence
<220> FEATURE:
<223> OTHER INFORMATION: TAT MTS(fra)81-210 FRA delta linker

<400> SEQUENCE: 34
```

Met Arg Lys Lys Arg Gln Arg Arg Trp Thr Leu Gly Arg Arg
1               5                   10                  15

Ala Val Ala Gly Leu Leu Ala Ser Pro Ser Ala Gln Ala Gln Thr
                20                  25                  30

Leu Thr Arg Val Pro Arg Pro Ala Glu Leu Ala Pro Leu Cys Gly Arg
            35                  40                  45

Arg Gly Leu Arg Thr Asp Ile Asp Ala Thr Cys Thr Pro Arg Arg Ala
        50                  55                  60

Ser Ser Asn Gln Arg Gly Leu Asn Gln Ile Trp Asn Val Lys Lys Gln
65                  70                  75                  80

Ser Val Tyr Leu Met Asn Leu Arg Lys Ser Gly Thr Leu Gly His Pro
                85                  90                  95

Gly Ser Leu Asp Glu Thr Thr Tyr Glu Arg Leu Ala Glu Glu Thr Leu
            100                 105                 110

Asp Ser Leu Ala Glu Phe Phe Glu Asp Leu Ala Asp Lys Pro Tyr Thr
        115                 120                 125

Phe Glu Asp Tyr Asp Val Ser Phe Gly Ser Gly Val Leu Thr Val Lys
    130                 135                 140

Leu Gly Gly Asp Leu Gly Thr Tyr Val Ile Asn Lys Gln Thr Pro Asn
145                 150                 155                 160

Lys Gln Ile Trp Leu Ser Ser Pro Ser Ser Gly Pro Lys Arg Tyr Asp
                165                 170                 175

Trp Thr Gly Lys Asn Trp Val Tyr Ser His Asp Gly Val Ser Leu His
            180                 185                 190

Glu Leu Leu Ala Ala Glu Leu Thr Lys Ala Leu Lys Thr Lys Leu Asp
        195                 200                 205

Leu Ser Ser Leu Ala Tyr Ser Gly Lys Asp Ala
    210                 215

```
<210> SEQ ID NO 35
<211> LENGTH: 175
<212> TYPE: PRT
<213> ORGANISM: Artificial Sequence
<220> FEATURE:
<223> OTHER INFORMATION: TAT MTS(lad) 81-210 FRA delta linker

<400> SEQUENCE: 35
```

Met Arg Lys Lys Arg Gln Arg Arg Gln Ser Trp Ser Arg Val
1               5                   10                  15

Tyr Cys Ser Leu Ala Lys Arg Gly His Phe Asn Arg Ile Ser His Gly
                20                  25                  30

Leu Gln Gly Leu Ser Ala Val Pro Leu Arg Thr Tyr Ala Ser Gly Thr
            35                  40                  45

Leu Gly His Pro Gly Ser Leu Asp Glu Thr Thr Tyr Glu Arg Leu Ala
        50                  55                  60

Glu Glu Thr Leu Asp Ser Leu Ala Glu Phe Phe Glu Asp Leu Ala Asp
65                  70                  75                  80

Lys Pro Tyr Thr Phe Glu Asp Tyr Asp Val Ser Phe Gly Ser Gly Val
                85                  90                  95

```
Leu Thr Val Lys Leu Gly Gly Asp Leu Gly Thr Tyr Val Ile Asn Lys
            100                 105                 110

Gln Thr Pro Asn Lys Gln Ile Trp Leu Ser Ser Pro Ser Ser Gly Pro
            115                 120                 125

Lys Arg Tyr Asp Trp Thr Gly Lys Asn Trp Val Tyr Ser His Asp Gly
            130                 135                 140

Val Ser Leu His Glu Leu Leu Ala Ala Glu Leu Thr Lys Ala Leu Lys
145                 150                 155                 160

Thr Lys Leu Asp Leu Ser Ser Leu Ala Tyr Ser Gly Lys Asp Ala
                165                 170                 175

<210> SEQ ID NO 36
<211> LENGTH: 174
<212> TYPE: PRT
<213> ORGANISM: Artificial Sequence
<220> FEATURE:
<223> OTHER INFORMATION: TAT MTS(orf) 81-210 FRA delta linker

<400> SEQUENCE: 36

Met Arg Lys Lys Arg Arg Gln Arg Arg Arg Gly Ala Leu Val Ile Arg
1               5                   10                  15

Gly Ile Arg Asn Phe Asn Leu Glu Asn Arg Ala Glu Arg Glu Ile Ser
            20                  25                  30

Lys Met Lys Pro Ser Val Ala Pro Arg His Pro Ser Ser Gly Thr Leu
            35                  40                  45

Gly His Pro Gly Ser Leu Asp Glu Thr Thr Tyr Glu Arg Leu Ala Glu
        50                  55                  60

Glu Thr Leu Asp Ser Leu Ala Glu Phe Phe Glu Asp Leu Ala Asp Lys
65                  70                  75                  80

Pro Tyr Thr Phe Glu Asp Tyr Asp Val Ser Phe Gly Ser Gly Val Leu
                85                  90                  95

Thr Val Lys Leu Gly Gly Asp Leu Gly Thr Tyr Val Ile Asn Lys Gln
            100                 105                 110

Thr Pro Asn Lys Gln Ile Trp Leu Ser Ser Pro Ser Ser Gly Pro Lys
            115                 120                 125

Arg Tyr Asp Trp Thr Gly Lys Asn Trp Val Tyr Ser His Asp Gly Val
        130                 135                 140

Ser Leu His Glu Leu Leu Ala Ala Glu Leu Thr Lys Ala Leu Lys Thr
145                 150                 155                 160

Lys Leu Asp Leu Ser Ser Leu Ala Tyr Ser Gly Lys Asp Ala
                165                 170
```

MITOCHONDRIAL PROTEINS CONSTRUCTS AND USES THEREOF

RELATED APPLICATIONS

This application claims priority to and benefit of provisional applications U.S. Ser. No. 61/811,934 filed on Apr. 15, 2013 and U.S. Ser. No. 61/869,981 filed Aug. 26, 2013, the contents of which are herein incorporated by reference in their entireties.

INCORPORATION-BY-REFERENCE OF SEQUENCE LISTING

The contents of the text file named "46256-501001US_ST25.txt", which was created on Dec. 16, 2013 and is 30 KB in size, is hereby incorporated by reference in their entirety.

FIELD OF THE INVENTION

Disclosed are novel fusion protein constructs comprising a functional mitochondrial protein. Further disclosed are methods of treating mitochondrial disorders by the fusion proteins and compositions therefor.

BACKGROUND OF THE INVENTION

Mitochondria play a major and critical role in cellular homeostasis—they participate in intracellular signaling, apoptosis and perform numerous biochemical tasks, such as pyruvate oxidation, the citric acid cycle (also referred to as the Krebs cycle), and metabolism of amino acids, fatty acids, nucleotides and steroids. However, the most crucial task of mitochondria is their role in cellular energy metabolism. This includes β-oxidation of fatty acids and production of ATP by means of the electron-transport chain and the oxidative-phosphorylation system [1, 2].

Most of the approximately 900 gene products in the mitochondria are encoded by nuclear DNA (nDNA) where mitochondrial DNA (mtDNA) only contains 13 protein encoding genes. Most of the polypeptides encoded by nDNA genes are synthesized with a mitochondrial targeting sequence (MTS), allowing their import from the cytoplasm into mitochondria through the translocation machinery (TOM/TIM). Upon entering the mitochondria, the MTS is recognized and cleaved off, allowing for proper processing and, if necessary, assembly into mitochondrial enzymatic complexes [3].

Currently, there is no cure for genetic mitochondrial metabolic disorders and treatment is mostly palliative.

Enzyme or Protein Replacement Therapy (E/PRT) is a therapeutic approach for metabolic disorders, whereby the deficient or absent protein/enzyme is artificially manufactured, purified and administered intravenously to the patient in need thereof on a regular basis.

After many years of extensive research, E/PRT has been successfully accepted as the treatment of choice for metabolic lysosomal storage diseases, including Gaucher disease, Fabry disease and attenuated variants of mucopolysaccaridoses type 1 (MPS 1). However, the inability of the intravenously administered enzymes to penetrate the blood-brain barrier severely limits the application of this approach for the treatment of other metabolic disorders that involve the central nervous system (CNS) [4, 5].

One approach for delivering proteins into cells is their fusion with protein transduction domains (PTDs), a group of short peptides that serve as delivery vectors for large molecules. Generally, PTDs are defined as short, water-soluble and partly hydrophobic, and/or polybasic peptides (at most 30-35 amino acids residues) with a net positive charge at physiological pH [6, 7]. The main feature of PTDs is that they are able to penetrate the cell membrane at low micromolar concentrations both in vitro and in vivo without using any chiral receptors and without causing significant membrane damage. Furthermore, and even more importantly, these peptides are capable of internalizing electrostatically or covalently bound biologically active cargoes (such as drugs) with high efficiency and with low toxicity. The mechanism(s) by which PTDs enter the cells has not been completely understood. One of the well-characterized PTDs is the transactivator of transcription (TAT) peptide originating from the HIV-1 virus. TAT is an 11-amino-acid (residues 47-57) arginine- and lysine-rich portion of the Tat protein encoded by HIV-1 virus [8, 9]. TAT-fusion proteins have been previously shown to be rapidly and efficiently introduced into cultured cells, intact tissue and live tissues when injected into mice [10-12]. It has also been demonstrated that TAT fusion proteins traverse mitochondrial membranes [13, WO 2009/098682].

There has been great progress in the use of PTD-fusion proteins for the delivery of different macromolecules into cells both in vitro and in vivo. This system can be used even for the delivery of cargoes into the brain across the blood-brain barrier. In addition, the ability to target specific intracellular sub-localizations, such as the nuclei, the mitochondria and lysosomes, further expands the possibilities of this delivery system to the development of sub-cellular organelle-targeted therapy. The therapeutic applications seem almost unlimited, and the use of the TAT-based delivery system has extended from proteins to a large variety of cargoes such as oligonucleotides, imaging agents, low molecular mass drugs, nanoparticles, micelles and liposomes. As will be shown, this PTD system is used for developing fusion constructs of functional mitochondrial proteins, for treatment of mitochondrial disorders, for example Friedreich ataxia.

Friedreich ataxia is an autosomal recessive degenerative disorder characterized by ataxia, areflexia, sensory loss, weakness, scoliosis, and cardiomyopathy. Diabetes mellitus, optic neuropathy, and hearing loss are also seen in patients suffering from this disease [14, 15]. Most patients with Friedreich ataxia (97%) have expansions of a GAA repeat in the first intron on both alleles of the gene encoding the mitochondrial protein frataxin [15, 16] whose expression is reduced in Friedreich ataxia [17]. The size of the GAA repeat expansion inversely correlates with frataxin expression and with the age of disease onset [16]. A deficiency of frataxin in cells leads to decreased activities of mitochondrial iron-sulfur cluster-containing enzymes, to an accumulation of iron in the mitochondrial matrix, increased sensitivity to oxidative stress, as well as to impaired adenosine triphosphate (ATP) production [18-20]. Current targets for disease-modifying drug development include agents targeting the mitochondria, aimed to (1) reduce oxidative stress and free-radical generation; (2) improve ATP production; (3) reduce iron accumulation; and (4) increase frataxin production and the assembly of iron-sulfur clusters [21]. There are presently 21 agents or classes of therapeutic agents enrolled in the research pipeline of Friedreich ataxia disease (www_curefa_org/pipeline_html). Millions of dollars from public, private, and industry-based initiatives have been dedicated to research of Friedreich ataxia therapeutics. Despite this vigorous international effort, there is as yet no proven disease-modifying therapy for Friedreich ataxia [22].

Development of E/PRT using the TAT delivery system in mitochondrial disorders was previously reported for lipoamide dehydrogenase (LAD) mitochondrial deficiency [23 and WO 2009/098682]. LAD is the E3 subunit of the three α-ketoacid dehydrogenase complexes in the mitochondrial matrix, which are crucial for the metabolism of carbohydrates and amino acids. These complexes are the pyruvate dehydrogenase complex (PDHC), the α-ketoglutarate dehydrogenase complex (KGDHC) and the branched chain ketoacid dehydrogenase complex (BCKDHC). This previously reported TAT delivery system was based on a TAT-LAD fusion protein comprising the natural precursor sequence of the human LAD containing the N-terminal 35 amino acid mitochondrial targeting sequence (MTS). The natural MTS of LAD was used to facilitate processing of the TAT-LAD construct upon delivery into the mitochondria, thus allowing the incorporation of the delivered LAD into the α-ketoacid dehydrogenase complexes. This TAT-LAD construct was demonstrated to enter patients' cells rapidly, and efficiently reaching the mitochondria. Inside the mitochondria, TAT-LAD was shown to be processed and to restore LAD activity [23]. Moreover, delivery of TAT-LAD into E3-deficient mice tissues was also demonstrated [24]. In mice tissues, a single administration of TAT-LAD resulted in a significant increase in the enzymatic activity of the mitochondrial multienzyme complex pyruvate-dehydrogenase complex within the liver, heart and, most importantly, brain of TAT-LAD-treated E3-deficient mice [24].

Notably, TAT-LAD was shown to be able to restore the activity of the pyruvate dehydrogenase complex (PDHC) within treated patients' cells almost back to its normal levels. PDHC is a $9.5 \times 10^6$ Da macromolecular machine whose multipart structure assembly process involves numerous different subunits: a pentagonal core of 60 units of the E2 component (dihydrolipoamide), attached to 30 tetramers of the E1 component (α2β2) (pyruvate decarboxylase), 12 dimers of the E3 (LAD, dihydrolipoamide) component and 12 units of the E3 binding protein. The structure of all α-ketoacid dehydrogenase complexes is similar to that of PDHC. The complexity of this structure emphasizes the significance in showing that TAT-mediated replacement of one mutated component restores the activity of an essential mitochondrial multi-component enzymatic complex in cells of enzyme-deficient patients.

Previous studies of mitochondria delivery system primarily used the native MTS of mitochondrial proteins (e.g. LAD) and showed that the native MTS was necessary for maximal restoration of LAD enzymatic function. Deleting the MTS restored a significantly smaller amount of LAD activity within the mitochondria. Since TAT can move both ways across a membrane and thus pull the therapeutic cargo out of the mitochondria, when MTS is included, the matrix processing peptidases recognizes the sequence and clips it, and the cargo (e.g. mature LAD) is left in the mitochondrial matrix while the TAT peptide can transduce out of the mitochondrion. Repeated dosing should therefore result in accumulating amounts of cargo in the mitochondria over time.

A TAT-FRATAXIN (TAT-FXN) fusion protein for putative treatment of Friedreich's ataxia was recently reported [25]. This TAT-FXN fusion protein was shown to bind iron in vitro, transduce into the mitochondria of Friedreich ataxia deficient fibroblasts and also reduce caspase-3 activation in response to an exogenous iron-oxidant stress. In this TAT-FXN fusion protein, the authors used the native MTS of frataxin that consists of 80 amino acid residues (aa) for preparing their TAT-FXN fusion protein [26].

It is known that FXN mRNA is translated to a precursor polypeptide that is transported to the mitochondrial matrix and processed to at least two forms, namely FXN42-210 and FXN81-210. FXN42-210 is a transient processing intermediate, whereas FXN81-210 represents the mature protein [27, 28]. However, it was found that both FXN42-210 and FXN8-210 are present in control cell lines and tissues at steady-state, and that FXN42-210 is consistently more depleted than FXN81-210 in samples from Friedreich's ataxia patients [29].

Most nuclear-encoded mitochondrial proteins contain a cleavable N-terminal MTS that directs mitochondrial targeting of the protein; as detailed above, the N-terminal MTS is cleaved off by matrix processing proteases at a well-conserved RXY↓(S/A) motif, which is a three amino acid (aa) motif, where X can be any aa, followed by serine or alanine and cleavage is performed after the three first amino acids [26, 30-31]. These N-terminal MTSs are typically 15-30 amino acids in length including 3-5 nonconsecutive basic amino acid (arginine/lysine) residues, often with several serine/threonine residues but without acidic amino acid (asparate/glutamate) residues. In their molecular structure, these MTSs are able to form strong basic amphipathic α-helices that are essential for efficient mitochondrial transportation [32]. Thus, by way of example, the long 80-aa native MTS of frataxin as well as its two-step processing can reduce its efficiency in the delivery of cargos into the matrix of the mitochondria.

SUMMARY OF THE INVENTION

Provided is a fusion protein comprising a HIV-1 transactivator of transcription (TAT) domain, a functional human mitochondrial protein and a human mitochondria targeting sequence (MTS) situated between said TAT domain and said functional mitochondrial protein and wherein said human MTS is heterologous to said functional protein.

In the disclosed fusion protein said human mitochondrial protein can be a functional mitochondrial protein per se and/or a component of a mitochondrial multi-component complex, for example human frataxin and ornithine transcarbamoylase (OTC).

In the disclosed fusion protein, said MTS can comprise from about 15 to about 40 amino acid residues, including from about 3 to about 5 nonconsecutive basic amino acid residues, and optionally from about 1 to about 3 or 4 or 5 serine/threonine residues.

Non-limiting examples of the MTS comprised in the disclosed fusion protein are any one of human lipoamide dehydrogenase MTS (the amino acid and the nucleic acid sequence encoding therefor are denoted by SEQ ID NO: 24 and SEQ ID NO: 5, respectively), the MTS of the human C6ORF66 gene product (the amino acid and the nucleic acid sequence encoding therefor are denoted by SEQ ID NO: 25 and SEQ ID NO: 4, respectively), the human mitochondrial citrate synthase MTS (the amino acid and the nucleic acid sequence encoding therefor are denoted by SEQ ID NO: 23 and SEQ ID NO: 3, respectively), and the MTS of human mitochondrial GLUD2 (encoded by the nucleic acid sequence denoted by SEQ ID NO: 16).

Further provided is a fusion protein comprising a HIV-1 transactivator of transcription (TAT) domain fused to human frataxin and a human mitochondria targeting sequence (MTS) of a human mitochondrial protein selected from lipoamide dehydrogenase (LAD) and citrate synthase (CS) situated between said TAT domain and said frataxin, wherein said frataxin is C-terminal to said MTS of human lipoamide dehydrogenase or human citrate synthase.

The disclosed fusion protein as herein defined may further comprise a linker covalently linking said TAT domain to said MTS sequence.

In the disclosed fusion protein, the fusion protein may have the amino acid sequence denoted by SEQ ID NO: 30, comprising a HIV-1 transactivator of transcription (TAT) domain having the amino acid sequence denoted by SEQ ID NO: 27 fused to human frataxin having the amino acid sequence denoted by SEQ ID NO: 26 and a mitochondria targeting sequence (MTS) of human lipoamide dehydrogenase having the amino acid sequence denoted by SEQ ID NO: 24, said MTS situated between said TAT domain and said frataxin, and is linked to said TAT domain via a linker having the amino acid sequence denoted by SEQ ID NO: 32, and wherein said frataxin is C-terminal to said MTS of human lipoamide dehydrogenase.

In further embodiments of the disclosed fusion protein, the fusion protein may have the amino acid sequence denoted by SEQ ID NO: 28, comprising a HIV-1 transactivator of transcription (TAT) domain having the amino acid sequence denoted by SEQ ID NO: 27 fused to human frataxin having the amino acid sequence denoted by SEQ ID NO: 26 and a mitochondria targeting sequence (MTS) of human citrate synthase having the amino acid sequence denoted by SEQ ID NO: 23, said MTS situated between said TAT domain and said frataxin, and is linked to said TAT domain via a linker having the amino acid sequence denoted by SEQ ID NO: 32, and wherein said frataxin is C-terminal to said MTS of human citrate synthase.

Further disclosed is a composition comprising a physiologically acceptable carrier and as an active ingredient a fusion protein as disclosed herein, and a pharmaceutical composition comprising a pharmaceutically acceptable carrier and as an active ingredient a fusion protein as disclosed herein.

Further disclosed is a composition comprising a physiologically acceptable carrier and as an active ingredient a fusion protein comprising a HIV-1 transactivator of transcription (TAT) domain fused to human frataxin and a human mitochondria targeting sequence (MTS) of a human mitochondrial protein selected from lipoamide dehydrogenase (LAD) and citrate synthase (CS) situated between said TAT domain and said frataxin, wherein said frataxin is C-terminal to said MTS of human lipoamide dehydrogenase or human citrate synthase, as disclosed herein.

The present disclosure further provides a composition comprising as an active ingredient a fusion protein having the amino acid sequence denoted by SEQ ID NO: 30 or a fusion protein having the amino acid sequence denoted by SEQ ID NO: 28 and a physiologically acceptable carrier.

The pharmaceutical composition disclosed herein can be intended for treating or alleviating a mitochondrial disorder, such as but not limited to Friedreich's ataxia or any other disorder associated with deficiency of frataxin or defective frataxin or a disorder associated with a deficiency of OTC or with defective OTC.

Further disclosed is a pharmaceutical composition comprising a physiologically acceptable carrier and as an active ingredient a fusion protein as disclosed herein, and a pharmaceutical composition comprising a pharmaceutically acceptable carrier and as an active ingredient a fusion protein as disclosed herein.

Further disclosed is a pharmaceutical composition for the treatment of Friedrich's Ataxia by intravenous administration to a subject in need thereof, said composition comprising a therapeutically effective amount of a fusion protein having the amino acid sequence denoted by SEQ ID NO: 30 or a fusion protein having the amino acid sequence denoted by SEQ ID NO: 28 and at least one of pharmaceutically acceptable carrier, diluent, additive and excipient.

A non-limiting example of a pharmaceutical composition as herein defined is wherein the therapeutically effective amount administered is from about 0.5 mg/Kg to about 2 mg/Kg body weight of the subject.

Thus, the disclosed fusion protein can be used in a method for the treatment of a mitochondrial disorder, such as but not limited to Friedreich's ataxia or any other disorder associated with deficiency of frataxin or defective frataxin or, respectively a disorder associated with a deficiency of OTC or with defective OTC.

Further provided is a method for treating or alleviating a mitochondrial disorder, said method comprising the step of administering to a subject in need of such treatment a therapeutically effective amount of the fusion protein disclosed herein, thereby treating a mitochondria disorder.

In some embodiments of the disclosed method, the functional protein is frataxin, respectively OTC, and the mitochondrial disorder is Friedreich's ataxia or any other disorder associated with deficiency of frataxin or defective frataxin or, respectively, a disorder associated with a deficiency of OTC or with defective OTC.

The disclosed method for treating or alleviating a mitochondrial disorder can further comprises administering an additional therapeutic agent.

Further provided is a method for introducing a functional mitochondrial protein into mitochondria of a subject, said method comprising the step of administering to a subject in need of such treatment a therapeutically effective amount of the fusion protein as disclosed herein, thereby introducing a functional mitochondrial protein into the mitochondria of a subject in need thereof.

Still further, provided is a method for alleviating oxidative stress in a subject in need thereof, said method comprising the step of administering to a subject in need of such treatment a therapeutically effective amount of the fusion protein as disclosed herein, thereby alleviating oxidative stress in said subject.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 1A, 1B, 1C, and 1D: Schematic Structures of the Various TAT-MTS-FRA Fusion Proteins and the Expected Molecular Weights Thereof Abbreviations: H, His tag; FRA (or fra), Frataxin; MTS, mitochondrial translocation sequence; cs, Citrate synthase; orf, C6ORF66; and lad, LAD.

FIGS. 2A, 2B, 2C, and 2D: Expression and Sub-Cellular Localization of TAT-MTSfra-FRA and of TAT-MTSorf-FRA Fusion Proteins FIG. 2 presents an image of SDS-PAGE analysis of bacterial sub-fractions expressing the TAT-MTSfra-FRA fusion protein (FIG. 2A) and an immunoblot of Western blot analysis thereof (FIG. 2B) using anti-His antibody; FIG. 2C presents an image of SDS-PAGE analysis of bacterial sub-fractions expressing TAT-MTSorf-FRA fusion protein and an immunoblot of Western blot analysis thereof using anti-His antibody is presented in FIG. 2D.

Abbreviations: 1, whole cell extract; 2, soluble fraction; 3, insoluble fraction; KDa, kilo Dalton; and M=marker. Arrow heads indicate the fusion proteins.

Figure 3D:
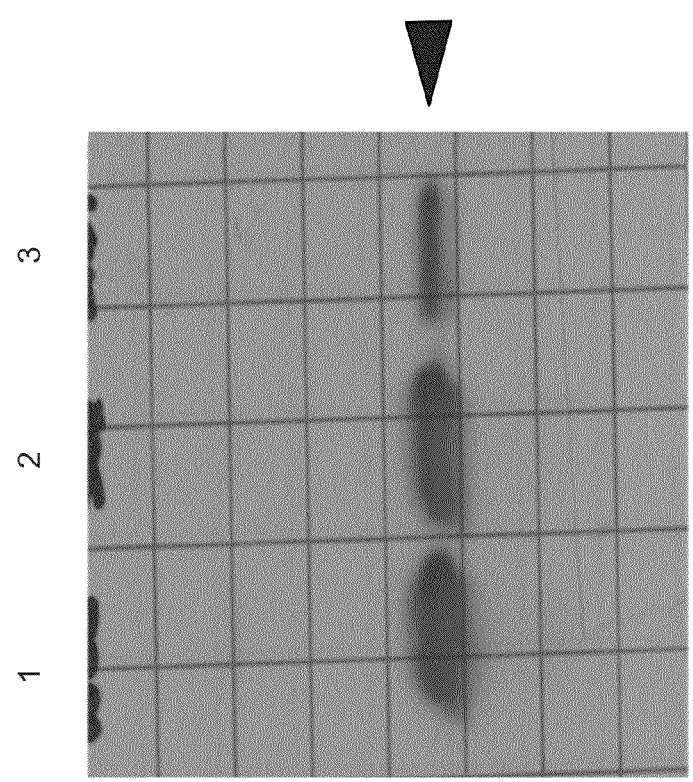
Figure 3C:
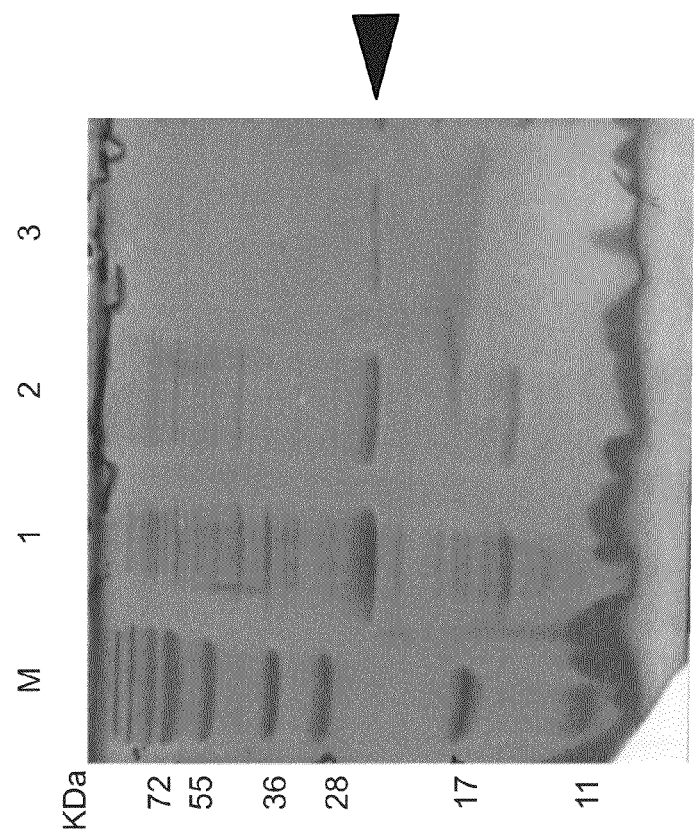
Figure 4A:
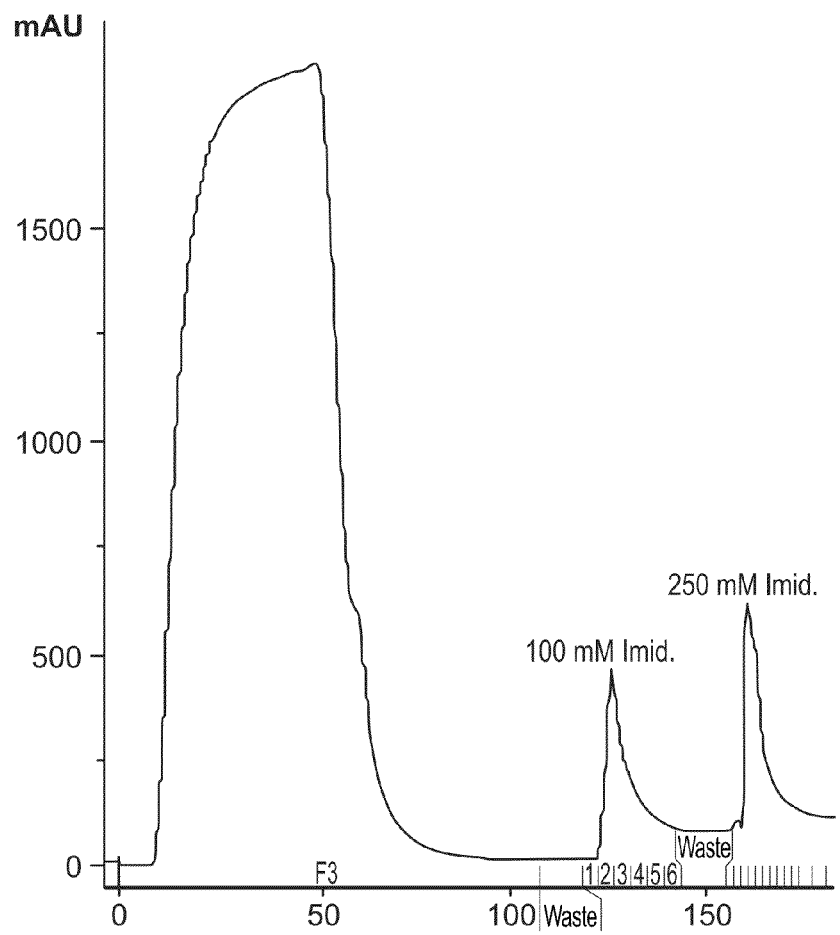
Figure 4B:
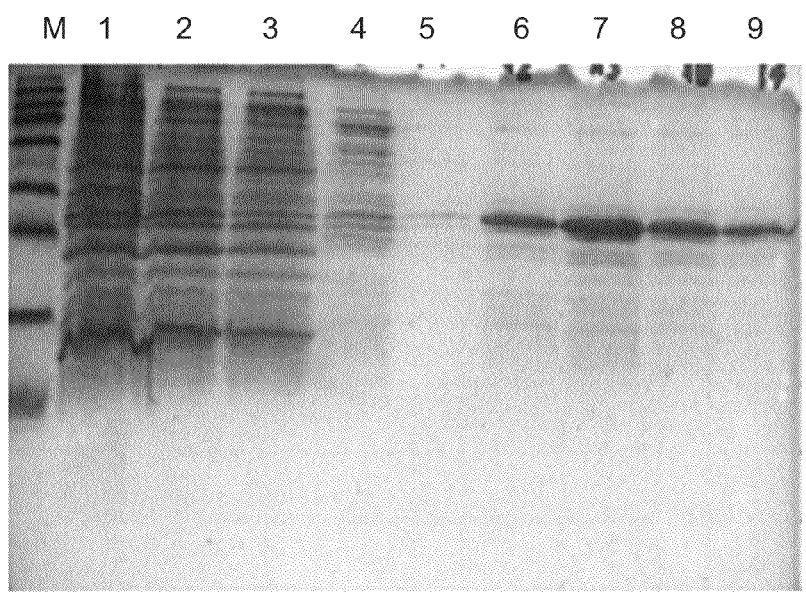
Figure 4C:
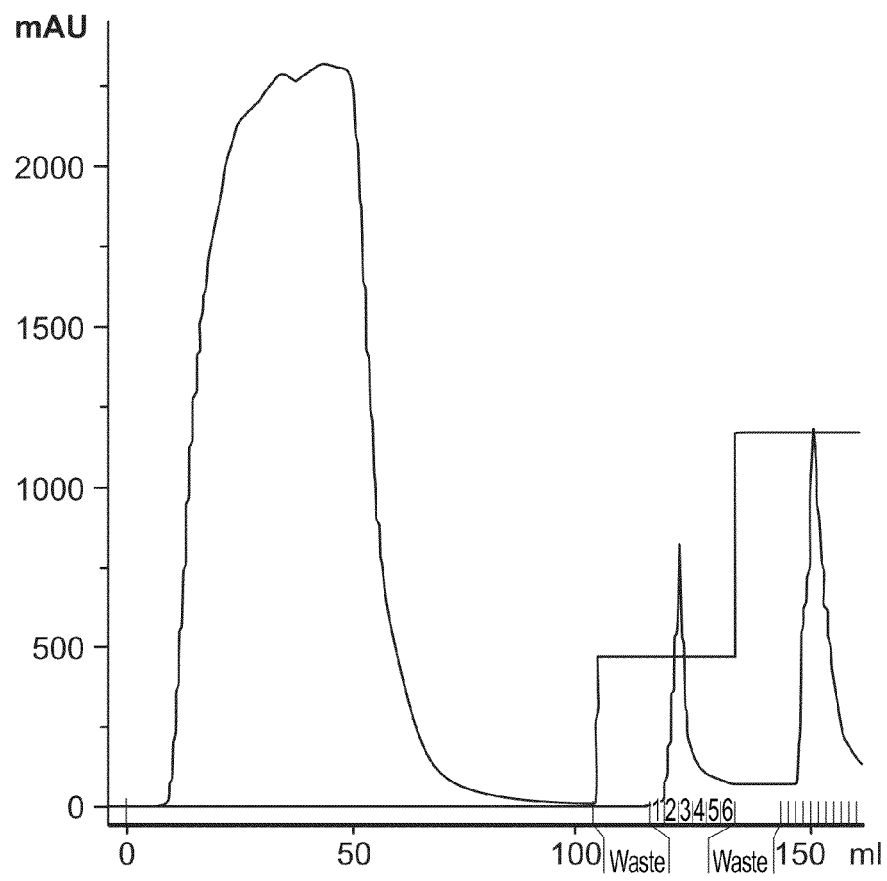
Figure 4D:
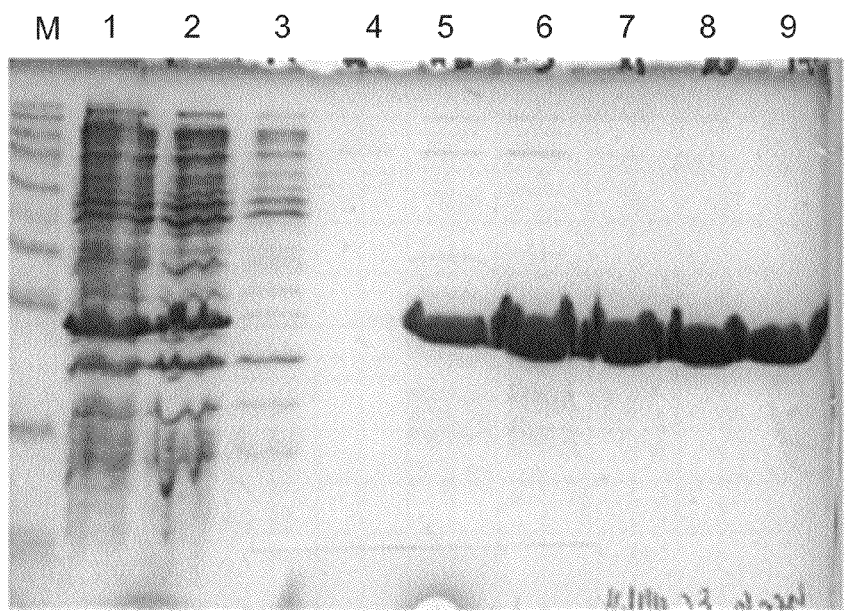
Figure 5A:
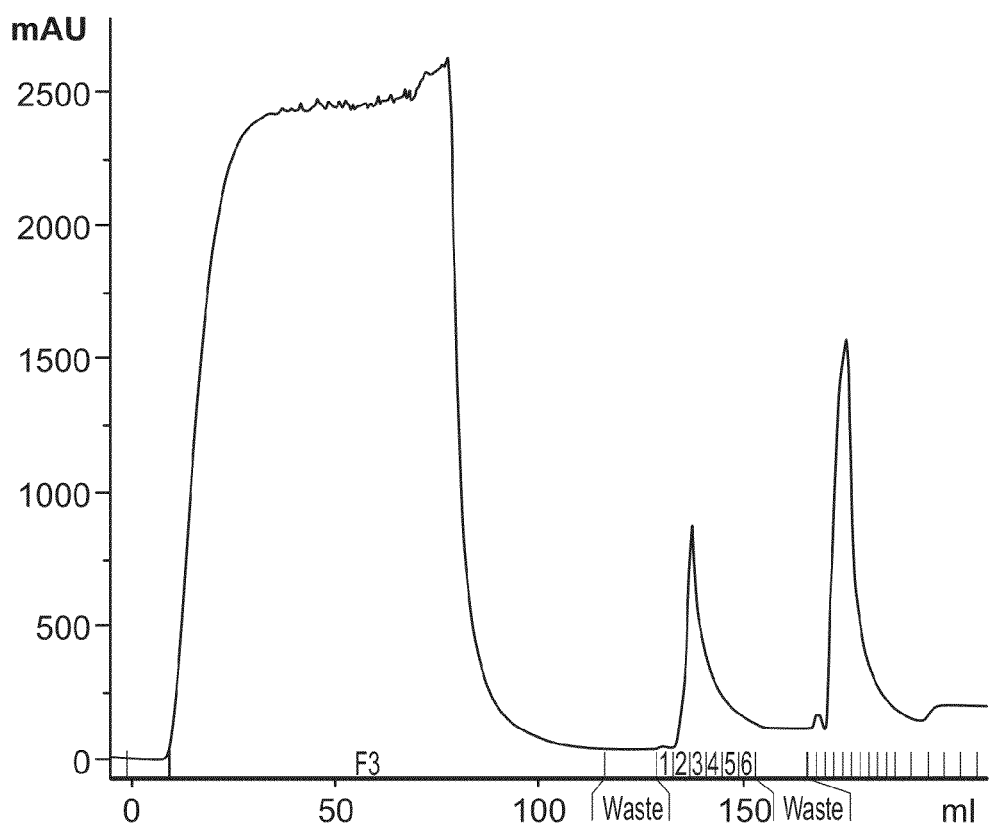
Figure 5B:
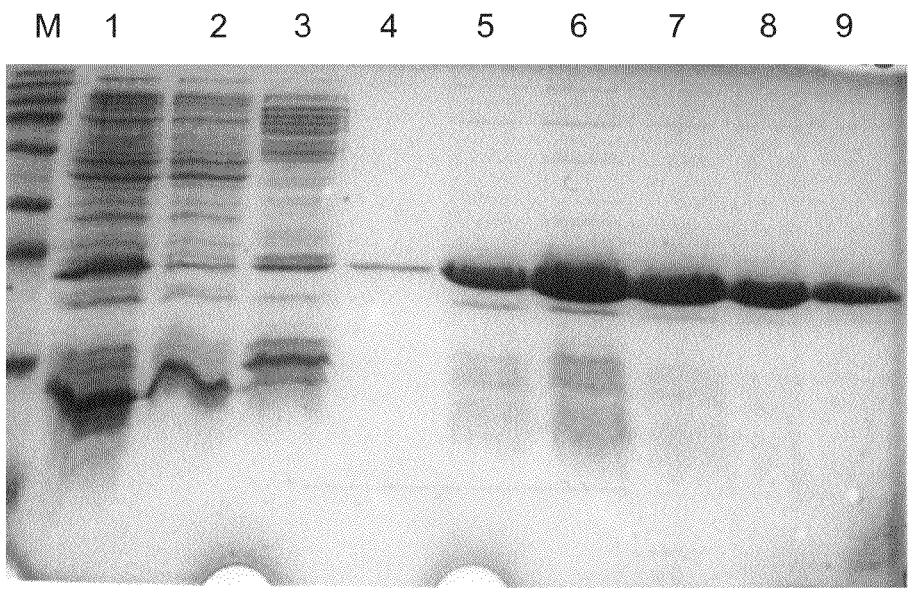
Figure 5C:
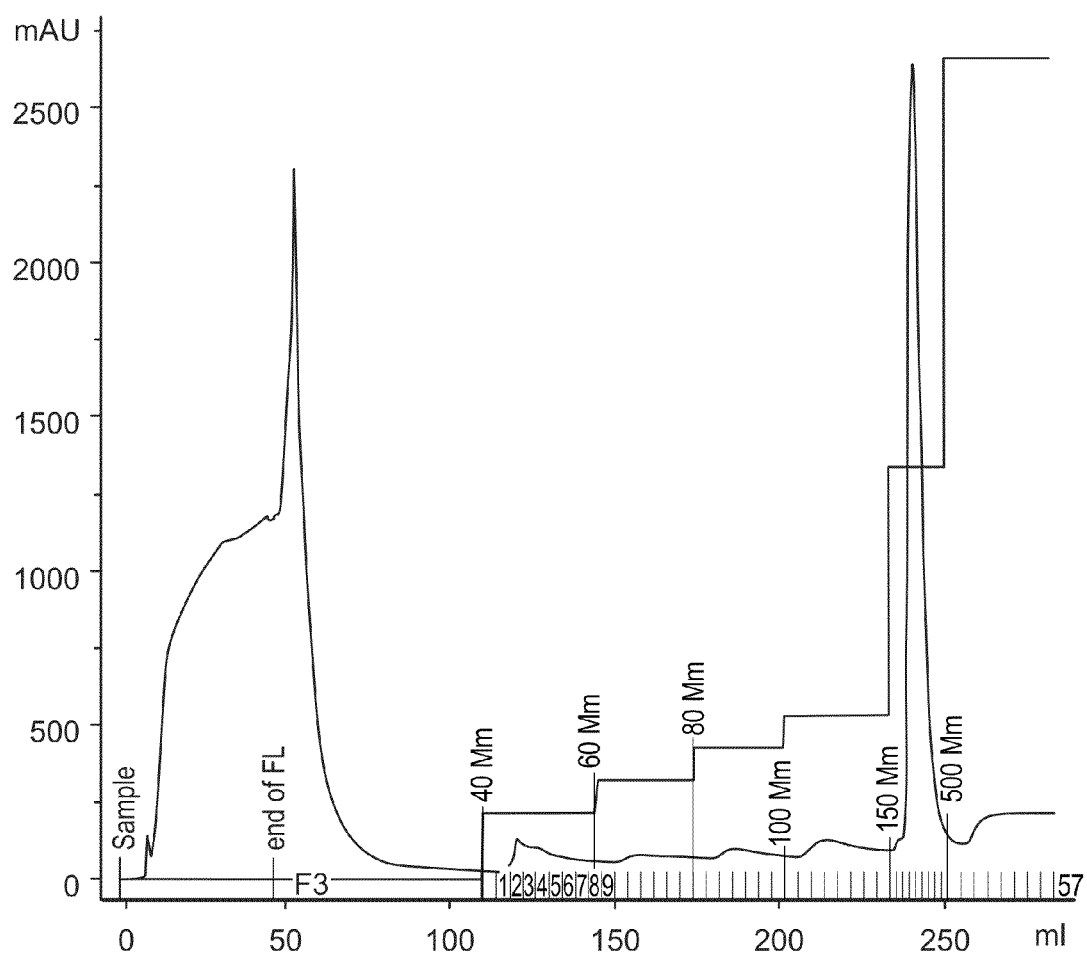
Figure 5D:
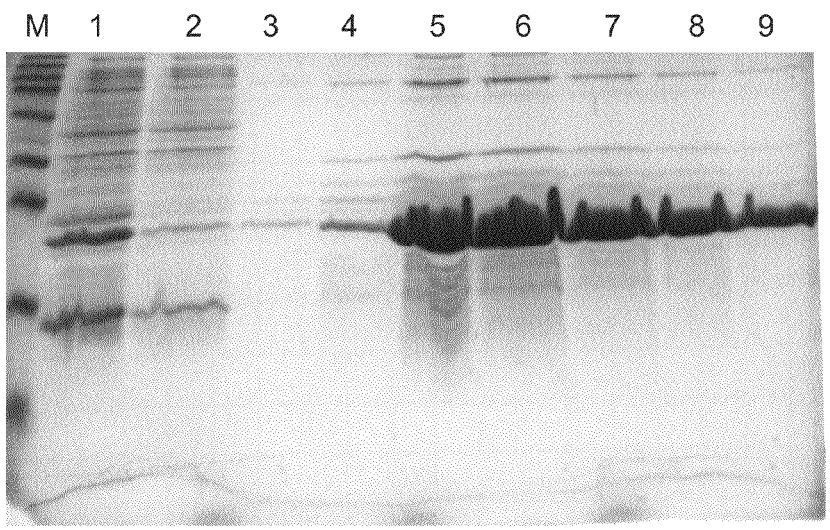

FIGS. 3A, 3B, 3C, and 3D: Expression and Sub-Cellular Localization of TAT-MTSlad-FRA and TAT-MTScs-FRA Fusion Proteins FIG. 3 presents an image of SDS-PAGE analysis of bacterial sub-fractions expressing the TAT-MTSlad-FRA fusion protein (FIG. 3A) and an immunoblot of Western blot analysis thereof (FIG. 3B) using anti-His antibody; FIG. 3C presents an image of SDS-PAGE analysis of bacterial sub-fractions expressing TAT-MTScs-FRA fusion protein and an immunoblot of Western blot analysis thereof using anti-His antibody is presented in FIG. 3D.

Abbreviations (for FIG. 3A-3D): 1, whole cell extract; 2, soluble fraction; 3, insoluble fraction; KDa, kilo Dalton; and M=marker. Arrow heads indicate the fusion proteins.

FIGS. 4A, 4B, 4C, and 4D: Purification of TAT-MTSfra-FRA and of TAT-MTSorf-FRA Fusion Proteins FIG. 4 presents an image of an affinity chromatography purification profile of the fusion protein TAT-MTSfra-FRA (FIG. 4A) and an image of SDS-PAGE analysis of the purification steps obtained for TAT-MTSfra-FRA is presented in FIG. 4B. An image of an affinity chromatography purification profile of the fusion protein TAT-MTSorf-FRA is presented in FIG. 4C and an image of SDS-PAGE analysis of the purification steps obtained for TAT-MTSorf-FRA is presented in FIG. 4D.

Abbreviations: M, marker; 1, whole cell extract; 2, pre-run fraction (the soluble sub-fraction of bacterial cells expressing the fusion protein); 3, flow through; 4, elution with 100 mM imidazole; and 5-9, elution with 250 mM imidazole.

FIGS. 5A, 5B, 5C, and 5D: Purification of TAT-MTSlad-FRA and of TAT-MTScs-FRA Fusion Proteins FIG. 5 presents an image of an affinity chromatography purification profile of the fusion protein TAT-MTSlad-FRA (FIG. 5A) and an image of SDS-PAGE analysis of the purification steps obtained for TAT-MTSlad-FRA is presented in FIG. 5B. An image of an affinity chromatography purification profile of the fusion protein TAT-MTScs-FRA is presented in FIG. 5C and an image of SDS-PAGE analysis of the purification steps obtained for TAT-MTScs-FRA is presented in FIG. 5D.

Abbreviations: M, marker; 1, whole cell extract; 2, pre-run fraction (the soluble sub-fraction of bacterial cells expressing the fusion protein); 3, flow through; 4, elution with 100 mM imidazole; and 5-9, elution with 250 mM imidazole.

Figure 6A:
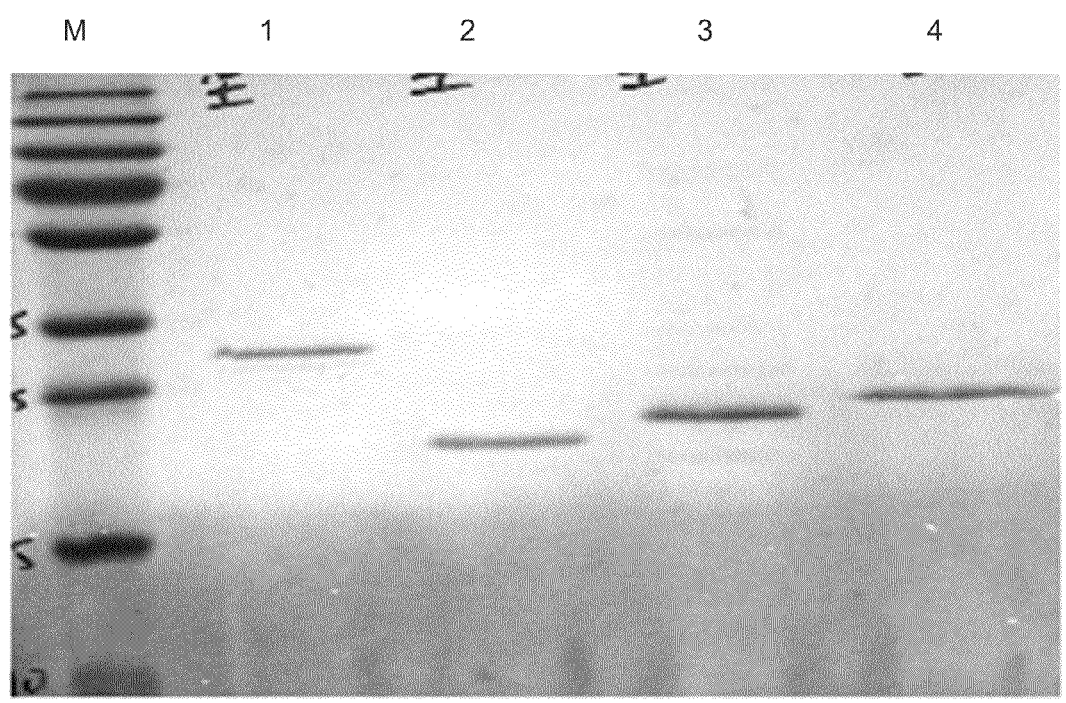
Figure 6C:
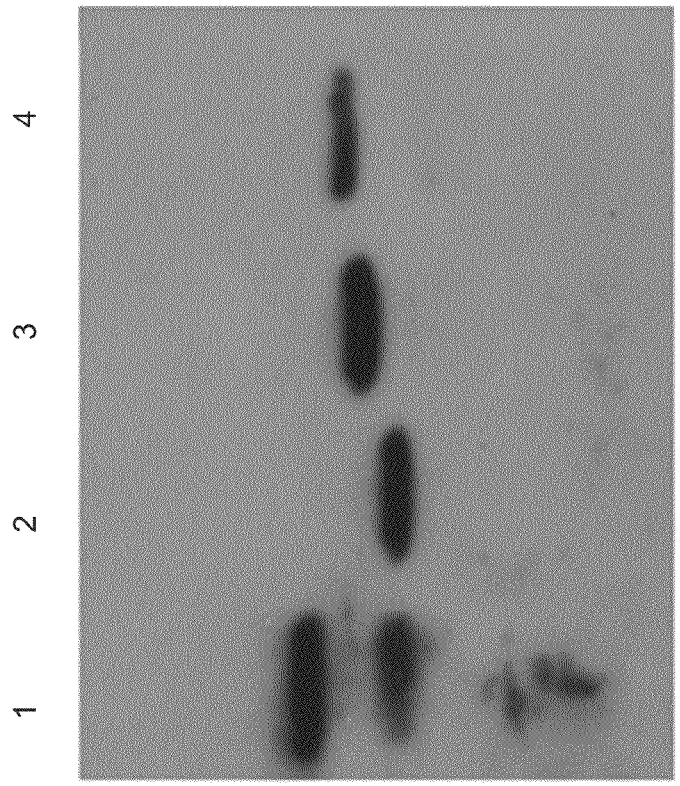
Figure 6B:
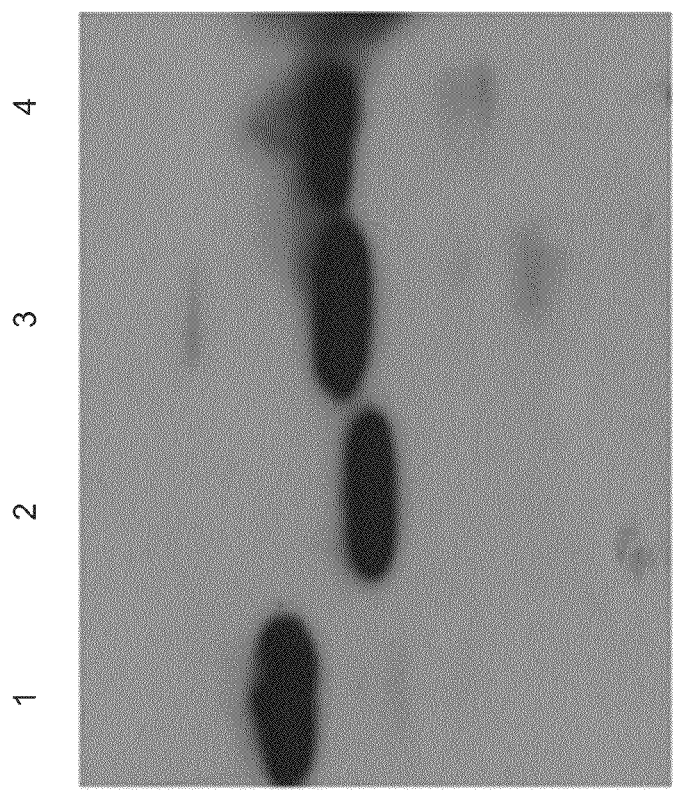

FIGS. 6A, 6B, and 6C: Characterization of TAT-MTS-FRA Highly Purified Fusion Proteins The four highly purified TAT-MTS-FRA fusion proteins were characterized by a SDS-PAGE gel (FIG. 6A) and by Western blot analyses using anti-His (FIG. 6B) or anti-frataxin (FIG. 6C) antibodies.

Abbreviations: 1, TAT-MTSfra-FRA; 2, TAT-MTScs-FRA; 3, TAT-TSlad-FRA; 4, TAT-MTSorf-FRA; and M, Marker.

Figure 7A:
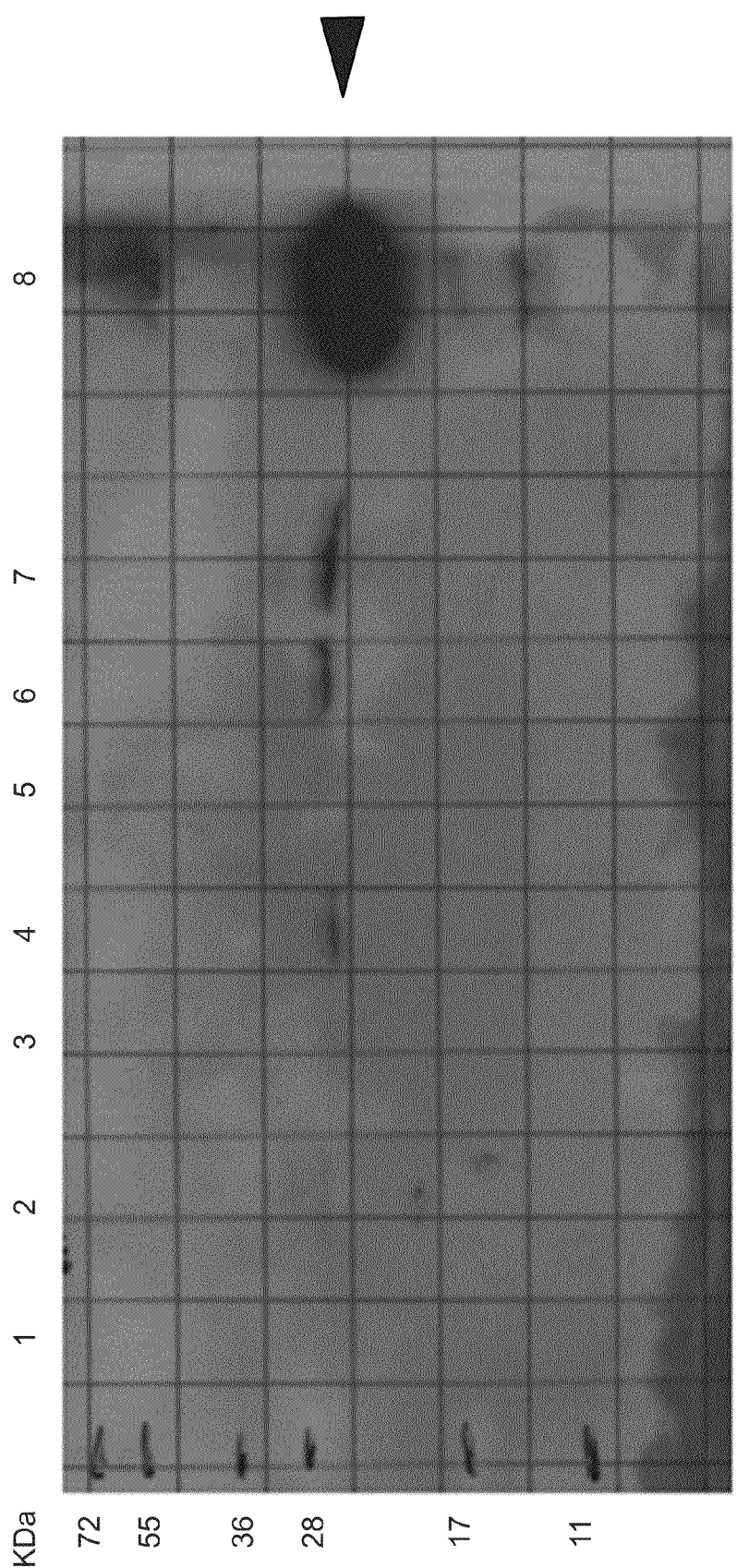
Figure 7B:
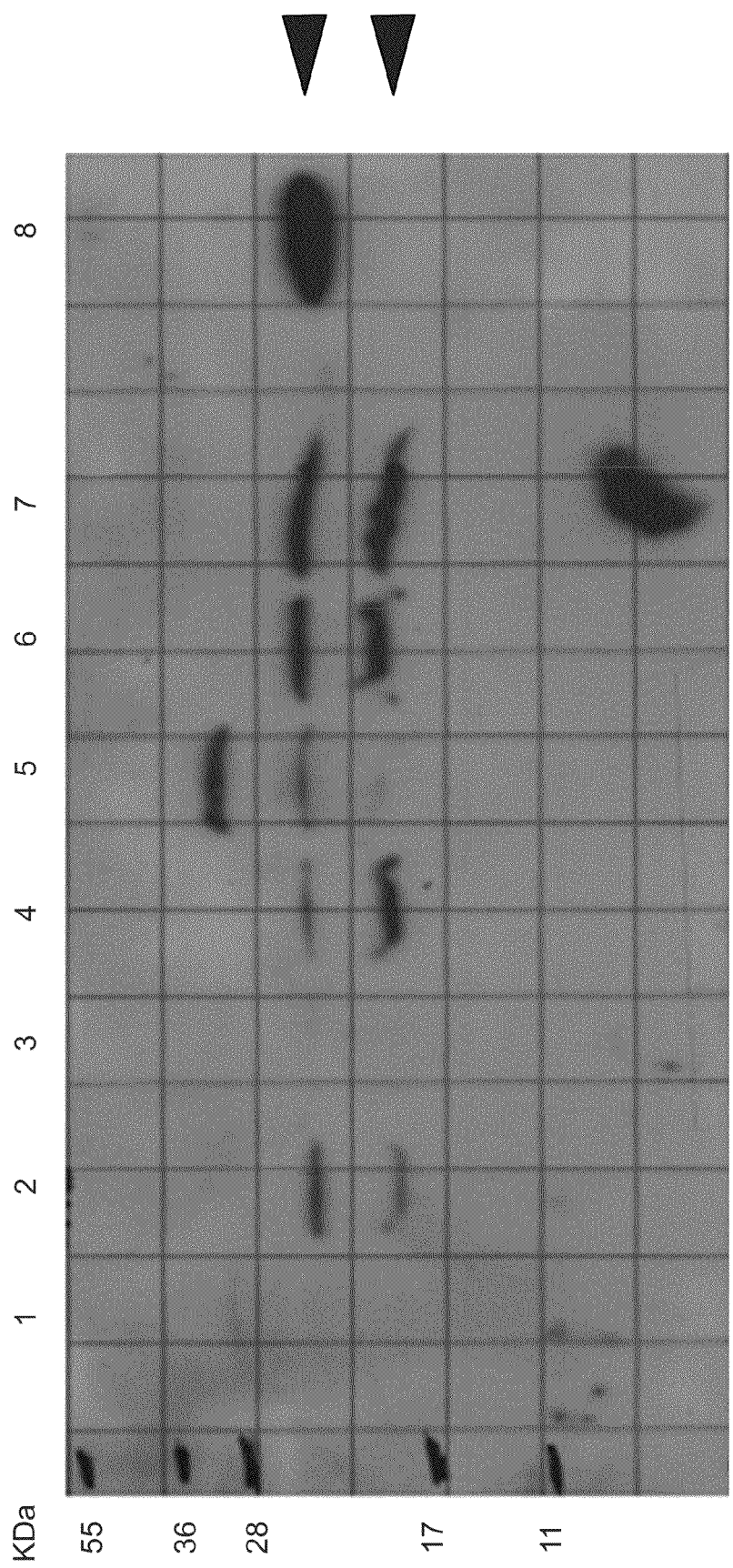

FIG. 7A-7B: Internalization of TAT-MTSlad-FRA into Cells and their Mitochondria

FIG. 7A presents an immunoblot of a Western blot analysis using anti-His antibodies and FIG. 7B presents an immunoblot of a Western blot analysis using anti frataxin antibodies performed with BJAB cells incubated in the absence (lanes 1 & 2) or in the presence of TAT-MTSlad-FRA (lanes 3-7). At the end of the incubation period, sub-fractionation was performed, obtaining the cytoplasmic and mitochondrial fractions. Fractions were separated by SDS-PAGE and subjected to Western blot analysis.

Abbreviations: control, untreated cells: cytoplasm (1), mitochondria (2); cells treated for 1 hr with the fusion protein: cytoplasm (3), mitochondria (4); cells treated for 5 hr: cytoplasm (5), mitochondria (6, 7; from two separate experiments); highly purified TAT-MTSlad-FRA fusion protein as a positive control is shown in (8). Arrow-heads indicate the fusion protein (or its processing products, indicated by the lower arrow-head in FIG. 7B).

Figure 8A:
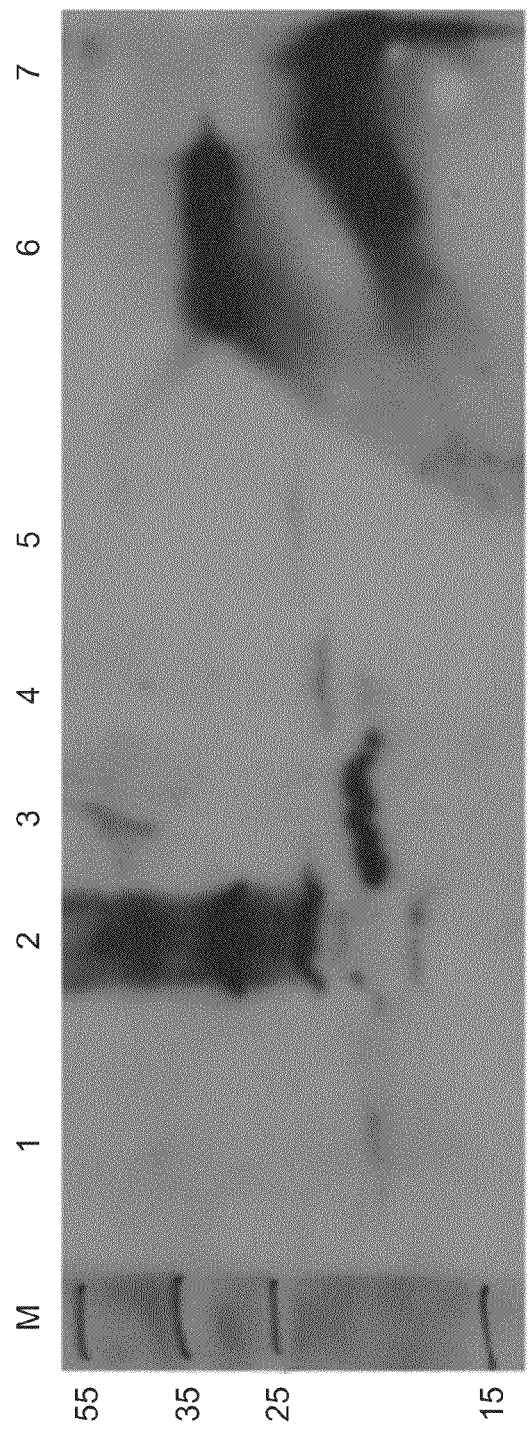
Figure 8B:
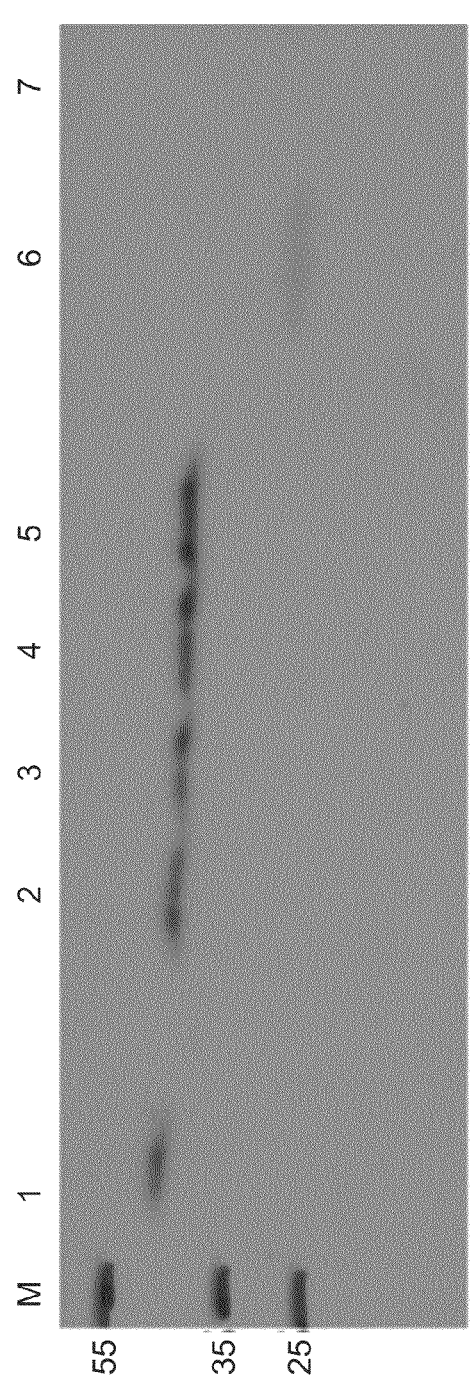

FIG. 8A-8B: Internalization of TAT-MTS-FRA Fusion Proteins into Mitochondria of Cells FIG. 8A presents a Western blot analysis using anti-FRA antibodies of cells incubated for 3 hours with TAT-MTS-FRA fusion proteins, each fusion protein at a final concentration of 0.02 μg/μl. The cells were washed and their mitochondria were isolated.

FIG. 8B presents a Western blot analysis using anti-E1α antibodies of cells as detailed above.

Abbreviations: M, marker; mitochondria isolated from control cells without any treatment (1), cells incubated with TAT-MTSfra-FRA (2), cells incubated with TAT-MTScs-FRA (3), cells incubated with TAT-MTSlad-FRA (4), cells incubated with TAT-MTSorf-FRA (5), purified TAT-MTSfra-FRA fusion protein (6), and purified TAT-MTScs-FRA fusion protein (7).

Figure 9A:
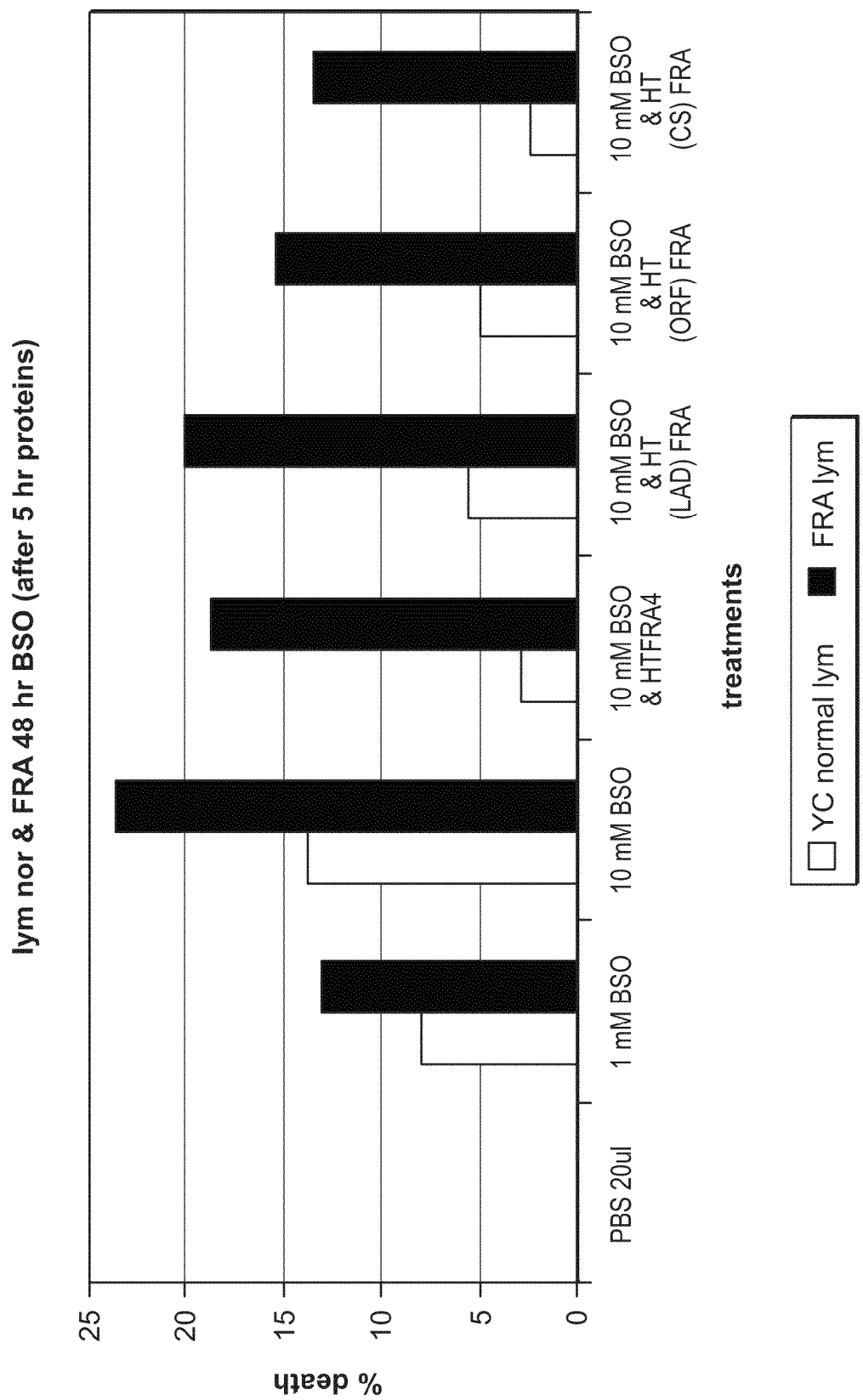
Figure 9B:
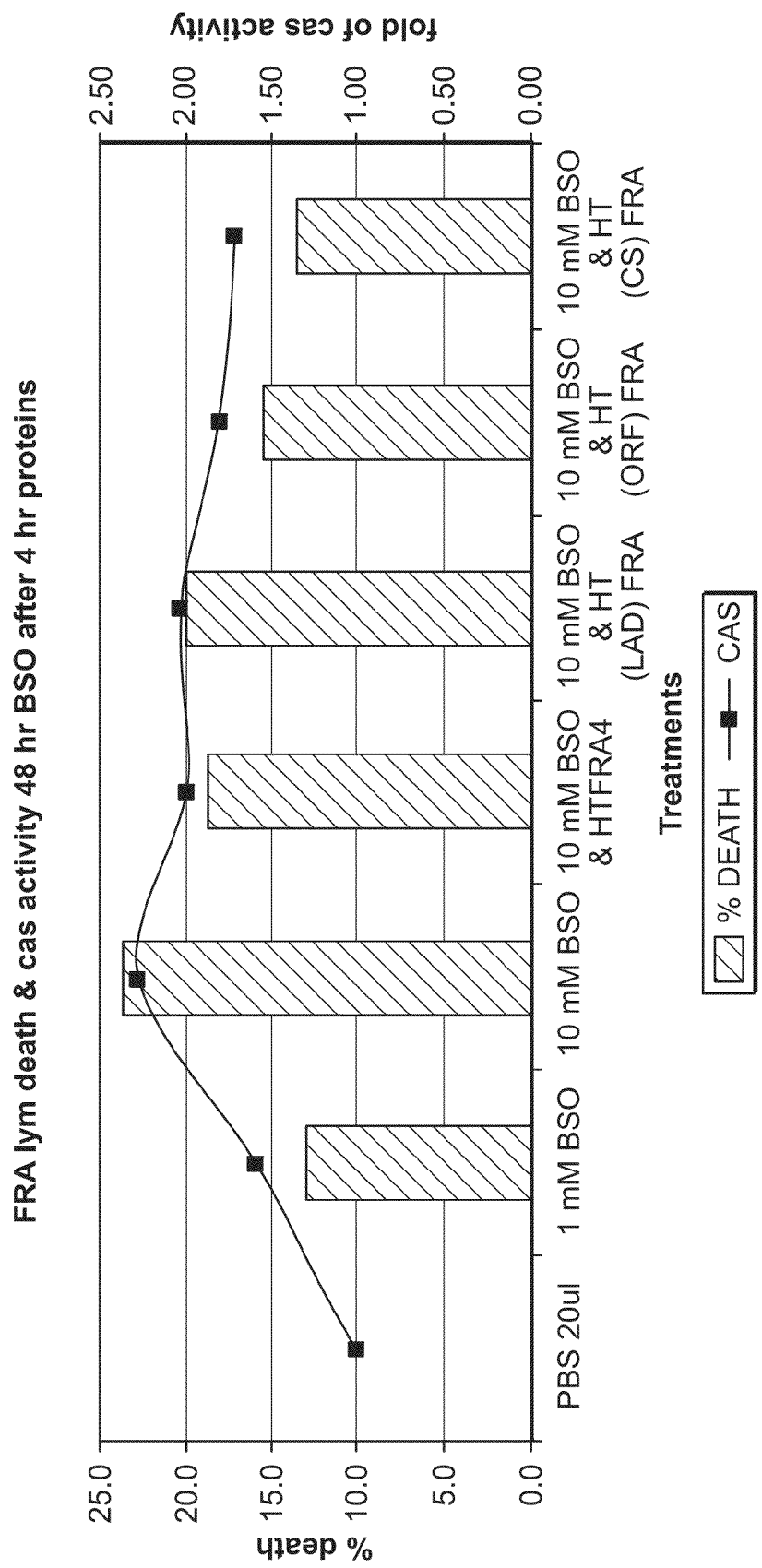

FIG. 9A-9B: TAT-MTS-FRA Fusion Proteins Partially Rescue Cells from BSO-Induced Oxidative Stress FIG. 9A presents a bar diagram showing percentage of cell death induced by L-Buthionine-sulfoximine (BSO). Normal lymphocytes or cells obtained from Friedreich's ataxia (FRDA) patients (FRA 48) were seeded, incubated for 5 hr with the various TAT-MTS-FRA fusion proteins, after which BSO at different concentrations was added for additional 48 hr. At the end of the incubation time, cell cultures were subjected to cell proliferation assays.

FIG. 9B presents a bar diagram showing percentage of cell death induced by L-Buthionine-sulfoximine (BSO) correlated with caspase 3 activity within the cells, assessed by using the Apo-ONE Homogeneous Caspase 3/7 Assay Kit (Promega). Experiments were carried in parallel with cell viability assays.

Abbreviations: YC, normal lymphocytes; HTFRA=TAT-MTSfra-FRA, HT(LAD)FRA=TAT-MTSlad-FRA, HT(ORF)FRA=TAT-MTSorf-FRA, and HT(CS)FRA=TAT-MTScs-FRA.

Figure 10A:
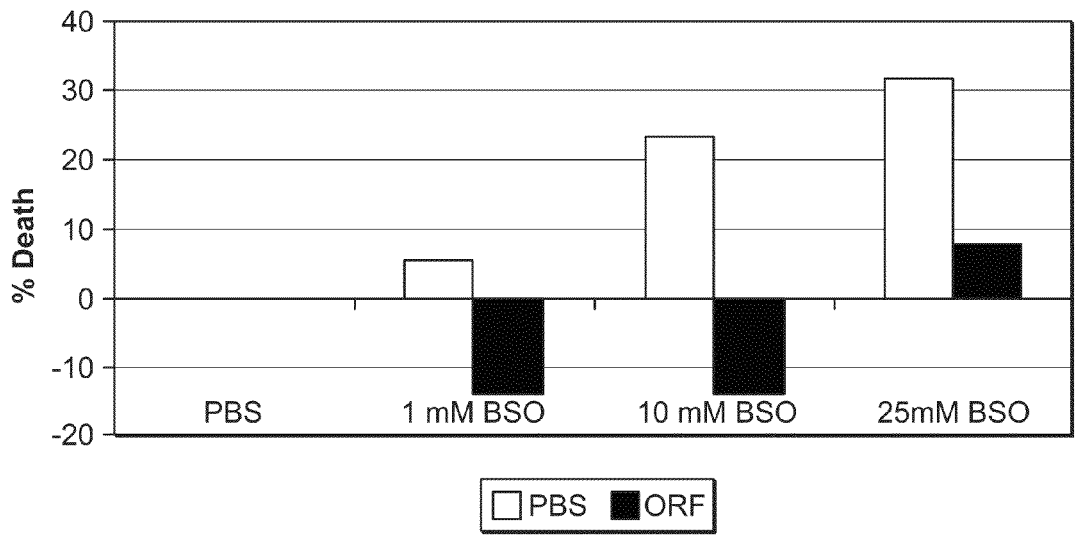
Figure 10B:
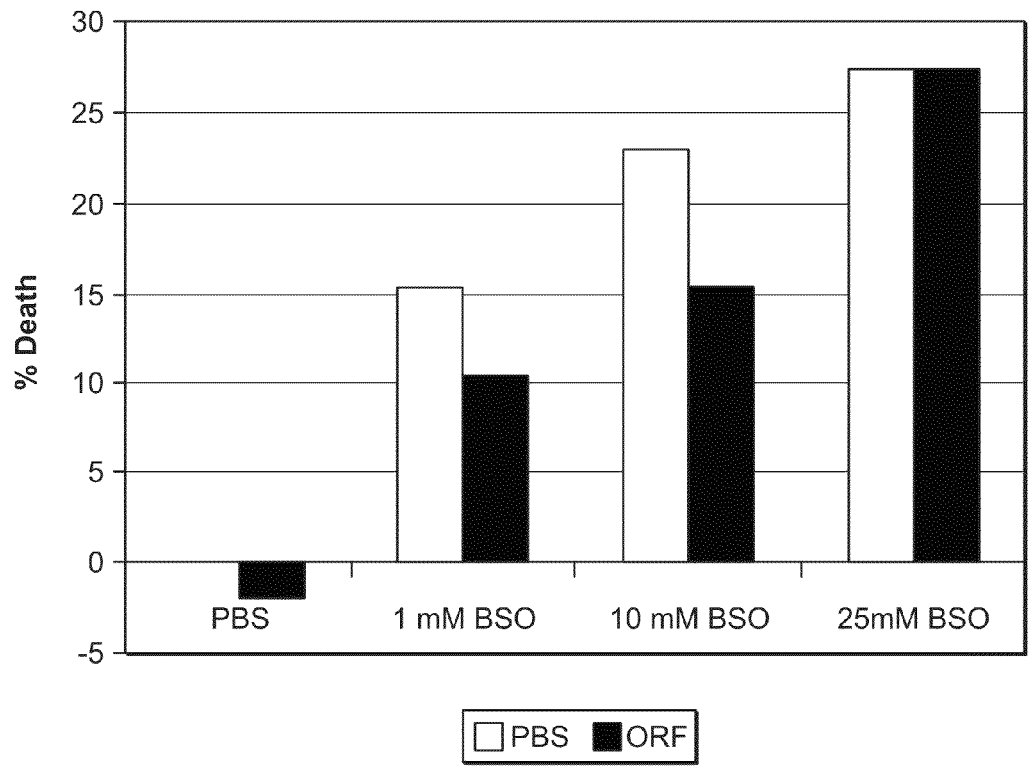

FIG. 10A-10B: TAT-MTSorf-FRA Rescues Lymphocytes and Fibroblasts Obtained from FRDA Patients from BSO-Induced Oxidative Stress FIG. 10A presents a bar diagram of percentage of cell death induced by BSO in fibroblasts obtained from FRDA patients (FRA 48) and FIG. 10B presents a bar diagram of percentage of cell death induced by BSO in lymphocytes obtained from patients (FRA 43). Cells were seeded, incubated for 24 hr with the TAT-MTSorf-FRA fusion protein, after which BSO at different concentrations was added for additional 48 hr. At the of the incubation time, cell cultures were subjected to cell proliferation assays.

Figure 11A:
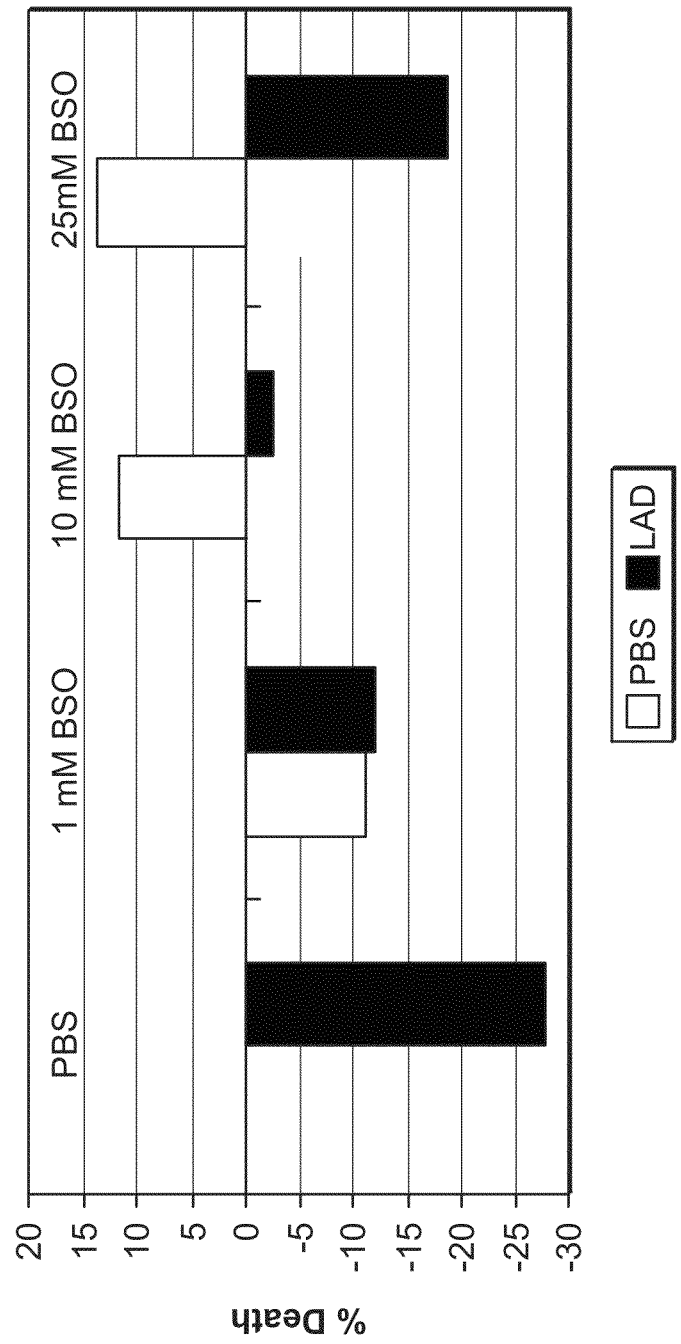

FIG. 11A-11B: TAT-MTSlad-FRA Rescues Fibroblasts Obtained from Patients from BSO-Induced Oxidative Stress FIG. 11A and FIG. 11B present bar diagrams of percentage of cell death induced by BSO in fibroblasts obtained from FRDA patients (FRA 48) of two representative experiments. Cells were seeded, incubated for 24 hr with the TAT-MTSlad-FRA fusion protein, after which BSO at different concentrations was added for additional 48 hr. At the of the incubation time, cell cultures were subjected to cell proliferation assays.

FIGS. 12A, 12B, 12C, and 12D: TAT-MTS-FRA Fusion Proteins Partially Rescue Fibroblasts Obtained from Patients from BSO-Induced Oxidative Stress, a Comparison FIG. 12A to FIG. 12D present bar diagrams of percentage of cell death induced by BSO in fibroblasts obtained from FRDA patients (FRA 48). Cells were seeded, incubated for 24 hr with the TAT-MTSfra-FRA (FIG. 12A), TAT-MTScs-FRA (FIG. 12B), TAT-MTSlad-FRA (FIG. 12C) and with the TAT-MTSorf-FRA (FIG. 12D) fusion protein, after which BSO at different concentrations was added for additional 48 hr. At the end of the incubation time, cell cultures were subjected to cell proliferation assays.

FIGS. 13A, 13B, 13C, and 13D: TAT-MTS-FRA Fusion Proteins Constructs FIG. 13A to FIG. 13D are schematic presentations of TAT-MTS-FRA fusion protein constructs comprising a HIV-1 transactivator of transcription (TAT) domain (boxed) fused to a GSDP linker (colored in grey) fused to a human mitochondria targeting sequence (MTS) of a human mitochondrial protein (double-underlined) selected from frataxin (MTSfra, FIG. 13A), citrate synthase (MTScs, FIG. 13B), lipoamide dehydrogenase (MTSlad, FIG. 13C) and C6ORF66 (MTSorf, FIG. 13D) fused to human frataxin (underlined).

DETAILED DESCRIPTION OF EMBODIMENTS

The presently disclosed subject matter relates to the preparation of various plasmid constructs encoding TAT-MTS-Frataxin fusion proteins, providing a basis of a wide-range therapeutic tool for delivering mitochondrial proteins into mitochondria.

The protein constructs described herein, comprising a mitochondrial protein as well as TAT and a specific mitochondrial targeting sequence (MTS), enabling the mitochondrial protein to cross both cellular and mitochondrial membranes, were expressed and purified and their biological activity was verified. Remarkably, the protein yield obtained for fusion protein constructs comprising an MTS which was other than the native MTS of the mitochondrial protein present in the fusion construct (e.g. MTS heterologous to frataxin), was superior to the yield obtained for a frataxin fusion protein construct comprising the native MTS of frataxin.

As demonstrated below, the inventors show that various fusion proteins are able to enter the mitochondria within intact cells. In addition, the inventors show that the fusion proteins exhibit biological activity. For example, the various TAT-MTS-FRA fusion proteins were shown to rescue cells obtained from Friedreich ataxia patients as well as normal cells from oxidative stress, as demonstrated in the Examples below. Surprisingly, a superior protective effect was observed for fusion proteins carrying an MTS, which was other than the native MTS of the mitochondrial protein present in the fusion construct (a heterologous MTS) as compared to the effect demonstrated by the fusion protein carrying the native MTS.

The presently disclosed subject matter provides fusion protein constructs comprising heterologous MTSs of human nuclear-encoded mitochondrial proteins that are classical MTS sequences, which are known to be removed upon entry to the mitochondria. By a non-limiting example, a delivery system as herein described comprising frataxin may be used for the treatment or alleviation of Friedreich's ataxia or any other disorder associated with a deficiency of frataxin or defective frataxin.

Thus, the presently disclosed subject matter provides a fusion protein comprising a HIV-1 transactivator of transcription (TAT) domain, a functional human mitochondrial protein and a human mitochondria targeting sequence (MTS) situated between said TAT domain and said functional mitochondrial protein and wherein said human MTS is heterologous to said functional protein.

The term "functional human mitochondrial protein" as used herein refers to any protein which is essential for a biological activity of mitochondria. A functional human mitochondrial protein may be a protein, which is active when present in the mitochondria by itself (per se) or a protein that when present in the mitochondria functions as a component of a mitochondrial multi-component complex (i.e. with other enzymes, co-factors, or proteins). Typically, a functional human mitochondrial protein is a protein, which, when absent, deficient or mutated, causes a mitochondrial disorder or is associated with a mitochondrial disorder.

In some specific embodiments, the functional mitochondrial protein refers to the full-length amino acid sequence of the protein. In other embodiments, the functional mitochondrial protein is a fragment of the full-length amino acid sequence, sufficient to carry out the mitochondrial protein activity, either alone or as part of a multi-component complex, as appropriate.

In further embodiments, the functional human mitochondrial protein is a mutated derivative of said protein, wherein one or more of the native amino acid residues has been deleted, replaced or modified while still maintaining the mitochondrial functionally of the protein (alone or as part of a multi-component complex).

In the above and other embodiments, the functional human mitochondrial protein (also denoted "mature" protein) refers to a protein devoid of its mitochondrial targeting sequence (MTS). In other words, the fusion protein construct herein provided comprises a functional mitochondrial protein, which, upon entry to the mitochondria is cleaved off from the fusion protein construct in its mature, active (functional) state.

By way of non-limiting example, in the above and other embodiments of the disclosed subject matter, the functional human mitochondrial protein whose activity is supplied by a fusion protein of the present invention may be any one of human frataxin (the mature protein having the amino acid sequence denoted by SEQ ID NO: 26 and encoded by the nucleic acid sequence denoted by SEQ ID NO: 6), ornithine transcarbamoylase (OTC, encoded by the nucleic acid sequence denoted by SEQ ID NO: 15), human Lipoamide Dehydrogenase (LAD), 2-oxoisovalerate dehydrogenase alpha subunit (Branched-Chain Keto Acid Dehydrogenase E1α) (NCBI Protein Database Accession No. P12694; OMIM:248600), 2-oxoisovalerate dehydrogenase beta subunit (Branched-Chain Keto Acid Dehydrogenase E1β; P21953), Acyl-CoA dehydrogenase, medium-chain specific (P1 1310; OMIM:201450), Acyl-CoA dehydrogenase, very-long-chain specific (P49748; OMIM:201475), Trifunctional enzyme alpha subunit (Long-chain 3 hydroxyacyl CoA Dehydrogenase or LCHAD) (P40939; OMIM:609015) (HADHA), Trifunctional enzyme beta subunit (Hydroxyacyl-CoA Dehydrogenase/3-Ketoacyl-CoA Thiolase/Enoyl-CoA Hydratase (P55084) (HADHB)), Pyruvate dehydrogenase E1 component beta subunit (P1 1177; OMIM:208800), and Pyruvate dehydrogenase E1 component alpha subunit (P08559; 0MIM:312170).

In some embodiments, the human mitochondrial protein is a functional mitochondrial protein per se and/or as a component of a mitochondrial multi-component complex.

As indicated above, the functional human mitochondrial protein of the disclosed subject matter may be a protein which is active when present in the mitochondria by itself (i.e. the protein per se is active) or a protein that when present in the mitochondria functions as a component of a mitochondrial multi-component complex (i.e. with other enzymes, co-factors, or proteins). The term "mitochondrial multi-component complex" as used herein refers to an enzyme that forms a complex with other enzymes or proteins that is essential for a biological activity of mitochondria.

As shown by the inventors in the Examples below (FIG. 7), the fusion protein comprising a TAT and MTS sequences is cleaved upon entry to the mitochondria, and a mature active protein is obtained. The protein construct provided by the presently disclosed subject matter thus allows a human mitochondrial protein, which is first covalently attached to TAT and MTS domains, to cross both cellular and mitochondrial membranes, and once inside the mitochondria, be processed by mitochondrial peptidases while retaining its biological activity and proper conformation. The delivery system described herein thus enables a human mitochondrial protein to retain its mitochondrial function per se or the integration thereof in a mitochondrial multi-component complex.

The mitochondrial multi-component complex encompassed by the present disclosure refers to a group of at least two different proteins assembled together in a specific ratio that functions in a coordinated fashion to catalyze a series of reactions. The function of a mitochondrial multi-component complex is dependent on its structure; thus, the proteins that compose the complex must properly fold and physically fit together in the proper configuration in order to efficiently catalyze the series of reactions.

In all embodiments, the functional human mitochondrial protein according to presently disclosed subject matter is cleaved off from the fusion protein construct upon entry to the mitochondria and resides therein at its mature, properly-folded active state. In some embodiments, the functional human mitochondrial protein may readily then integrate into a conformationally-sensitive mitochondrial multi-component complex.

By way of non-limiting example, the presently disclosed subject matter encompasses a mitochondrial multi-component complex which is any one of pyruvate dehydrogenase complex (PDHC), α-ketoglutarate dehydrogenase complex (KGDHC), and branched-chain keto-acid dehydrogenase complex (BCKDHC), the complexes of the respiratory chain, and those involved in fatty acid β-oxidation and the urea cycle. The complexes of the respiratory chain are complex I (NADH-ubiquinone oxidoreductase), complex II (succinate-ubiquinone oxidoreductase), complex III (ubiquinol-ferricytochrome c oxidoreductase), complex IV (cytochrome c oxidoreductase), and complex V (FIFO ATPase) where each mitochondrial multicomponent complex represents a separate embodiment of the present invention.

As shown in Examples 1-3 below, the inventors have clones, expressed and purified fusion protein constructs comprising the protein frataxin.

The mitochondrial protein human frataxin (FXN) is an essential and highly conserved protein expressed in most eukaryotic organisms that appears to function in mitochondrial iron homeostasis, notably the de novo biosynthesis of iron-sulfur (Fe—S) cluster proteins and heme biosynthesis. The exact function of FXN has not been defined but recent studies suggest that FXN functions as an allosteric activator with $Fe^{2+}$ for Fe—S cluster biosynthesis. The absence of FXN is associated with a loss of activity in Fe—S-containing proteins, such as aconitase as well as with the disease Friedreich ataxia.

Precursor FXN protein (23.1 kDa, 210 amino acids) comprises an 80 amino acid mitochondrial targeting sequence (MTS) at its amino (N) terminus. Within mitochondria, the precursor FXN protein is processed in two steps by the mitochondrial matrix processing peptidase (MPP). It has been shown that the intermediate form of FXN is formed by cleavage at residue 42 by the MPP, and the resulting form of FXN (FXN42-210) has been shown to be cleaved at amino acid 81, yielding a mature, 130 amino acid protein, with a predicted molecular weight of 14.2 kDa.

As indicated above, Friedreich ataxia is an autosomal recessive degenerative disorder characterized by ataxia, areflexia, sensory loss, weakness, scoliosis, and cardiomyopathy. A deficiency of frataxin in cells leads to decreased activities of mitochondrial iron-sulfur cluster-containing enzymes, to an accumulation of iron in the mitochondrial matrix, increased sensitivity to oxidative stress, as well as to impaired adenosine triphosphate (ATP) production.

In the above and other embodiments of the presently disclosed subject matter, frataxin refers to human frataxin and any biologically active fragments and derivatives thereof, which is devoid of its natural (native) MTS sequence. Non limiting examples for mature human frataxin are given by the accession number Q16595[81-210] and as indicated in Table 1 below, where the amino acid sequence of mature human frataxin is as set forth in SEQ ID NO: 26 and the nucleic acid sequence encoding therefor is as set forth in SEQ ID NO: 6.

Notably, as shown in Example 4 below, a TAT-MTS-frataxin fusion protein was demonstrated by the inventors to enter mitochondria of human intact BJAB cells. Analysis of sub-cellular fractions of these cells, in order to separate the mitochondria from the cytosol, verified that the various frataxin fusion protein constructs (i.e. TAT-MTSlad-FRA, TAT-MTSfra-FRA, TAT-MTScs-FRA, and TAT-MTSorf-FRA) were indeed successfully delivered into the mitochondria. Surprisingly, among the fusion proteins carrying a heterologous MTS, the MTS of Citrate synthase was shown by the inventors to be delivered into the mitochondria in the most efficient manner.

Delivery of fusion proteins comprising a mitochondrial protein into the mitochondria has far-reaching therapeutic beneficial implications for treatment of mitochondrial disorders in general, and delivery of frataxin into mitochondria has specific therapeutic benefit for treatment of Friedreich's ataxia in particular.

As noted above, ornithine transcarbamoylase (OTC) (also called ornithine carbamoyltransferase) is also encompassed by the presently disclosed subject matter.

OTC is a protein having enzymatic activity that catalyzes the reaction between carbamoyl phosphate (CP) and ornithine (Orn) to form citrulline (Cit) and phosphate ($P_i$). In mammals OTC is located in the mitochondria and is part of the urea cycle. OTC is a trimer, and the active sites thereof are located at the interface between the protein monomers, emphasizing the importance of proper folding to the mitochondrial activity of the protein. Deficiency in OTC results in an increase in ammonia level, leading to neurological problems.

Thus, in the above and other embodiments of the disclosed subject matter, the functional human mitochondrial protein is specifically any one of frataxin and ornithine transcarbamoylase (OTC). In some embodiments, the nucleic acid encoding the mature OTC protein is denoted by SEQ ID NO: 15.

As indicated above, the presently disclosed subject matter provides a fusion protein comprising a HIV-1 transactivator of transcription (TAT) domain, a functional human mitochondrial protein and a human mitochondria targeting sequence (MTS) situated between said TAT domain and said functional mitochondrial protein and wherein said human MTS is heterologous to said functional protein.

Most of the proteins directed to the mitochondria are synthesized with a mitochondrial targeting (or translocation) sequence (MTS), which allows their import from the cytoplasm into mitochondria through the translocation machinery. Once entering the mitochondria, the MTS is recognized and cleaved off, allowing for proper processing and, if necessary, assembly into mitochondrial enzymatic complexes.

Thus, as used herein, the term "mitochondria targeting sequence", MTS or "mitochondria translocation sequence" refers to an amino acid sequence capable of causing the transport into the mitochondria of a protein, peptide, amino acid sequence, or compound attached thereto, and any biologically active fragments thereof. MTSs used in the fusion protein constructs in accordance with the presently disclosed subject matter, which are situated N-terminal to the functional mitochondrial protein, are typically from about 15 to about 40 amino acids in length, including about 3 to about 5 nonconsecutive basic amino acid (arginine/lysine) residues, often with several serine/threonine residues but without acidic amino acid (asparate/glutamate) residues. In their molecular structure, these MTSs are able to form strong basic amphipathic α-helices that are essential for efficient mitochondrial transportation.

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range. In the above and other embodiments, the MTS is human MTS, namely MTS of a human mitochondrial protein.

In the above and other embodiments of the presently disclosed subject matter the MTS comprises from about 15 to about 40 amino acid residues, including from about 3 to about 5 nonconsecutive (i.e. which are not covalently linked one to the other in a sequential manner) basic amino acid residues, and optionally from about 1 to about 3 or 4 or 5 serine/threonine residues.

The term "amino acid residues" as used herein refers to naturally occurring and synthetic amino acids, as well as amino acid analogs and amino acid mimetics that can function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. "Amino acid analogs and amino acid mimetics" refers to compounds that have the same fundamental chemical structure as a naturally occurring amino acid. Such analogs have modified R groups or modified peptide backbones, but retain the same basic chemical structure as a naturally occurring amino acid. Amino acids may be referred to herein by either their commonly known three letter symbols or by the one-letter symbols recommended by the IUPAC-IUB Biochemical Nomenclature Commission.

It is well known in the art that amino acid residues may be divided according to their chemical properties to various groups, inter alia, on the basis of similarity in polarity, charge, solubility, hydrophobicity, hydrophilicity, and/or the amphipathic nature of the residues involved.

For example, nonpolar "hydrophobic" amino acids are selected from the group consisting of Valine (V), Isoleucine (I), Leucine (L), Methionine (M), Phenylalanine (F), Tryptophan (W), Cysteine (C), Alanine (A), Tyrosine (Y), Histidine (H), Threonine (T), Serine (S), Proline (P), Glycine (G), Arginine (R) and Lysine (K); "polar" amino acids are selected from the group consisting of Arginine (R), Lysine (K), Aspartic acid (D), Glutamic acid (E), Asparagine (N), Glutamine (Q); "positively charged" amino acids are selected form the group consisting of Arginine (R), Lysine (K) and Histidine (H) and wherein "acidic" amino acids are selected from the group consisting of Aspartic acid (D), Asparagine (N), Glutamic acid (E) and Glutamine (Q). "Basic" amino acids are selected from the group consisting of Histidine (H), lysine (K) and Arginine (R), which are polar and positively charged at pH values below their pKa's, and are very hydrophilic.

As indicated above, the presently disclosed subject matter encompasses human mature frataxin and any biologically active fragments and derivatives thereof, which is devoid of its natural (native) MTS sequence. By the term "biologically active fragments and derivatives" it is meant any variations, including deletion, substitution and/or insertion of one or more amino acid residues in the amino acid sequences of mature frataxin (or in the nucleic acid encoding therefor), for example 1, 2, 3, 4, 5 or more amino acid residues, in accordance with the presently disclosed subject matter which would not alter the biological activity of frataxin.

The invention further relates to DNA constructs comprising the nucleic acid sequence of the presently disclosed subject matter or biologically functional fragments and derivatives thereof. The constructs of the presently disclosed subject matter may further comprise additional elements such as promoters, regulatory and control elements, translation, expression and other signals, operably linked to the nucleic acid sequence of the invention.

It is known that each mitochondrial enzyme produced in the cytoplasm and transported into the mitochondria is produced as a precursor protein, carrying its natural MTS. Thus, the precursor mitochondrial protein already has its native MTS. However, this naturally occurring sequence in the precursor protein may be exchanged with any other known MTS.

As exemplified herein, the fusion protein constructs comprising frataxin prepared by the inventors further comprised MTSs of lipoamide dehydrogenase (MTSlad, of the amino acid sequence denoted by SEQ ID NO: 24 and encoded by the nucleic acid sequence denoted by SEQ ID NO: 5), C6ORF66 (MTSorf, of the amino acid sequence denoted by SEQ ID NO: 25 and encoded by the nucleic acid sequence denoted by SEQ ID NO: 4), and of citrate synthase (MTScs, of the amino acid sequence denoted by SEQ ID NO: 23 and encoded by the nucleic acid sequence denoted by SEQ ID NO: 3), as well as the native MTS of frataxin (MTSfra, of the amino acid sequence denoted by SEQ ID NO: 22 and encoded by the nucleic acid sequence denoted by SEQ ID NO: 2). In addition, the inventors showed that fusion protein constructs comprising frataxin and a MTS sequence that is not the native MTS of frataxin (i.e. heterologous MTS) were superior to the frataxin fusion protein construct comprising the native MTS, based on the higher yield obtained for fusion protein constructs comprising heterologous MTS during the expression and purification stages.

Surprisingly, fusion protein constructs comprising frataxin and a heterologous MTS were also demonstrated by the inventors to have an enhanced biological activity as compared to the frataxin fusion protein construct comprising the native MTS (Example 5). In particular, a fusion protein construct comprising frataxin and citrate synthase MTS showed the highest effect in reducing toxicity of BSO (FIG. 9A and FIG. 9B). As shown in Example 4 below, the fusion protein construct comprising frataxin and citrate synthase MTS also showed the highest ability of being delivered into mitochondria among the exemplified constructs comprising heterologous MTS.

Figure 12A:
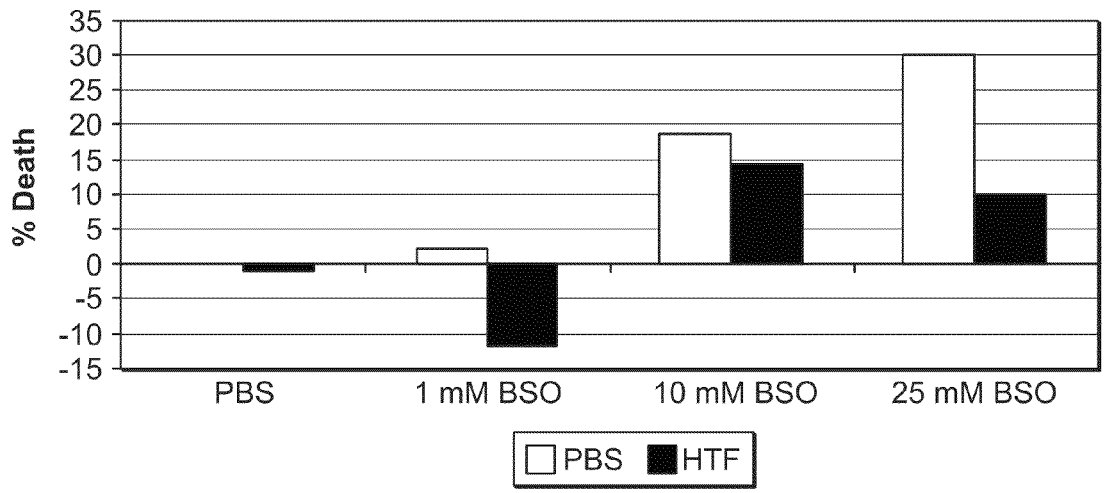
Figure 12B:
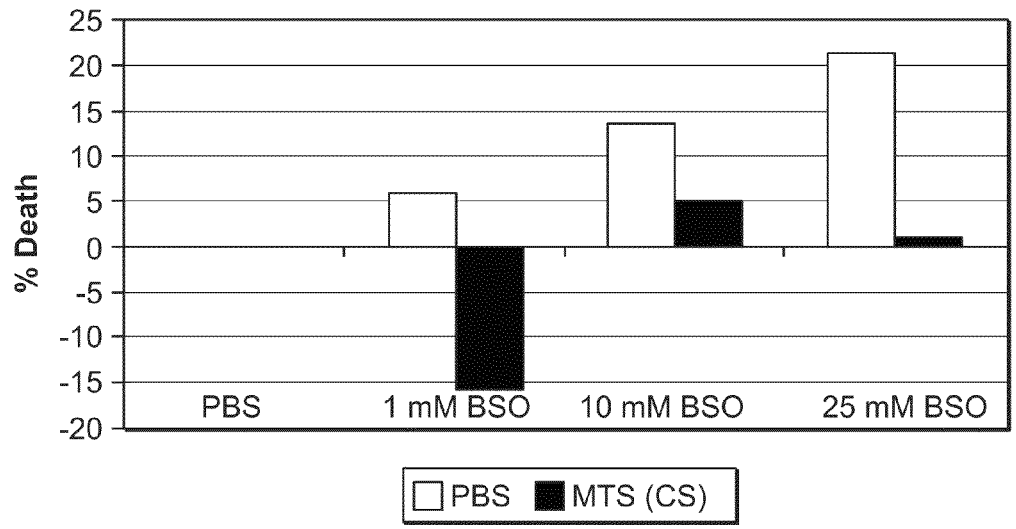
Figure 12C:
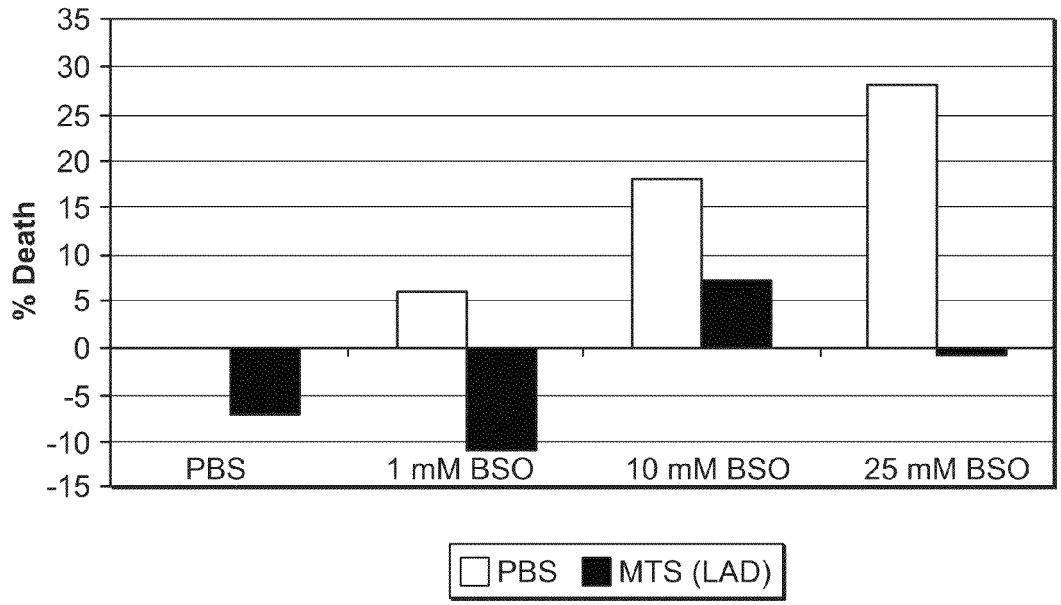
Figure 12D:
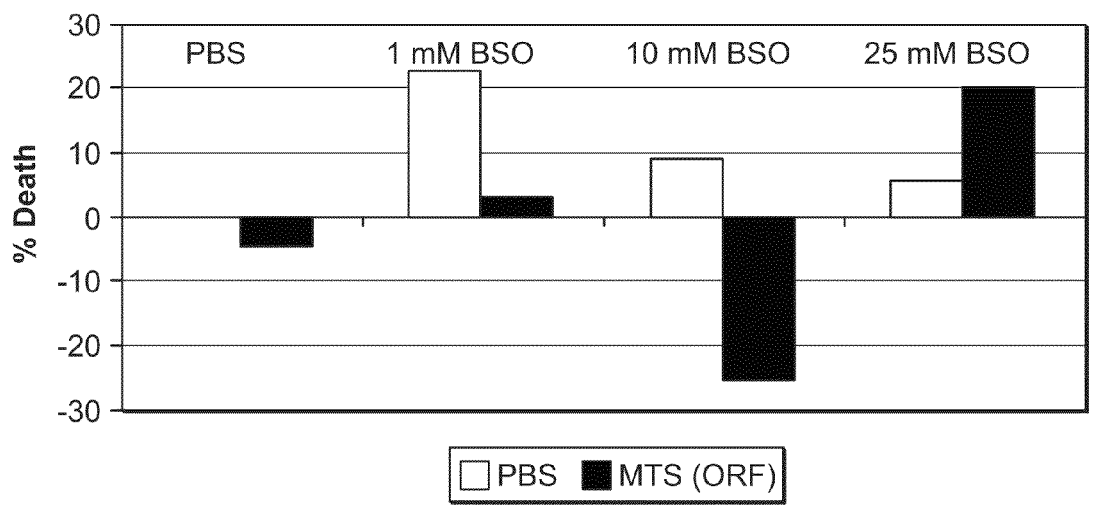

Consistent with the above results, a fusion protein construct comprising frataxin and another heterologous MTS, namely the MTS of lipoamide dehydrogenase (LAD), was also demonstrated by the inventors to have an enhanced biological activity as compared to the frataxin fusion protein construct comprising the frataxin native MTS, as demonstrated in FIG. 12C. As evident from FIG. 12, the biological activity of this fusion protein construct was comparable to the biological activity of the fusion protein construct comprising the citrate synthase MTS.

As detailed above, it is known that FXN mRNA is translated into a precursor polypeptide that is transported to the mitochondrial matrix and processed to at least two forms, namely FXN42-210 and FXN81-210, where FXN42-210 is the transient processing intermediate and FXN81-210 represents the mature protein. In other words, the transient frataxin polypeptide FXN42-210 includes a portion of the native frataxin MTS, whereas the FXN81-210 is the mature protein per se, devoid of its native MTS. Without wishing to be bound by theory, by using a heterologous MTS in fusion protein constructs comprising frataxin, mature frataxin is expected to be released from the fusion protein at a single step, thereby raising the biological availability of this protein in the mitochondria compared to fusion protein constructs comprising frataxin and its native MTS.

Thus, the MTS encompassed by the presently disclosed subject matter is any human MTS that is encoded by the nuclear DNA, translated (produced) in the cytoplasm and transported into the mitochondria and which is not the native N-terminal MTS sequence of the functional protein present in the fusion protein construct according to the invention. In other words, the MTS sequence is other than the native N-terminal MTS sequence of the functional protein, i.e. is heterologous thereto. The various MTS may be exchangeable for each mitochondrial enzyme among themselves. Each possibility represents a separate embodiment of the present invention.

As used herein, the term "heterologous" refers to MTS fused to the functional human mitochondrial protein according to the invention, which was obtained from another (distinct) mitochondrial protein.

By way of a non-binding example, the heterologous MTS according to the invention is a MTS being heterologous to the mitochondrial protein frataxin, as exemplified herein, which may be, but is not limited to, any one of the human mitochondrial proteins, e.g. lipoamide dehydrogenase (MTSlad, of the amino acid sequence denoted by SEQ ID NO: 24 and encoded by the nucleic acid sequence denoted by SEQ ID NO: 5), C6ORF66 (MTSorf, of the amino acid sequence denoted by SEQ ID NO: 25 and encoded by the nucleic acid sequence denoted by SEQ ID NO: 4), and of citrate synthase (MTScs, of the amino acid sequence denoted by SEQ ID NO: 23 and encoded by the nucleic acid sequence denoted by SEQ ID NO: 3).

Thus, in embodiments of the presently disclosed fusion protein constructs the MTS can be any one of human lipoamide dehydrogenase MTS (having the amino acid sequence denoted by SEQ ID NO: 24), the MTS of the human C6ORF66 gene product (having the amino acid sequence denoted by SEQ ID NO: 25), the human mitochondrial citrate synthase MTS (having the amino acid sequence denoted by SEQ ID NO: 23), and the MTS of human mitochondrial GLUD2 (encoded by the nucleic acid sequence denoted by SEQ ID NO: 16).

In some embodiments disclosed is a fusion protein comprising a HIV-1 transactivator of transcription (TAT) domain fused to human frataxin and a human mitochondria targeting sequence (MTS) of a human mitochondrial protein selected from lipoamide dehydrogenase (LAD) and citrate synthase (CS) situated between said TAT domain and said frataxin, wherein said frataxin is C-terminal to said MTS of human lipoamide dehydrogenase or human citrate synthase.

As indicated above, the fusion protein according to the presently disclosed subject matter comprises a HIV-1 transactivator of transcription (TAT) domain, located at the N-terminus of the fusion protein, N-terminal to the MTS as defined above, which is turn is situated N-terminal to the functional human mitochondrial protein (see FIG. 1 for a schematic presentation).

As used herein, the term HIV-1 transactivator of transcription (TAT) domain refers to a protein transduction domain which is an 11-amino-acid (residues 47-57) arginine- and lysine-rich portion of the HIV-I Tat protein having the amino acid sequence YGRKKRRQRRR as set forth in SEQ ID NO: 21. TAT-fusion protein constructs are known in the art to be introduced into cultured cells, intact tissue, and live tissues and cross the blood-brain barrier (BBB). TAT fusion proteins are also known to traverse mitochondrial membranes [13].

The presently disclosed subject matter also encompasses any fragments of the above defined TAT domain. For example, a TAT domain according to the presently disclosed subject matter may comprise from about 3 to about 11 (e.g. 4-11, 5-11, 6-11, 7-11, 8-11, 9, 10 or 11) sequential amino acid residues of the HIV-I Tat protein having the amino acid sequence YGRKKRRQRRR (SEQ ID NO: 21).

In some embodiments, the fragment of the above defined TAT domain comprise 9 sequential amino acid residues of the HIV-I Tat protein, having the amino acid sequence of RKKRRQRRR, as set forth in SEQ ID NO: 27 and encoded by the nucleic acid sequence denoted by SEQ ID NO: 1, which was used in the preparation of the fusion protein constructs exemplified below.

Thus, in this and other embodiments of the presently disclosed subject matter, the fusion protein comprises a TAT domain at its N-terminus and a functional mitochondrial protein at its C-terminus, both covalently linked (fused) to an MTS that is situated between said TAT domain and said functional mitochondrial protein. In other words, the disclosure provides a protein construct comprising an N-terminal TAT fused to N-terminal of MTS fused to N-terminal of functional protein, as schematically presented in FIG. 1.

The fusion protein according to the presently disclosed subject matter may be prepared by any method known to a skilled artisan. By example, the fusion protein as herein defined may be prepared as exemplified below, by standard molecular biology and cloning techniques.

The term "fusion protein" in the context of the invention concerns a sequence of amino acids, predominantly (but not necessarily) connected to each other by peptidic bonds. The term "fused" in accordance with the fusion protein of the invention refers to the fact that the amino acid sequences of at least three different origins, namely, the TAT domain, the sequence of the mitochondrial targeting domain (MTS) and mitochondrial protein, are linked to each other by covalent bonds either directly or via an amino acid linker joining (bridging, conjugating, covalently binding) the amino acid sequences. The fusion may be by chemical conjugation such as by using state of the art methodologies used for conjugating peptides.

The fusion protein in the context of the invention may also optionally comprise at least one linker covalently joining different domains of the fusion protein construct.

The term "linker" in the context of the invention concerns an amino acid sequence of from about 4 to about 20 amino acid residues positioned between the different fusion protein domains and covalently joining them together. For example, a linker in accordance with the invention may be 4, 5, 6, 7, 8, 9, 10, 11, 12, 13, 14, 15, 16, 17, 18, 19 or 20 amino acid long. Linkers are often composed of flexible amino acid residues, for example but not limited to glycine and serine so that the adjacent protein domains are free to move relative to one another. The term "linker" can be interchangeably used with "spacer".

The design of a linker that enables proper folding of the various domains of a protein is well known in the art. A non-binding example of a linker is the amino acid sequence GSDP (Gly-Ser-Asp-Pro) as denoted by SEQ ID NO: 32, which was used in the Examples below to construct the fusion proteins His TAT MTS(cs) 81-210 FRA (denoted by SEQ ID NO: 17), His TAT MTS(fra) 81-210 FRA (denoted by SEQ ID NO: 18), His TAT MTS(lad) 81-210 FRA (denoted by SEQ ID NO: 19) and His TAT MTS(orf) 81-210 FRA (denoted by SEQ ID NO: 20).

Thus in some embodiments the present disclosure relates to a fusion protein as herein defined further comprising a linker covalently linking said TAT domain to said MTS sequence.

The fusion protein in the context of the invention may also optionally comprise at least one methionine (M) residue at its N-terminus, as in the case of the exemplified fusion proteins below. The methionine is positioned N-terminal to the TAT domain.

Fusion may also be achieved by recombinant techniques, i.e. by construction of a nucleic acid sequence coding for the entire the fusion protein (coding for all segments) so that essentially all the bonds are peptidic bonds.

In order to facilitate purification of the protein constructs described herein, fusion protein constructs in accordance with the invention may also comprise an N-terminal tag (e.g. His tag as exemplified below, Glutathione S-transferase (GST), Maltose-Binding Protein (MBP), FLAG octapeptide, to name but few), which may be removed or retained in the final fusion construct. Such tags are normally cleaved off from the fusion protein upon entry to the mitochondria, along with the TAT and MTS sequences.

In some embodiments, the amino acid sequence of a fusion protein according to the invention is as set forth in SEQ ID NO: 17, namely His TAT MTS(cs) FRA, SEQ ID NO: 19, namely His TAT MTS(lad) FRA, as well as in SEQ ID NO: 20, namely, His TAT MTS(orf) FRA.

Fusion protein constructs in accordance with the invention may also be prepared without an N-terminal tag. In some embodiments, the amino acid sequence of a fusion protein according to the invention is as set forth in SEQ ID NO: 28, namely TAT MTS(cs) FRA, SEQ ID NO: 30, namely TAT MTS(lad) FRA, as well as in SEQ ID NO: 31, namely, TAT MTS(orf) FRA.

Therefore the present disclosure further encompasses a fusion protein having the amino acid sequence denoted by SEQ ID NO: 30, comprising a HIV-1 transactivator of transcription (TAT) domain having the amino acid sequence denoted by SEQ ID NO: 27 fused to human frataxin having the amino acid sequence denoted by SEQ ID NO: 26 and a mitochondria targeting sequence (MTS) of human lipoamide dehydrogenase having the amino acid sequence denoted by SEQ ID NO: 24, said MTS situated between said TAT domain and said frataxin and is linked to said TAT domain via a linker having the amino acid sequence denoted by SEQ ID NO: 32, and wherein said frataxin is C-terminal to said MTS of human lipoamide dehydrogenase.

In some embodiments the fusion protein as herein defined has the amino acid sequence denoted by SEQ ID NO: 28, comprising a HIV-1 transactivator of transcription (TAT) domain having the amino acid sequence denoted by SEQ ID NO: 27 fused to human frataxin having the amino acid sequence denoted by SEQ ID NO: 26 and a mitochondria targeting sequence (MTS) of human citrate synthase having the amino acid sequence denoted by SEQ ID NO: 23, said MTS situated between said TAT domain and said frataxin, and is linked to said TAT domain via a linker having the amino acid sequence denoted by SEQ ID NO: 32, and wherein said frataxin is C-terminal to said MTS of human citrate synthase.

The presently disclosed subject matter further provides a composition comprising a physiologically acceptable carrier and as an active ingredient a fusion protein as herein defined.

In specific embodiments the presently disclosed subject matter provides a composition comprising as an active ingredient a fusion protein having the amino acid sequence denoted by SEQ ID NO: 30 or having the amino acid sequence denoted by SEQ ID NO: 28 and a physiologically acceptable carrier.

Also provided by the presently disclosed subject matter is a pharmaceutical composition comprising a pharmaceutically acceptable carrier and as an active ingredient a fusion protein as herein defined.

The "composition" as herein defined generally comprises a buffering agent, an agent which adjusts the osmolarity thereof, and optionally, one or more pharmaceutically (or physiologically) acceptable carriers, diluents, additives and excipients as known in the art. Supplementary active ingredients can also be incorporated into the compositions. The pharmaceutically acceptable carrier can be solvent or dispersion medium containing, for example, water, ethanol, polyol (for example, glycerol, propylene glycol, and liquid polyethylene glycol, and the like), suitable mixtures thereof, and vegetable oils. Each carrier should be physiologically or pharmaceutically acceptable, as the case may be, in the sense of being compatible with the other ingredients and not injurious to the patient.

The additives may be but are not limited to at least one of a protease inhibitor, for example phenylmethanesulfonylfluoride or phenylmethylsulfonyl fluoride (PMSF), Nafamostat Mesylate, 4-(2-Aminoethyl)benzenesulfonyl fluoride hydrochloride (AEBSF), Bestatin, Pepstatin A, E-64, Leupeptin, 1,10-Phenanthroline and any other protease inhibitor known in the art.

The "pharmaceutical compositions" of the presently disclosed subject matter are compositions as described above, comprising pharmaceutically acceptable carriers, diluent, adjuvant and/or excipients and/or additives as known in the art.

The presently disclosed subject matter further provides a pharmaceutical composition as herein defined for treating or alleviating a mitochondrial disorder.

The term "mitochondrial disorder" as encompassed by the presently disclosed subject matter refers to a group of systemic diseases caused by inherited or acquired damage to the mitochondria causing an energy shortage within those areas of the body that consume large amounts of energy such as the liver, muscles, brain, and the heart. The result is often liver failure, muscle weakness, fatigue, and problems with the heart, eyes, and various other systems.

The mitochondrial disorder may be any one of frataxin deficiency which causes or is associated with Friedreich's ataxia; a deficiency in OTC (X-linked recessive genetic disorder caused by non-conservative mutations in the OTC gene; disorder associated with LAD deficiency; or the mitochondrial metabolic disorder is Complex I deficiency (OMIM: 252010). Complex I deficiency can be caused by a mutation in any of the subunits thereof. Alternatively, the Complex I deficiency is caused by a mutation in a gene selected from NDUFV1 (OMIM: 161015), NDUFV2 (OMIM:600532), NDUFS1 (OMIM: 157655), NDUFS2 (OMIM:602985), NDUFS3 (OMIM:603846), NDUFS4 (OMIM:602694), NDUFS6 (OMIM:603848), NDUFS7 (OMIM:601825), NDUFS8 (OMIM:602141), and NDUF A2 (OMIM: 602137).

In other embodiments, the mitochondrial disorder is Complex IV deficiency (cytochrome c oxidase; OMIM:220110). Complex IV deficiency can be caused by a mutation in any of the subunits thereof. In another embodiment, the Complex IV deficiency is caused by a mutation in a gene selected from the group consisting of MTCO1 (0MIM:516030), MTCO2 (0MIM:516040), MTCO3 (0MIM:516050), COX10 (OMIM:602125), COX6B1 (OMIM: 124089), SCO1 (OMIM:603644), FASTKD2 (0MIM:612322), and SCO2 (OMIM:604272).

In other embodiments, the mitochondrial disorder is a neurodegenerative disease. As provided herein, compositions of the present invention exhibit the ability to traverse the blood-brain barrier (BBB).

In further embodiments of the presently disclosed subject matter, the mitochondrial disorder is selected from the group consisting of encephalopathy and liver failure that is accompanied by stormy lactic acidosis, hyperammonemia and coagulopathy. In other embodiments, the mitochondrial disorder is selected from the group consisting of Ornithine Transcarbamoylase deficiency (hyperammonemia) (OTCD), Carnitine O-palmitoyltransferase II deficiency (CPT2), Fumarase deficiency, Cytochrome c oxidase deficiency associated with Leigh syndrome, Maple Syrup Urine Disease (MSUD), Medium-Chain Acyl-CoA Dehydrogenase deficiency (MCAD), Acyl-CoA Dehydrogenase Very Long-Chain deficiency (LCAD), Trifunctional Protein deficiency, Progressive External Ophthalmoplegia with Mitochondrial DNA Deletions (POLG), DGUOK, TK2, Pyruvate Decarboxylase deficiency, and Leigh Syndrome (LS). In another embodiment, the mitochondrial metabolic disorder is selected from the group consisting of Alpers Disease; Barth syndrome; beta-oxidation defects; carnitine-acyl-carnitine deficiency; carnitine deficiency; co-enzyme Q10 deficiency; Complex II deficiency (OMIM:252011), Complex III deficiency (OMIM: 124000), Complex V deficiency (OMIM: 604273), LHON-Leber Hereditary Optic Neuropathy; MM-Mitochondrial Myopathy; LIMM-Lethal Infantile Mitochondrial Myopathy; MMC-Maternal Myopathy and Cardiomyopathy; NARP-Neurogenic muscle weakness, Ataxia, and Retinitis Pigmentosa; Leigh Disease; FICP-Fatal Infantile Cardiomyopathy Plus, a MELAS-associated cardiomyopathy; MELAS-Mitochondrial Encephalomyopathy with Lactic Acidosis and Strokelike episodes; LDYT-Leber's hereditary optic neuropathy and Dystonia; MERRF-Myoclonic Epilepsy and Ragged Red Muscle Fibers; MHCM-Maternally inherited Hypertrophic CardioMyopathy; CPEO-Chronic Progressive External Ophthalmoplegia; KSS-Kearns Sayre Syndrome; DM-Diabetes Mellitus; DMDF Diabetes Mellitus+Deafness; CIPO-Chronic Intestinal Pseudoobstruction with myopathy and Ophthalmoplegia; DEAF-Maternally inherited DEAFness or aminoglycoside-induced DEAFness; PEM-Progressive encephalopathy; SNHL-SensoriNeural Hearing Loss; Encephalomyopathy; Mitochondrial cytopathy; Dilated Cardiomyopathy; GER-Gastro intestinal Reflux; DEMCHO-Dementia and Chorea; AMDF-Ataxia, Myoclonus; Exercise Intolerance; ESOC Epilepsy, Strokes, Optic atrophy, and Cognitive decline; FBSN Familial Bilateral Striatal Necrosis; FSGS Focal Segmental Glomerulosclerosis; LIMM Lethal Infantile Mitochondrial Myopathy; MDM Myopathy and Diabetes Mellitus; MEPR Myoclonic Epilepsy and Psychomotor Regression; MERME MERRF/MELAS overlap disease; MHCM Maternally Inherited Hypertrophic CardioMyopathy; MICM Maternally Inherited Cardiomyopathy; MILS Maternally Inherited Leigh Syndrome; Mitochondrial Encephalocardio myopathy; Multisystem Mitochondrial Disorder (myopathy, encephalopathy, blindness, hearing loss, peripheral neuropathy); NAION Nonarteritic Anterior Ischemic Optic Neuropathy; NIDDM Non-Insulin Dependent Diabetes Mellitus; PEM Progressive Encephalopathy; PME Progressive Myoclonus Epilepsy; RTT Rett Syndrome; SIDS Sudden Infant Death Syndrome; MIDD Maternally Inherited Diabetes and Deafness; and MODY Maturity-Onset Diabetes of the Young, and MNGIE.

Each mitochondrial disease represents an embodiment of the present invention.

In the above and other embodiments, the presently disclosed subject matter provides a pharmaceutical composition as herein defined for use in the treatment of Friedreich's ataxia or any other disorder associated with deficiency of frataxin or defective frataxin or for use in the treatment of a disorder associated with a deficiency of OTC or with defective OTC.

In still further embodiments, the presently disclosed subject matter provides a pharmaceutical composition for the treatment of Friedrich's Ataxia by intravenous administration to a subject in need thereof, said composition comprising a therapeutically effective amount of a fusion protein as herein defined.

In specific embodiments the presently disclosed subject matter provides a pharmaceutical composition for the treatment of Friedrich's Ataxia by intravenous administration to a subject in need thereof, said composition comprising a therapeutically effective amount of a fusion protein having the amino acid sequence denoted by SEQ ID NO: 30 or having the amino acid sequence denoted by SEQ ID NO: 28.

In further specific embodiments the presently disclosed subject matter provides a pharmaceutical composition for the treatment of Friedrich's Ataxia by intravenous administration to a subject in need thereof, said composition comprising a therapeutically effective amount of a fusion protein having the amino acid sequence denoted by SEQ ID NO: 30.

In still further specific embodiments the presently disclosed subject matter provides a pharmaceutical composition for the treatment of Friedrich's Ataxia by intravenous administration to a subject in need thereof, said composition comprising a therapeutically effective amount of a fusion protein having the amino acid sequence denoted by SEQ ID NO: 28.

The presently disclosed subject matter further provides a fusion protein according to the invention for use in a method for the treatment of a mitochondrial disorder.

In the above and other embodiments of the presently disclosed subject matter the functional protein is frataxin or OTC, for use in a method for the treatment of Friedreich's ataxia or any other disorder associated with deficiency of frataxin or defective frataxin or, respectively, a disorder associated with a deficiency of OTC or with defective OTC.

As shown below in Example 5, the inventors have shown that fusion proteins comprising TAT, MTS and frataxin (TAT-MTS-FRA) were able to partially rescue cells obtained from Friedreich's ataxia patients, as well as normal cells, from oxidative stress, exhibiting a clear biological activity of the fusion protein constructs of the presently disclosed subject matter.

L-Buthionine sulphoximine (BSO) is an inhibitor of gamma-glutamylcysteine synthetase (gamma-GCS) and, consequently lowers tissue glutathione (GSH) concentrations. GSH plays an important role in cellular defense against a wide variety of toxic electrophiles via the formation of thioether conjugates. Therefore, BSO was used by the inventors to model oxidative stress, through its ability to inhibit de novo glutathione synthesis, thereby depleting an important component of these cells' intrinsic defenses against reactive oxygen species (ROS) and allowing for the accumulation of ROS produced by natural cell processes, known to result in cell death.

It is known that Friedreich ataxia cells are extremely sensitive to BSO-induced oxidative stress compared with normal cells because they lack Frataxin, and thus are used as an in vitro model of the long-term consequences of absent Frataxin.

As shown in the Examples below, oxidative stress was induced with various concentrations of BSO in cells obtained from patients as well as in normal healthy cells and the effect of the various TAT-MTS-FRA fusion proteins on cell death was measured. As can be seen in FIG. 9, BSO caused cell death of normal lymphocytes as well as of cells obtained from Friedreich ataxia patients. However, cells obtained from patients were more sensitive to BSO-induced oxidative stress, consistent with previous findings. Most importantly, the various TAT-MTS-FRA fusion proteins, which were added a few hours before oxidative stress induction, were demonstrated to partially rescue both normal lymphocytes as well as patients' cells from cell death. This partial rescue was determined by both reduction in cell death and by reduction in caspase 3 activity.

Surprisingly, as also shown in FIG. 9, at least two out of the three fusion proteins carrying a heterologous MTS (namely, MTSorf and MTScs) demonstrated a superior protective effect with respect to the effect demonstrated by the fusion protein carrying the native MTS.

In addition, in an independent comparative experiment shown in FIG. 12, in which the effect of the various TAT-MTS-FRA fusion proteins on oxidative stress was examined, a fusion protein carrying another heterologous MTS, namely, MTSlad also demonstrated a superior protective effect with respect to the effect demonstrated by the fusion protein carrying the native MTS (FIG. 12C).

Thus the presently disclosed subject matter further provides a method for treating or alleviating a mitochondrial disorder, said method comprising the step of administering to a subject in need of such treatment a therapeutically effective amount of the fusion protein as defined herein, thereby treating a mitochondria disorder.

In the above and other embodiments, the method for treating or alleviating a mitochondrial disorder according to the invention is wherein said functional protein is frataxin or OTC, and the mitochondrial disorder is Friedreich's ataxia or any other disorder associated with deficiency of frataxin or defective frataxin or respectively, a disorder associated with a deficiency of OTC or with defective OTC.

The term "treat" or "treatment" or forms thereof as herein defined means to prevent worsening or arrest or alleviate or cure the disease or condition in a subject in need thereof. Thus the term "treatment", "treating" or "alleviating" in the context of the intention does not refers to complete curing of the diseases, as it does not change the mutated genetics causing the disease. This term refers to alleviating at least one of the undesired symptoms associated with the disease, improving the quality of life of the subject, decreasing disease-caused mortality, or (if the treatment in administered early enough) preventing the full manifestation of the mitochondrial disorder before it occurs, mainly to organs and tissues that have a high energy demand. The treatment may be a continuous prolonged treatment for a chronic disease or a single, several or multiple administrations for the treatment of an acute condition such as encephalopathy and liver failure that is accompanied by stormy lactic acidosis, hyperammonemia and coagulopathy.

Notably, in the case of metabolic or mitochondrial disorders there is no need to restore protein activity back to 100%, but rather raise it above a certain energetic threshold which can vary from patient to patient depending on basal protein activity.

In addition, treatment of mitochondrial disorders using replacement therapy is necessarily more complex than replacement of a cytosolic gene product and must consider not only the need to target and cross multiple membranes in mitochondria, but also the fact that many proteins in the mitochondria act as multi-component complexes which require appropriate assembly in order to integrate properly. Additionally, many of the mitochondrial gene defects cause severe neurologic symptoms as the primary or most prominent phenotype, and, as mentioned above, drug delivery across the BBB is difficult.

Therapeutic formulations may be administered in any conventional route and dosage formulation. Formulations typically comprise at least one active ingredient, as defined above, together with one or more acceptable carriers thereof. Thus, administration can be any one of intravenous, intraperitoneal, intramuscular and intratechal administration. Oral administration is also contemplated.

The term "therapeutically effective amount" (or amounts) of the peptide for purposes herein defined is determined by such considerations as are known in the art in order to cure or at least arrest or at least alleviate the medical condition.

In some embodiments the therapeutically effective amount according to the presently disclosed subject matter is between about 0.5 mg/kg to about 2.0 mg/kg body weight of the subject in need thereof which is the Human Equivalent Dose (HED) of an effective amount in mice of between about 7 mg/kg to about 25 mg/kg.

Thus in specific embodiments disclosed is a pharmaceutical composition as herein defined wherein the therapeutically effective amount administered is from about 0.5 mg/Kg to about 2 mg/Kg body weight of said subject.

As used herein, the term "subject in need" is to be taken to mean a human suffering from a mitochondrial disorder as herein defined.

In the above and other embodiments, the method for treating or alleviating a mitochondrial disorder according to the invention further comprises administering an additional therapeutic agent.

The term "additional therapeutic agent" as herein defined refers to any agent that is administered in addition to the fusion protein according to the invention in order to alleviate the symptoms associated with the disease or disorder the treatment of which is desirable. In the above and other embodiments of the disclosed subject matter, the fusion protein of the invention and said additional therapeutic agent are administered simultaneously. Alternatively or additionally, said fusion protein and said additional therapeutic agent are administered at different time points, at different intervals between administrations, for different durations of time, or in a different order.

The disclosed subject matter further provides a method for introducing a functional mitochondrial protein into mitochondria of a subject, said method comprising the step of administering to a subject in need of such treatment a therapeutically effective amount of the fusion protein as defined herein, thereby introducing a functional mitochondrial protein into the mitochondria of a subject in need thereof.

By another one of its aspects, the disclosed subject matter further provides a method for alleviating oxidative stress in a subject in need thereof, said method comprising the step of administering to a subject in need of such treatment a therapeutically effective amount of the fusion protein as herein defined, thereby alleviating oxidative stress in said subject.

The term "oxidative stress" as herein defined refers to an imbalance between the systemic manifestations of reactive oxygen species (ROS) and an ability of a biological system to readily detoxify the reactive intermediates or to repair the resulting damage. Disturbances in the normal redox state of cells can cause toxic effects through the production of peroxides and free radicals that damage all components of the cell. In addition, since some reactive oxidative species act as cellular messengers in redox signaling, accumulation of ROS can cause disruptions in normal mechanisms of cellular signaling. In humans, oxidative stress is thought to be involved in the development of various disorders and conditions, among which are cancer, Parkinson's disease, Alzheimer disease to name but a few.

It is appreciated that certain features of the presently disclosed subject matter, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Unless defined otherwise, all technical and scientific terms used herein have the same meaning as commonly understood by one of ordinary skill in the art to which this invention is related. The following terms are defined for purposes of the invention as described herein.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook & Russell, 2001.

Experimental Procedures

Cell Cultures

Lymphocytes (Lym 43) and fibroblasts (Fib. 78 and Fib. 65) from Friedreich's ataxia patients were obtained from Coriell Cell Repositories (Camden, N.J.) and grown at the recommended medium. Human BJAB cells (EBV-negative Burkitt's lymphoma cells) were grown in RPMI medium supplemented with 20% heat-inactivated fetal calf serum (FCS), 2 mM L-glutamine, 100 U/mL penicillin, and 100 µg/mL streptomycin. Normal lymphocytes [20] were grown in RPMI 1640 supplemented with 10% fetal calf serum (FCS) and antibiotics as above.

Cloning of the Plasmids Encoding the Fusion Proteins
His-TAT-MTSfra-FRA

The plasmid His-TAT-LAD [23] was cut with BamHI and XhoII to remove the LAD sequence, thus obtaining the vector fragment. The full-length frataxin was generated by PCR using a frataxin clone (purchased from Open Biosystem, Ltd., clone no. 4842134) as a template and a pair primers covering the whole sequence, including its native MTS, 5'-CGCG-GATCCGTGGACTCTCGGGCGCCG-3' (forward) and 5'-ACGCTCGAGTCAAGCATCTTTTCCGGAATAGGC-3' (reverse), as denoted by SEQ ID NO: 7 and SEQ ID NO: 8, respectively. The PCR fragment was cut with BamHI and XhoII and ligated with the vector fragment, thus obtaining the plasmid encoding the His-TAT-MTSfra-FRA fusion protein.

His-MTSlad-FRA

The plasmid encoding the His-TAT-MTSfra-FRA was cut with BamHI and BsaI to remove the MTSfra sequence. The MTSlad was obtained by PCR using the plasmid His-TAT-LAD [23] as a template and the following pair of primers: 5'-CGCGGATCCACAGAGCTGGAGTCGTGTGTA-3' (forward) and 5'-CATAGG-TGGTCTCATCTA-GAGAGAGCCTGGGTGGCCCAAAGTTCCA-GATGCGTAAGTTCT CAGAGGCA-3' (reverse) as denoted by SEQ ID NO: 9 and SEQ ID NO: 10, respectively. The PCR product was cut with BamHI and BsaI and ligated to the vector fragment thus obtaining the plasmid encoding the His-TAT-MTSlad-FRA fusion protein.

His-TAT-MTSorf-FRA

The plasmid encoding the His-TAT-MTSfra-FRA was cut with BamHI and BsaI to remove the MTSfra sequence. The MTSorf was obtained by PCR using the plasmid His-TAT-ORF as a template and the following pair of primers: 5'-CGCGGATCCGGGAGCACTAGTGATTCGC-3' (forward) and 5'-CATAGGTG GTCTCATCTAGAGAGC-CTGGGTGGCCCAAAGTTCCAGAAGAGGGGTGTCTG GGAGCGA-3' (reverse), as denoted by SEQ ID NO: 11 and SEQ ID NO: 12, respectively. The PCR product was cut with BamHI and BsaI and ligated to the vector fragment thus obtaining the plasmid encoding the His-TAT-MTSorf-FRA fusion protein.

His-TAT-MTScs-FRA

The plasmid encoding the His-TAT-MTSfra-FRA was cut with BamHI and BsaI to remove the MTSfra sequence. The MTScs was generated by synthesizing two oligonucleotides covering the MTScs sequence and the BamHI and BsaI sites at the ends: 5'-GATCCGGCTTTACTTACTGCGGCCGC- CCGGCTCTTGGGAACCAAGAATGCATCTTGTCTTGTTCTTGCAGCCCGGCATGCCAGTTCTGGAACTTTGGGCCACCCAGGCTCTC-3' (forward) and 5'-TCTAGAGAGCCTGGGTGGCCCAAAGTTCCAGAACTGGCATGCCGGGCTGCAAGAACAAGACAAGATGCATTCTTGGTTCCCAAGAGCCGGGCGGCCGCAGTAAGTAAAGCCG-3' (reverse), as denoted by SEQ ID NO: 13 and SEQ ID NO: 14, respectively. The oligonucleotides were ligated to the vector fragment thus obtaining the plasmid encoding the His-TAT-MTScs-FRA fusion protein. All plasmids were confirmed by restriction enzymes and sequencing analyses.

TABLE 1

Nucleic acid and Amino acid sequences

| SEQ ID NO: | Sequence | Name |
|---|---|---|
| 1 | aggaagaagcggagacagcgacgaaga | Sequence encoding TAT fragment |
| 2 | TGGACTCTCGGGCGCCGCgcagtagccggcctcctggcgtcacccagcccggcccaggcccagaccctcacccgggtcccgcggccggcagagttggccccactctgcggccgccgtggcctgcgcaccgacatcgatgcgacctgcacgccccgccgcgcaagttcgaaccaacgtggcctcaaccagatttggaatgtcaaaaagcagagtgtctatttgatgaattttgaggaaa | MTSfra |
| 3 | GCTTTACTTACTGCGGCCGCCCGGCTCTTGGGAACCAAGAATGCATCTTGTCTTGTTCTTGCAGCCCGGCATGCCAGT | MTScs |
| 4 | ggagcactagtgattcgcggtatcaggaatttcaacctagagaaccgagcggaacgggaaatcagcaagatgaagccctctgtcgctcccagacacccctct | MTSorf |
| 5 | cagagctggagtcgtgtgtactgctccttggccaagaggccatttcaatcgaatatctcatggcctacagggactttctgcagtgcctctgagaacttacgca | MTSlad |
| 6 | tctggaactttgggccacccaggctctctagatgagaccacctatgaaagactagcagaggaaacgctggactcttagcagagttttttgaagaccttgcagacaagccatacacgtttgaggactatgatgtctcctttgggagtggtgtcttaactgtcaaactgggtggagatctaggaacctatgtgatcaacaagcagacgccaaacaagcaaatctggctatcttctccatccagtggacctaagcgttatgactggactgggaaaaactgggtgtactcccacgacggcgtgtccctccatgagctgctggccgcagagctcactaaagccttaaaaaccaaactggacttgtcttCCTTGGCCTATTCCGGAAAAGATGCTTGA | Mature Frataxin (FRA) |
| 7 | CGCGGATCCGTGGACTCTCGGGCGCCG | forward primer for precursor frataxin cloning |
| 8 | ACGCTCGAGTCAAGCATCTTTTCCGGAATAGGC | reverse primer for precursor frataxin cloning |
| 9 | CGCGGATCCACAGAGCTGGAGTCGTGTGTA | forward primer for MTS lad cloning |
| 10 | CATAGGTGGTCTCATCTAGAGAGCCTGGGTGGCCCAAAGTTCCAGATGCGTAAGTTCTCAGAGGCA | reverse primer for MTS lad cloning |
| 11 | CGCGGATCCGGGAGCACTAGTGATTCGC | forward primer for MTS orf cloning |

TABLE 1-continued

Nucleic acid and Amino acid sequences

| SEQ ID NO: | Sequence | Name |
|---|---|---|
| 12 | CATAGGTGGTCTCATCTAGAGAGCCTGGGTGGCCCAAA GTTCCAGAAGAGGGGTGTCTGGGAGCGA | reverse primer for MTS orf cloning |
| 13 | GATCCGGCTTTACTTACTGCGGCCGCCCGGCTCTTGGG AACCAAGAATGCATCTTGTCTTGTTCTTGCAGCCCGGC ATGCCAGTTCTGGAACTTTGGGCCACCCAGGCTCTC | forward oligo for MTS cs cloning |
| 14 | TCTAGAGAGCCTGGGTGGCCCAAAGTTCCAGAACTGGC ATGCCGGGCTGCAAGAACAAGACAAGATGCATTCTTGG TTCCCAAGAGCCGGGCGGCCGCAGTAAGTAAAGCCG | reverse primer for MTS cs cloning |
| 15 | CTGAAGGGCCGTGACCTTCTCACTCTAAGAAACTTTAC CGGAGAAGAAATTAAATATATGCTATGGCTATCAGCAG ATCTGAAATTTAGGATAAAACAGAAAGGAGAGTATTTG CCTTTATTGCAAGGGAAGTCCTTAGGCATGATTTTTGA GAAAAGAAGTACTCGAACAAGATTGTCTACAGAAACAG GCTTTGCACTTCTGGGAGGACATCCTTGTTTTCTTACC ACACAAGATATTCATTTGGGTGTGAATGAAAGTCTCAC GGACACGGCCCGTGTATTGTCTAGCATGGCAGATGCAG TATTGGCTCGAGTGTATAAACAATCAGATTTGGACACC CTGGCTAAAGAAGCATCCATCCCAATTATCAATGGGCT GTCAGATTTGTACCATCCTATCCAGATCCTGGCTGATT ACCTCACGCTCCAGGAACACTATAGCTCTCTGAAAGGT CTTACCCTCAGCTGGATCGGGGATGGGAACAATATCCT GCACTCCATCATGATGAGCGCAGCGAAATTCGGAATGC ACCTTCAGGCAGCTACTCCAAAGGGTTATGAGCCGGAT GCTAGTGTAACCAAGTTGGCAGAGCAGTATGCCAAAGA GAATGGTACCAAGCTGTTGCTGACAAATGATCCATTGG AAGCAGCGCATGGAGGCAATGTATTAATTACAGACACT TGGATAAGCATGGGACAAGAAGAGGAGAAGAAAAAGCG GCTCCAGGCTTTCCAAGGTTACCAGGTTACAATGAAGA CTGCTAAAGTTGCTGCCTCTGACTGGACATTTTTACAC TGCTTGCCCAGAAAGCCAGAAGAAGTGGATGATGAAGT CTTTTATTCTCCTCGATCACTAGTGTTCCCAGAGGCAG AAAAACAGAAAGTGGACAATCATGCTGTCATGGTGTCC CTGCTGACAGATTACTCACCTCAGCTCCAGAAGCCTAA ATTTTGA | Mature OTC |
| 16 | ATGTACCGCTACCTGGCCAAAGCGCTGCTGCCGTCCCG GGCCGGGCCCGCTGCCCTGGGCTCCGCGGCCAACCACT CGGCCGCGTTGCTGGGCCGGGGCCGCGGACAGCCCGCC GCCGCCTCGCAGCCGGGGCTCGCATTGGCCGCCCGGCG CCACTAC | MTS of human mitochon. GLUD2 |
| 17 | MGSSHHHHHHSSGLVPRGSHMRKKRRQRRRGSDPALLT AAARLLGTKNASCLVAARHASSGTLGHPGSLDETTYE RLAEETLDSLAEFFEDLADKPYTFEDYDVSFGSGVLTV KLGGDLGTYVINKQTPNKQIWLSSPSSGPKRYDWTGKN WVYSHDGVSLHELLAAELTKALKTKLDLSSLAYSGKDA | His TAT MTS(cs) 81-210 FRA |
| 18 | MGSSHHHHHHSSGLVPRGSHMRKKRRQRRRGSDPWTLG RRAVAGLLASPSPAQAQTLTRVPRPAELAPLCGRRGLR TDIDATCTPRRASSNQRGLNQIWNVKKQSVYLMNLRKS GTLGHPGSLDETTYERLAEETLDSLAEFFEDLADKPYT FEDYDVSFGSGVLTVKLGGDLGTYVINKQTPNKQIWLS SPSSPGKRYDWTGKNWVYSHDGVSLHELLAAELTKALK TKLDLSSLAYSGKDA | HTFrataxin [His TAT MTS(fra) 81-210 FRA] |
| 19 | MGSSHHHHHHSSGLVPRGSHMRKKRRQRRRGSDPQSWS RVYCSLAKRGHFNRISHGLQGLSAVPLRTYASGTLGHP GSLDETTYERLAEETLDSLAEFFEDLADKPYTFEDYDV SFGSGVLTVKLGGDLGTYVINKQTPNKQIWLSSPSSGP KRYDWTGKNWVYSHDGVSLHELLAAELTKALKTKLDLS SLAYSGKDA | His TAT MTS(lad) 81-210 FRA |

TABLE 1-continued

Nucleic acid and Amino acid sequences

| SEQ ID NO: | Sequence | Name |
|---|---|---|
| 20 | MGSSHHHHHHSSGLVPRGSHMRKKRRQRRRGSDPGALV IRGIRNFNLENRAEREISKMKPSVAPRHPSSGTLGHPG SLDETTYERLAEETLDSLAEFFEDLADKPYTFEDYDVS FGSGVLTVKLGGDLGTYVINKQTPNKQIWLSSPSSGPK RYDWTGKNWVYSHDGVSLHELLAAELTKALKTKLDLSS LAYSGKDA | His TAT MTS(orf) 81-210 FRA |
| 21 | YGRKKRRQRRR | TAT |
| 22 | WTLGRRAVAGLLASPSPAQAQTLTRVPRPAELAPLCGR RGLRTDIDATCTPRRASSNQRGLNQIWNVKKQSVYLMN LRK | MTS (fra) |
| 23 | ALLTAAARLLGTKNASCLVLAARHAS | MTS (cs) |
| 24 | QSWSRVYCSLAKRGHFNRISHGLQGLSAVPLRTYA | MTS (lad) |
| 25 | GALVIRGIRNFNLENRAEREISKMKPSVAPRHPS | MTS (orf) |
| 26 | SGTLGHPGSLDETTYERLAEETLDSLAEFFEDLADKP YTFEDYDVSFGSGVLTVKLGGDLGTYVINKQTPNKQI WLSSPSSGPKRYDWTGKNWVYSHDGVSLHELLAAELT KALKTKLDLSSLAYSGKDA | Mature frataxin |
| 27 | RKKRRQRRR | TAT fragment |
| 28 | MRKKRRQRRRGSDPALLTAAARLLGTKNASCLVLAARH ASSGTLGHPGSLDETTYERLAEETLDSLAEFFEDLADK PYTFEDYDVSKGSGVLTVKLGGDLGTYVINKQTPNKQI WLSSPSSGPKRYDWTGKNWVYSHDGVSLHELLAAELTK ALKTKLDLSSLAYSGKDA | TAT MTS(cs) 81-210 FRA |
| 29 | MRKKRRQRRRGSDPWTLGRRAVAGLLASPSPAQAQTLT RVPRPAELAPLCGRRGLRTDIDATCTPRRASSNQRGLN QIWNVKKQSVYLMNRKSGTLGHPGSLDETTYERLAEET LDSLAEFFEDLADKPYTFEDYDVSFGSGVLTVKLGGDL GTYVINKQTPNKQIWLSSPSSGPKRYDWTGKNWVYSHD GVSLHELLAAELTKALKTKLDLSSLAYSGKDA | TAT MTS(fra) 81-210 FRA |
| 30 | MRKKRRQRRRGSDPQSWSRVYCSLAKRGHFNRISHGLQ GLSAVPLRTYASGTLGHPGSLDETTYERLAEETLDSLA EFFEDLADKPYTFEDYDVSFGSGVLTVKLGGDLGTYVI NKQTPNKQIWLSSPSSGPKRYDWTGKNWVYSHDGVSLH ELLAAELTKALKTKLDLSSLAYSGKDA | TAT MTS(lad) 81-210 FRA |
| 31 | MRKKRRQRRRGSDPGALVIRGIRNFNLENRAEREISKM KPSVAPRHPSSGTLGHPGSLDETTYERLAEETLDSLAE FFEDLADKPYTFEDYDVSFGSGVLTVKLGGDLGTYVIN KQTPNKQIWLSSPSSGPKRYDWTGKNWVYSHDGVSLHE LLAAELTKALKTKLDLSSLAYSGKDA | TAT MTS(orf) 81-210 FRA |
| 32 | GSDP | linker |
| 33 | MRKKRRQRRRALLTAAARLLGTKNASCLVLAARHASSG TLGHPSHSLDETTYERLAEETLDSLAEFFEDLADKPYT FEDYDVSFGSGVLTVKLGGDLGTYVINKQTPNKQIWLS SPSSGPKRYDWTGKNWVYSHDGVSLHELLAAELTKALK TKLDLSSLAYSGKDA | TAT MTS(cs) 81-210 FRA Δ linker |
| 34 | MRKKRRQRRRWTLGRRAVAGLLASPSPAQAQTLTRVPR PAELAPLCGRRGLRTDIDATCTPRRASSNQRGLNQIWN VKKQSVYLMNLRKSGTLGHPGSLDETTYERLAEETLDS LAEFFEDLADKPYTFEDYDVSFGSGVLTVKLGGDLGTY VINKQTPNKQIWLSSPSSGPKRYDWTGKNWVYSHDGVS LHELLAAELTKALKTKLDLSSLAYSGKDA | TAT MTS(fra) 81-210 FRA Δ linker |
| 35 | MRKKRRQRRRQSWSRVYCSLAKRGHFNRISHGLQGLSA VPLRTYASGTLGHPGSLDETTYERLAEETLDSLAEFFE DLADKPYTFEDYDVSFGSGVLTVKLGGDLGTYVINKQT PNKQIWLSSPSSGPKRYDWTGKNWVYSHDGVSLHELLA AELTKALKTKLDLSSLAYSGKDA | TAT MTS(lad) 81-210 FRA Δ linker |

TABLE 1-continued

Nucleic acid and Amino acid sequences

| SEQ ID NO: | Sequence | Name |
|---|---|---|
| 36 | MRKKRRQRRRGALVIRGIRNFNLENRAEREISKMKPSV APRHPSSGTLGHPGSLDETTYERLAEETLDSLAEFFED LADKPYTFEDYDVSFGSGVLTVKLGGDLGTYVINKQTP NKQIWLSSPSSGPKRYDWTGKNWVYSHDGVSLHELLAA ELTKALKTKLDLSSLAYSGKDA | TAT MTS(orf) 81-210 FRA Δ linker |

Table 1 above summarizes the nucleic acid sequences of the primers used as described above (i.e. the primers denoted by SEQ ID NOs: 7-14), the amino acid sequence of the TAT domain (denoted by SEQ ID NO: 21), the amino acid sequence of a fragment of the TAT domain used in the present disclosure (denoted by SEQ ID NO: 27) and the nucleic acid sequence encoding therefor (denoted by SEQ ID NO: 1), the amino acid sequences of the various MTSs, namely MTS fra, MTS cs, MTS orf and MTS lad (denoted by SEQ ID NO: 22, SEQ ID NO: 23, SEQ ID NO: 25 and SEQ ID NO: 24, respectively) and the nucleic acid sequences encoding therefor (denoted by SEQ ID NO: 2, SEQ ID NO: 3, SEQ ID NO: 4 and SEQ ID NO: 5, respectively), the amino acid sequence of mature frataxin (denoted by SEQ ID NO: 26) and the nucleic acid sequence encoding therefor (denoted by SEQ ID NO: 6), as well as the nucleic acid sequences encoding the OTC protein and the MTS of human mitochondrial GLUD2 (denoted by SEQ ID NO: 15 and SEQ ID NO: 16, respectively). A four-amino acid long linker, having the amino acid sequence of GSDP is also listed in Table 1 above and denoted by SEQ ID NO: 32.

In addition Table 1 above indicates the amino acid sequences of the various His TAT MTS 81-210 FRA constructs, which comprise the mature frataxin, namely, His TAT MTS(cs) 81-210 FRA, His TAT MTS(fra) 81-210 FRA (also denoted herein as "HTFrataxin"), His TAT MTS(lad) 81-210 FRA and His TAT MTS(orf) 81-210 FRA (denoted by SEQ ID NO: 17, SEQ ID NO: 18, SEQ ID NO: 19 and SEQ ID NO: 20, respectively). The various His TAT MTS 81-210 FRA constructs denoted by SEQ ID NO: 17, SEQ ID NO: 18, SEQ ID NO: 19 and SEQ ID NO: 20 all comprise a short peptide linker denoted by SEQ ID NO: 32, which joins the TAT and MTS domains.

Table 1 above further indicates the amino acid sequences of the various fusion constructs constructed without a His tag at their N-termini and with a short peptide linker denoted by SEQ ID NO: 32, which joins the TAT and MTS domains. These constructs comprise TAT, a linker, MTS and mature frataxin (81-210 FRA), namely TAT MTS(cs) 81-210 FRA, TAT MTS(fra) 81-210 FRA, TAT MTS(lad) 81-210 FRA and TAT MTS(orf) 81-210 FRA, denoted by SEQ ID NO: 28, SEQ ID NO: 29, SEQ ID NO: 30 and SEQ ID NO: 31, respectively.

In addition Table 1 above indicates the amino acid sequences of the various fusion constructs constructed without a His tag and without a linker. These fusion constructs comprise TAT, MTS and mature frataxin (81-210 FRA), namely TAT MTS(cs) 81-210 FRA A linker, TAT MTS(fra) 81-210 FRA A linker, TAT MTS(lad) 81-210 FRA A linker and TAT MTS(orf) 81-210 FRA A linker, denoted by SEQ ID NO: 33, SEQ ID NO: 34, SEQ ID NO: 35 and SEQ ID NO: 36, respectively.

Proteins Expression and Purification

*E. coli* BL21-CodonPlus (λDE3) or HMS competent cells transformed with plasmids encoding the fusion proteins were incubated at 37° C. in a saline lactose broth (SLB medium) containing kanamycine (50 μg/ml), tetracycline (12.5 μg/ml) and chloramphenicol (34 μg/ml). At an $OD_{600}$ of 0.2-0.3, 0.1% glycerol and 0.1 mM potassium glutamate were added to the culture which was then heat-shocked for 20-30 min at 42° C., after which the bacteria were grown at 37° C. until an $OD_{600}$ of 0.8. Protein expression was induced by adding isopropyl-beta-D-thiogalactopyranoside (IPTG, for final concentrations see Table 2 below). After 18 hrs of incubation at 22° C., the cells were harvested by centrifugation (500 g for 15 min at 4° C.).

For the purification procedure, bacteria pellets from 0.5 L culture of expressed cells were sonicated in binding buffer (PBS, pH 7.4, 0.4 M NaCl, 10% Glycerol, 1 mM phenylmethylsulphonylfluoride (PMSF) and 30 mM imidazole (Sigma-Aldrich, St. Louis, Mo., USA)). The suspensions were clarified by centrifugation (35,000 g for 30 min at 4° C.), and the supernatants containing the fusion proteins were purified under native conditions, using binding buffer pre-equilibrated HiTrap Chelating HP columns (Amersham-Pharmacia Biotech, Uppsala, Sweden). Columns were washed by stepwise addition of increasing imidazole concentrations. Finally, the target proteins were eluted with elution buffer (PBS, pH 7.4, 0.4 M NaCl, 10% Glycerol, 250 mM imidazole). All purification procedures were carried out using the FPLC system AKTA (Amersham-Pharmacia Biotech). Imidazole, NaCl and glycerol were removed by transferring the purified proteins to PBS using PD-10 desalting columns (GE Healthcare, Piscataway, N.J., USA). Aliquots of the proteins were kept frozen at −80° C. until use.

TABLE 2

Expression conditions of TAT-MTS-FRA fusion proteins

| Protein | Bacterial Host | Heat Shock | Temp. for induction | IPTG (mM) |
|---|---|---|---|---|
| TAT-MTSfra-FRA | codonPlus | yes | 22° C. over night | 0.5 |
| TAT-MTScs-FRA | codonPlus | yes | 22° C. over night | 0.5 |
| TAT-MTSorf-FRA | HMS | yes | 22° C. over night | 1.0 |
| TAT-MTSlad-FRA | HMS | yes | 22° C. over night | 1.0 |

Characterization of the Fusion Proteins
Determination of Protein Concentration

Protein concentration was measured according to the Bradford method, using the Bradford reagent and the standard curve of BSA. Protein concentration was determined at a wavelength of 595 nm.

Separation of Proteins by Electrophoresis

Samples from the various protein fractions (5-20 μg protein/lane) were loaded on 12% or 15% (w/v) SDS-PAGE gels. The separation of proteins was done using Sturdier Slab Gel Electrophoresis apparatus according to the manufacturer's instructions (Hoefer Sci Instruments, San Francisco, Calif., USA).

Western Blot Analysis

Proteins (5-20 μg protein/lane) were resolved on 12%-15% SDS-PAGE gels and transferred onto an Immobilon-P Transfer membrane (Millipore, Bradford, Pa., USA). Western blot analysis was performed using either anti-frataxin (Abcam), or anti-His (Amersham-Pharmacia Biotech) antibodies at dilutions of 1:600 and 1:30,000, respectively, to identify the relevant proteins. Primary antibody binding was detected by blotting with a suitable secondary antibody conjugated to horseradish peroxidase (HRP) (1:10,000). Band visualization was done using an enhanced chemiluminescence kit (EZ-ECL, Biological Industries, Beit-Haemek, Israel).

BSO Experiments for Inducing Oxidative Stress

Normal or patients' lymphocytes ($4\times10^3$ cells/1001) were seeded in DMEM medium without phenol red and sodium pyruvate (experimental medium) and after 3-4 hr the tested TAT-MTS-FRA fusion protein (at a final concentration of 0.1 μg/μl) was added to the cells for 5 or 24 hr. Following the incubation time with the fusion protein, L-Buthionine-sulfoximine (BSO, Sigma B2640) at different concentrations was added for an additional period of 48 hr. At the end of the incubation time, cell cultures were subjected to cell viability assays, using the CellTiter-Blue™ kit (Promega, Madison, Wis.) according to manufacturer's instructions. In experiments conducted in fibroblasts, cells ($3\times10^3$ cells/100 μl) were seeded in the growth medium and left for 24 hr to allow the cells to adhere. After 24 hr, the medium was changed to the experimental medium and the experiment was continued as described for lymphocytes above.

In Vitro Caspase 3 Activity Assay

Caspase 3 activity within the cells was assessed by using the Apo-ONE Homogeneous Caspase 3/7 Assay Kit (Promega). Caspase 3 activity assays were carried in parallel to cell viability assays.

Example 1

Cloning of Plasmids Encoding TAT-MTS-FRA Fusion Proteins

Expression plasmids encoding the TAT-fusion proteins were cloned and prepared by standard molecular biology tools known in the art. For a general reference see Molecular Cloning: A Laboratory manual (2001) Joseph Sambrook and David William Russell. TAT [9] having the amino acid sequence as denoted by SEQ ID NO: 27 (encoded by the nucleic acid sequence denoted by SEQ ID NO: 1) was fused (N-terminal) to the mature human frataxin protein (having the amino acid sequence as denoted by SEQ ID NO: 26 and encoded by the nucleic acid sequence as denoted by SEQ ID NO: 6).

Various fusion constructs were prepared, which differ in their mitochondrial targeting sequence present at the N terminus of human frataxin (and thus located between TAT and mature human frataxin), being either the native mitochondrial targeting sequence of frataxin (referred to herein as MTSfra, having the amino acid sequence as denoted by SEQ ID NO: 22) or other defined MTSs of human mitochondrial proteins, including lipoamide dehydrogenase (referred to herein as MTSlad, having the amino acid sequence as denoted by SEQ ID NO: 24), C6ORF66 (referred to herein as MTSorf, having the amino acid sequence as denoted by SEQ ID NO: 25) and citrate synthase (referred to herein as MTScs, having the amino acid sequence as denoted by SEQ ID NO: 23). The various TAT-MTS-FRA fusion proteins are summarized in Table 3 below and schematically presented in FIG. 1.

All plasmids were cloned with His-tag at the 5'-terminus of the coding sequence and all coding sequences were under the control of the T7 promotor. All clones were confirmed by restriction enzymes and sequencing analyses.

TABLE 3

| The cloned plasmids | | |
| --- | --- | --- |
| No. | Plasmid name | Abbreviated name |
| 1 | His-TAT-MTSfra-FRA | FRA |
| 2 | His-TAT-MTSlad-FRA | (LAD)FRA |
| 3 | His-TAT-MTSorf-FRA | (ORF)FRA |
| 4 | His-TAT-MTScs-FRA | (CS)FRA |

Abbreviations: lad, Lipoamide dehydrogenase protein (E3 subunit); orf, C6ORF66 assembly factor; and cs, citrate synthase.

As indicated above, the amino acid sequences of the proteins obtained from the constructs indicated as 1-4 in Table 3 above are denoted by SEQ ID NO: 18, SEQ ID NO: 19, SEQ ID NO: 20 and SEQ ID NO: 17, respectively.

Example 2

Expression of the Fusion Proteins in E. coli Hosts

Expression of the fusion proteins was performed in E. coli hosts and was calibrated for optimal expression conditions. As known in the art, there are several different bacterial expression systems. Successful expression of recombinant proteins is often dependent on the strain of the bacteria expression system used. Thus, for each fusion protein prepared as described above, four different E. coli bacterial stains were tested: BL21-CodonPlus, BL21, Rosetta and HMS and the host for expression was thereby selected. The conditions for expression were also calibrated for each of the TAT-fusion proteins, by changing several parameters, including the concentration of the inducer (IPTG) and length of induction growth conditions (i.e. temperature, addition of chemicals, etc.)

Upon expression, bacterial cells were disrupted and cellular sub-fractions were prepared, separating the soluble and non-soluble fractions. Analysis was performed for the whole-cell bacteria (W.C or whole-cell extract), the soluble fraction (Sol) and insoluble fraction (Insol) on sodium dodecyl sulfate polyacrylamide gel electrophoresis (SDS-PAGE) gels in order to examine whether the fusion protein was expressed and at which sub-cellular fraction it accumulates. The goal was to obtain high expression levels of the different TAT-fusion proteins in the soluble sub-fraction of the expressing bacteria, for future purification. The different TAT-fusion proteins were also characterized by Western blots analyses using both anti-His and anti-frataxin antibodies. Table 2 above summarizes the bacterial host, IPTG concentration and temperature for production of each TAT-MTS-FRA fusion proteins carrying a different MTS sequence.

Figure 2D:
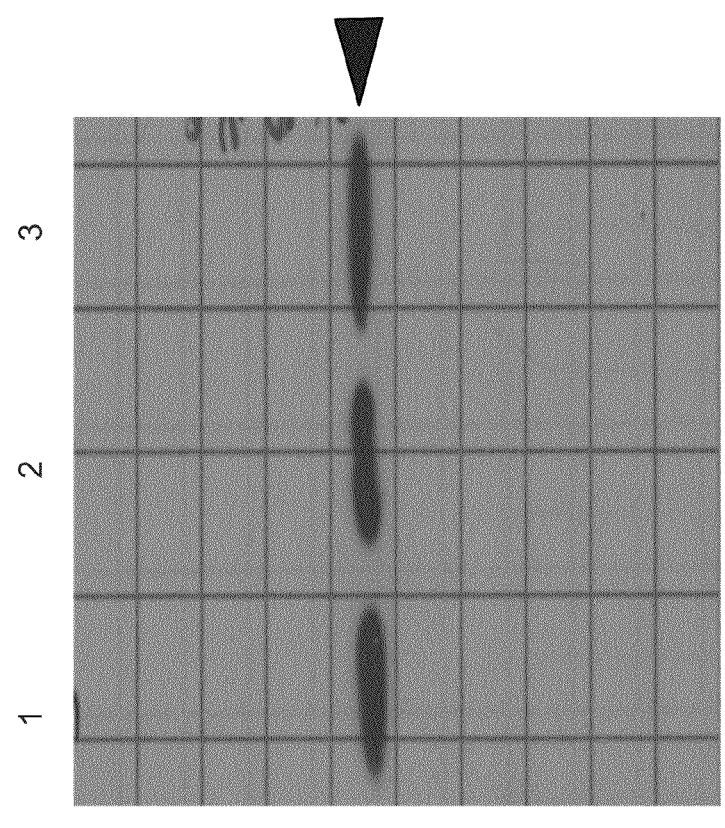
Figure 2C:
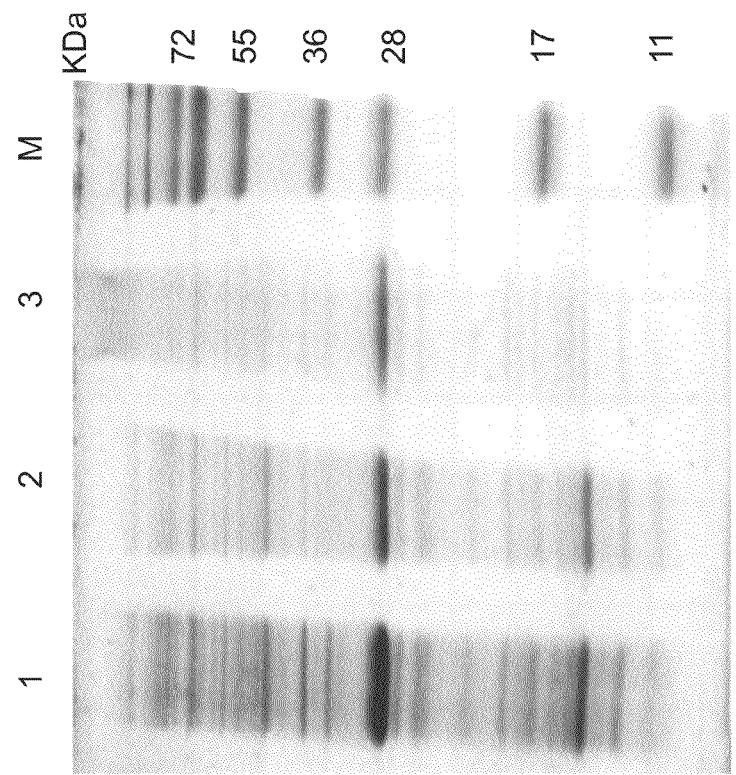

Typical expression and sub-cellular localization of each of the four fusion proteins as characterized by SDS-PAGE gels and Western blots using anti-His antibodies are demonstrated in FIG. 2 and in FIG. 3. Expression of the His-TAT-MTSfra-FRA fusion protein is shown in FIG. 2A-B, Expression of the His-TAT-MTSorf-FRA fusion protein is shown in FIG. 2C-D, Expression of the His-TAT-MTSlad-FRA fusion protein is shown in FIG. 3A-B and Expression of the His-TAT-MTScs-FRA fusion protein is shown in FIG. 3C-D. These experiments confirmed the full-length expression of the different TAT-fusion proteins and their identity.

It should be pointed out the anti-His antibodies recognize, most probably, the various fusion proteins with different efficacy, depending on the exposure or availability of the His sequence in the final protein preparation, for antibody interactions. Thus, expression levels of the various fusion proteins are determined based on the SDS-PAGE gels.

As can be seen in FIG. 2 and in FIG. 3, the TAT-MTSfra-FRA fusion protein (FIG. 2A & FIG. 2B) was expressed at low levels in the bacterial hosts, as compared to the other three fusion proteins carrying an heterologous MTS (FIG. 2C & FIG. 2D and FIG. 3A-D), even under the best calibrated conditions. Thus, using a heterologous MTS instead of the native frataxin-MTS has an advantage in its expression levels in a bacterial host. This has major implications on its future development for human use, where large quantities of the fusion protein are needed to be produced (see also below).

Example 3

Purification of the TAT-MTS-FRA Fusion Proteins

The soluble fractions of the expressed TAT-MTS-FRA fusion proteins were loaded onto a nickel-chelating column to affinity-purify these proteins, as detailed above. Calibration experiments were performed for each of the fusion proteins, including specific conditions for binding of the fusion protein onto the affinity column, its elution and removal of the imidazole from the final protein preparations. One typical purification run of each of the fusion proteins is demonstrated in FIG. 4 (for His-TAT-MTSfra-FRA and His-TAT-MTSorf-FRA) and in FIG. 5 (for His-TAT-MTSlad-FRA and His-TAT-MTScs-FRA).

As shown in FIG. 6A, eluted proteins showed a major band of the expected size (approximately 20-27 kDa) and were >95% pure, as determined by SDS-PAGE analysis and by Western blot analyses using both anti-His (FIG. 6B) and anti-Fra antibodies (FIG. 6C). As can be seen in FIG. 6, TAT-MTS-FRA fusion proteins carrying a heterologous MTS were full-length, intact proteins with no evidence for protein degradation. However, TAT-MTSfra-FRA carrying the native MTS sequence was partially degraded (see lane 1 in FIG. 6B and in FIG. 6C). Thus, using a heterologous MTS sequence for the TAT-FRA fusion protein has an advantage also for keeping the fusion protein intact and stable.

In addition, when comparing the total amounts and concentrations of each of the fusion proteins, which were produced from the same starting volume of bacterial cultures, fusion proteins carrying an heterologous MTS were produced in larger amounts and at higher concentration as compared to that of fusion protein carrying the native MTS (Table 4, below). This has again major implications on its future development for human use, where large quantities of the fusion protein are needed and at high concentrations. Moreover, the stability of the produced fusion protein has an additional advantage.

TABLE 4

| TAT-MTS-FRA fusion proteins | | |
|---|---|---|
| Protein | Final concentration (mg/ml) | Amount purified from 0.5L bacterial culture (mg) |
| TAT-MTSfra-FRA | 0.2 | 0.6-0.7 |
| TAT-MTScs-FRA | 1.0 | 3-4 |

TABLE 4-continued

| TAT-MTS-FRA fusion proteins | | |
|---|---|---|
| Protein | Final concentration (mg/ml) | Amount purified from 0.5L bacterial culture (mg) |
| TAT-MTSorf-FRA | 1.0 | 3-4 |
| TAT-MTSlad-FRA | 0.8 | 2.4-3.2 |

Example 4

Internalization of TAT-MTS-FRA Fusion Proteins

In order to test the ability of the fusion protein to reach the mitochondria within intact cells, human BJAB cells were incubated with one of the purified fusion proteins, namely, TAT-MTSlad-FRA. After incubation, sub-cellular fractions were prepared, to separate the mitochondria and the cytosol. The mitochondria were then treated with proteinase K to digest proteins nonspecifically adsorbed to the outer membrane, thereby ensuring that the mitochondrial extract represented only proteins within the mitochondria. Samples were then analyzed by Western blot assay for the presence of the FRA-based fusion protein, using both anti-His and anti-FRA antibodies (see FIG. 7).

As shown in FIG. 7, using anti-His antibodies the results indicated the presence of the His-tagged TAT-MTSlad-FRA fusion protein within the mitochondrial fractions of the treated cells after 1 and 5 hours of incubation (lanes 4 and 6 & 7, respectively). Using anti-FRA antibodies, from lane 2 of FIG. 7B it is evident that control cells, not treated with the fusion protein have the endogenous FRA protein, most probably, both the mature isoform (81-210 aa; ~14.3 KDa) and the intermediate isoform (42-210 aa; ~8.6 KDa) (lower and upper band in lane 2, respectively). As shown in FIG. 7B (lanes 4, 6, 7), upon treatment with the TAT-MTSlad-FRA fusion protein, the relative amounts of both the unprocessed fusion protein and the mature protein, increases with the incubation time (FIG. 7B; upper and lower bands, respectively).

The antibodies used to detect the proteins in the internalization assay presented in FIG. 7 were polyclonal antibodies directed against human frataxin. These antibodies recognize the full-length, unprocessed human frataxin very well, as well as its processed products. In FIG. 8 referred to below, detection was performed using monoclonal antibodies specifically directed against the C-terminus of the frataxin protein. As these monoclonal antibodies are less efficient in recognizing the protein, particularly at the amounts of protein detected in FIG. 8, the results of FIGS. 7 and 8 cannot be compared.

Internalization of fusion proteins comprising frataxin into the mitochondria of cells was examined also for other TAT-MTS-FRA fusion proteins, namely, TAT-MTSfra-FRA, TAT-MTScs-FRA, and TAT-MTSorf-FRA (as well as for TAT-MTSlad-FRA), as shown in FIG. 8A. Cells were incubated for 3 hours with each of the TAT-MTS-FRA fusion proteins (at a final concentration of 0.02 μg/μl). The cells were then washed, their mitochondria were isolated and then submitted to Western blot analysis using monoclonal anti-FRA antibodies (Abnova, Taiwan; 1 μg/ml) that are directed to the C-terminal of the frataxin protein.

A slight size variation is observed among the various fusion protein constructs, resulting from the variation in the length of the various MTS polypeptides (see FIG. 1), is demonstrated in FIG. 8A, lanes 2-5.

As shown in FIG. 8A, internalization into mitochondria was observed for all four TAT-MTS-FRA fusion proteins.

Remarkably, as shown in lane 3 of FIG. 8A, among the fusion proteins with a MTS that is heterologous to frataxin, the citrate synthase MTS (MTScs) was demonstrated to be delivered most efficiently into the mitochondria.

Notably, FIG. 8A also shows that while for the fusion proteins comprising an MTS which is heterologous to frataxin, namely the MTS of citrate synthase (cs), lipoamide dehydrogenase (lad) and C6ORF66 (orf), only a single band (representing the unprocessed fusion construct) was demonstrated inside the mitochondria, two distinct bands appeared for the fusion protein comprising the native MTS of frataxin (FIG. 8A, lane 2). Without wishing to be bound by theory, this may be the result of instability of the intact fusion protein comprising the TAT and native frataxin MTS regions.

Control Western blot analysis using anti-E1α antibodies (Molecular Probes, Eugene, Oreg.) at a dilution of 1:1,000 are demonstrated in FIG. 8B.

Example 5

TAT-MTS-FRA Fusion Proteins Partially Rescue FA-Patients' Cells as Well as Normal Cells from Oxidative Stress The reduction in the levels of frataxin within the mitochondria has two direct effects in several reported tissue types, namely impaired formation of iron-sulfur (Fe—S) clusters and a rise in intracellular reactive oxygen species (ROS) [35]. The decrease in Fe—S containing proteins, such as heme, electron transport chain (ETC) complexes I-III and the Kreb's cycle protein aconitase severely impairs cellular respiration [36], which is further complicated by simultaneous oxidative damage to these mitochondrial proteins. These events all culminate in an inability of the mitochondria to fulfill the cell's energy requirements resulting in cell death [35].

L-Buthionine sulphoximine (BSO) is an inhibitor of gamma-glutamylcysteine synthetase (gamma-GCS) and, consequently lowers tissue glutathione (GSH) concentrations. GSH plays an important role in cellular defense against a wide variety of toxic electrophiles via the formation of thioether conjugates. Therefore, BSO was used to inhibit de novo glutathione synthesis, depleting an important component of these cells' intrinsic defenses against reactive oxygen species (ROS) and allowing for the accumulation of ROS produced by natural cell processes, known to result in cell death [37]. The mechanism by which BSO inhibits production of GSH and results in cell death was described by Richardson, T. E. et al. [37]. Because they are lacking in Frataxin, Friedreich ataxia cells are extremely sensitive to BSO-induced oxidative stress compared with normal cells [37], and thus are used as an in vitro model of the long-term consequences of absent Frataxin.

Oxidative stress was induced with various concentrations of BSO in patients' cells as well as in normal healthy cells and the effect of the various TAT-MTS-FRA fusion proteins on cell death was measured. As can be seen in FIG. 9, BSO caused cell death of normal lymphocytes as well as of cells obtained from Friedreich ataxia patients. However, patients' cells were more sensitive to BSO-induced oxidative stress, consistent with previous findings, showing higher percentages of cell death. Most importantly, the various TAT-MTS-FRA fusion proteins, which were added a few hours before oxidative stress induction, were demonstrated to partially rescue both normal lymphocytes as well as patients' cells from cell death. This partial rescue was determined by both reduction in cell death and by reduction in caspase 3 activity, as demonstrated in FIG. 9B.

As shown in FIG. 9A and FIG. 9B, at least two out of the three fusion proteins carrying a heterologous MTS (namely, MTSorf and MTScs) demonstrated a superior protective effect with respect to the effect demonstrated by the fusion protein carrying the native MTS, in both patients' cells as well as in healthy cells, from BSO-induced oxidative stress.

A comparative study of the ability of the various TAT-MTS-FRA fusion proteins to rescue BSO-induced oxidative stress of patients' fibroblasts performed as detailed above is shown in FIG. 12A-FIG. 12D for the fusion protein constructs TAT-MTSfra-FRA, TAT-MTScs-FRA, TAT-MTSlad-FRA and TAT-MTSorf-FRA, respectively.

Interestingly, as demonstrated in FIG. 12 two of the protein constructs comprising heterologous MTS, namely the TAT-MTScs-FRA and TAT-MTSlad fusion proteins were more efficient than the fusion protein comprising the native frataxin MTS (TAT-MTSfra-FRA) in partially rescuing BSO-induced oxidative stress of patients' fibroblasts (FIG. 12B and FIG. 12C, respectively).

Similar protective effects in patients' cells induced with various concentrations of BSO were also observed for TAT-MTSorf-FRA and TAT-MTSlad fusion proteins when assayed alone (FIG. 10 and FIG. 11, respectively).

REFERENCES

[1] Chinnery P F, Schon E A (2003) Mitochondria. J Neurol Neurosurg Psychiatry 74: 1188-1199.
[2] DiMauro S, Schon E A (2003) Mitochondrial respiratory-chain diseases. N Engl Med 348: 2656-2668.
[3] Brautigam C A, Chuang J L, Tomchick D R, Machius M, Chuang D T (2005) Crystal structure of human dihydrolipoamide dehydrogenase: NAD+/NADH binding and the structural basis of disease-causing mutations. J Mol Biol 350: 543-552.
[4] Brady R O, Schiffmann R (2004) Enzyme-replacement therapy for metabolic storage disorders. Lancet Neurol 3: 752-756.
[5] Wang D, Bonten E J, Yogalingam G, Mann L, d'Azzo A (2005) Short-term, high dose enzyme replacement therapy in sialidosis mice. Mol Genet Metab 85: 181-189.
[6] Luft F C (2003) Transducing proteins to manipulate intracellular targets. J Mol Med (Berl) 81: 521-523.
[7] Kabouridis P S (2003) Biological applications of protein transduction technology. Trends Biotechnol 21: 498-503.
[8] Green M, Loewenstein P M (1988) Autonomous functional domains of chemically synthesized human immunodeficiency virus tat trans-activator protein. Cell 55: 1179-1188.
[9] Frankel A D, Pabo C O (1988) Cellular uptake of the tat protein from human immunodeficiency virus. Cell 55: 1189-1193.
[10] Futaki S, Suzuki T, Ohashi W, Yagami T, Tanaka S, et al. (2001) Arginine-rich peptides. An abundant source of membrane-permeable peptides having potential as carriers for intracellular protein delivery. J Biol Chem 276: 5836-5840.
[11] Schwarze S R, Ho A, Vocero-Akbani A, Dowdy S F (1999) In vivo protein transduction: delivery of a biologically active protein into the mouse. Science 285: 1569-1572.
[12] Guo X, Hutcheon A E, Zieske J D (2004) Transduction of functionally active TAT fusion proteins into cornea. Exp Eye Res 78: 997-1005.
[13] Del Gaizo V, MacKenzie J A, Payne R M (2003) Targeting proteins to mitochondria using TAT. Mol Genet Metab 80: 170-180.

[14] Harding A E (1981) Friedreich's ataxia: a clinical and genetic study of 90 families with an analysis of early diagnostic criteria and intrafamilial clustering of clinical features. Brain 104: 589-620.
[15] Schulz J B, Boesch S, Burk K, Durr A, Giunti P, et al. (2009) Diagnosis and treatment of Friedreich ataxia: a European perspective. Nat Rev Neurol 5: 222-234.
[16] Durr A, Cossee M, Agid Y, Campuzano V, Mignard C, et al. (1996) Clinical and genetic abnormalities in patients with Friedreich's ataxia. N Engl J Med 335: 1169-1175.
[17] Campuzano V, Montermini L, Lutz Y, Cova L, Hindelang C, et al. (1997) Frataxin is reduced in Friedreich ataxia patients and is associated with mitochondrial membranes. Hum Mol Genet. 6: 1771-1780.
[18] Rotig A, de Lonlay P, Chretien D, Foury F, Koenig M, et al. (1997) Aconitase and mitochondrial iron-sulphur protein deficiency in Friedreich ataxia. Nat Genet. 17: 215-217.
[19] Lodi R, Cooper J M, Bradley J L, Manners D, Styles P, et al. (1999) Deficit of in vivo mitochondrial ATP production in patients with Friedreich ataxia. Proc Natl Acad Sci USA 96: 11492-11495.
[20] Delatycki M B, Camakaris J, Brooks H, Evans-Whipp T, Thorburn D R, et al. (1999) Direct evidence that mitochondrial iron accumulation occurs in Friedreich ataxia. Ann Neurol 45: 673-675.
[21] Tsou A Y, Friedman L S, Wilson R B, Lynch D R (2009) Pharmacotherapy for Friedreich ataxia. CNS Drugs 23: 213-223.
[22] Perlman S L (2012) A review of Friedreich ataxia clinical trial results. J Child Neurol 27: 1217-1222.
[23] Rapoport M, Saada A, Elpeleg O, Lorberboum-Galski H (2008) TAT-mediated delivery of LAD restores pyruvate dehydrogenase complex activity in the mitochondria of patients with LAD deficiency. Mol Ther 16: 691-697.
[24] Rapoport M, Salman L, Sabag O, Patel M S, Lorberboum-Galski H (2011) Successful TAT-mediated enzyme replacement therapy in a mouse model of mitochondrial E3 deficiency. J Mol Med (Berl) 89: 161-170.
[25] Vyas P M, Tomamichel W J, Pride P M, Babbey C M, Wang Q, et al. (2012) A TAT-frataxin fusion protein increases lifespan and cardiac function in a conditional Friedreich's ataxia mouse model. Hum Mol Genet. 21: 1230-1247.
[26] Gakh O, Cavadini P, Isaya G (2002) Mitochondrial processing peptidases. Biochim Biophys Acta 1592: 63-77.
[27] Cavadini P, Adamec J, Taroni F, Gakh O, Isaya G (2000) Two-step processing of human frataxin by mitochondrial processing peptidase. Precursor and intermediate forms are cleaved at different rates. J Biol Chem 275: 41469-41475.
[28] Schmucker S, Argentini M, Carelle-Calmels N, Martelli A, Puccio H (2008) The in vivo mitochondrial two-step maturation of human frataxin. Hum Mol Genet. 17: 3521-3531.
[29] Gakh O, Bedekovics T, Duncan S F, Smith DYt, Berkholz D S, et al. (2010) Normal and Friedreich ataxia cells express different isoforms of frataxin with complementary roles in iron-sulfur cluster assembly. J Biol Chem 285: 38486-38501.
[30] Gavel Y, von Heijne G (1990) Cleavage-site motifs in mitochondrial targeting peptides. Protein Eng 4: 33-37.
[31] Braun H P, Schmitz U K (1997) The mitochondrial processing peptidase. Int J Biochem Cell Biol 29: 1043-1045.
[32] Horwich A (1990) Protein import into mitochondria and peroxisomes. Curr Opin Cell Biol 2: 625-633.
[33] Saada A, Edvardson S, Rapoport M, Shaag A, Amry K, et al. (2008) C6ORF66 is an assembly factor of mitochondrial complex I. Am J Hum Genet. 82: 32-38.
[34] Cheng T L, Liao C C, Tsai W H, Lin C C, Yeh C W, et al. (2009) Identification and characterization of the mitochondrial targeting sequence and mechanism in human citrate synthase. J Cell Biochem 107: 1002-1015.
[35] Santos R, Lefevre S, Sliwa D, Seguin A, Camadro J M, et al. (2010) Friedreich ataxia: molecular mechanisms, redox considerations, and therapeutic opportunities. Antioxid Redox Signal 13: 651-690.
[36] Bulteau A L, O'Neill H A, Kennedy M C, Ikeda-Saito M, Isaya G, et al. (2004) Frataxin acts as an iron chaperone protein to modulate mitochondrial aconitase activity. Science 305: 242-245.
[37] Richardson T E, Yu A E, Wen Y, Yang S H, Simpkins J W (2012) Estrogen prevents oxidative damage to the mitochondria in Friedreich's ataxia skin fibroblasts. PLoS One 7: e34600.
[38] WO 2009/098682

The invention claimed is:

1. A fusion protein comprising a HIV-1 transactivator of transcription (TAT) domain fused to human frataxin and a human mitochondria targeting sequence (MTS) of a human mitochondrial protein being citrate synthase (CS) situated between said TAT domain and said frataxin, wherein said frataxin is C-terminal to said MTS of human citrate synthase.

2. A fusion protein having the amino acid sequence denoted by SEQ ID NO: 28, comprising a HIV-1 transactivator of transcription (TAT) domain having the amino acid sequence denoted by SEQ ID NO: 27 fused to human frataxin having the amino acid sequence denoted by SEQ ID NO: 26 and a mitochondrial targeting sequence (MTS) of human citrate synthase having the amino acid sequence denoted by SEQ ID NO: 23, said MTS situated between said TAT domain and said frataxin, and is linked to said TAT domain via a linker having the amino acid sequence denoted by SEQ ID NO: 32, and wherein said frataxin is C-terminal to said MTS of human citrate synthase.

3. A composition comprising as an active ingredient the fusion protein of claim 1 and a physiologically acceptable carrier.

4. A pharmaceutical composition for the treatment of Friedrich's Ataxia by intravenous administration to a subject in need thereof, said composition comprising a fusion protein of claim 1 and at least one of pharmaceutically acceptable carrier, diluent, additive and excipient.

5. A method of treating or alleviating a symptom of Friedrich's Ataxia comprising intravenous administration to a subject in need thereof a therapeutically effective amount of a composition comprising a fusion protein of claim 1 and at least one of pharmaceutically acceptable carrier, diluent, additive and excipient.

6. The method of claim 5, wherein said fusion protein has the amino acid sequence as denoted by SEQ ID NO: 28.

7. The method of claim 6, wherein said therapeutically effective amount administered is from about 0.5 mg/Kg to about 2 mg/Kg body weight of said subject.

* * * * *